(12) United States Patent
Victor et al.

(10) Patent No.: US 8,487,775 B2
(45) Date of Patent: Jul. 16, 2013

(54) METHOD AND APPARATUS FOR DETERMINING AND ANALYZING A LOCATION OF VISUAL INTEREST

(75) Inventors: Trent Victor, Västra Frölunda (SE); Peter Kronberg, Västra Frölunda (SE)

(73) Assignee: Volvo Technology Corporation, Göteborg (SE)

( * ) Notice: Subject to any disclaimer, the term of this patent is extended or adjusted under 35 U.S.C. 154(b) by 925 days.

(21) Appl. No.: 12/304,287

(22) PCT Filed: Jun. 11, 2007

(86) PCT No.: PCT/SE2007/000567
§ 371 (c)(1),
(2), (4) Date: Oct. 22, 2009

(87) PCT Pub. No.: WO2007/145566
PCT Pub. Date: Dec. 21, 2007

(65) Prior Publication Data
US 2010/0033333 A1 Feb. 11, 2010

Related U.S. Application Data

(60) Provisional application No. 60/804,444, filed on Jun. 11, 2006.

(51) Int. Cl.
*G08B 23/00* (2006.01)
(52) U.S. Cl.
USPC ............ 340/576; 340/575; 340/439; 180/272
(58) Field of Classification Search
USPC .................................. 340/576, 575, 439, 945
See application file for complete search history.

(56) References Cited

U.S. PATENT DOCUMENTS

| 6,091,334 A | 7/2000 | Galiana et al. |
| 6,724,920 B1 * | 4/2004 | Berenz et al. ............... 382/118 |

(Continued)

FOREIGN PATENT DOCUMENTS

| WO | 9849028 A1 | 11/1998 |
| WO | 03070093 A1 | 8/2003 |
| WO | 2004034905 A | 4/2004 |

OTHER PUBLICATIONS

International Search Report for corresponding International Application PCT/SE2007/000567, Oct. 2007.

(Continued)

*Primary Examiner* — Daniel Wu
*Assistant Examiner* — Frederick Ott
(74) *Attorney, Agent, or Firm* — WRB-IP LLP

(57) ABSTRACT

A method of analyzing data based on the physiological orientation of a driver is provided. Data is descriptive of a driver's gaze-direction is processing and criteria defining a location of driver interest is determined. Based on the determined criteria, gaze-direction instances are classified as either on-location or off-location. The classified instances can then be used for further analysis, generally relating to times of elevated driver workload and not driver drowsiness. The classified instances are transformed into one of two binary values (e.g., 1 and 0) representative of whether the respective classified instance is on or off location. The uses of a binary value makes processing and analysis of the data faster and more efficient. Furthermore, classification of at least some of the off-location gaze direction instances can be inferred from the failure to meet the determined criteria for being classified as an on-location driver gaze direction instance.

28 Claims, 28 Drawing Sheets

U.S. PATENT DOCUMENTS

2002/0140562 A1  10/2002  Gutta et al.
2004/0178890 A1*  9/2004  Williams et al. ........... 340/425.5
2005/0030184 A1  2/2005  Victor
2005/0073136 A1  4/2005  Larsson et al.
2005/0131607 A1  6/2005  Breed

OTHER PUBLICATIONS

Supp. European Search Report for corresponding EP 07 74 8230, Feb. 2010.

* cited by examiner

Large eye-closure, take a break

Inconsistent steering, take a break

Inconsistent lane-keeping, take a break

Stay awake, take a break

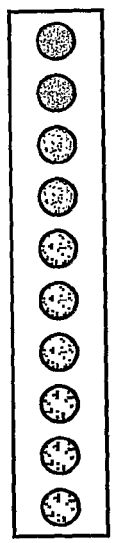
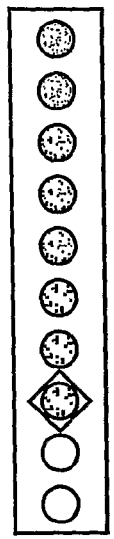
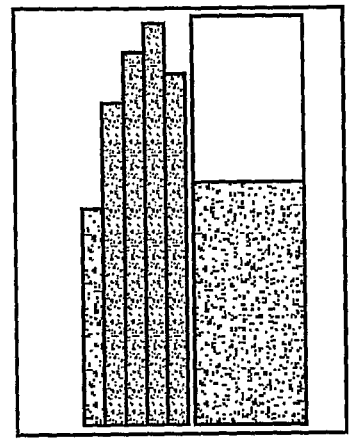
*FIG. 15a*     *FIG. 15b*     *FIG. 15c*
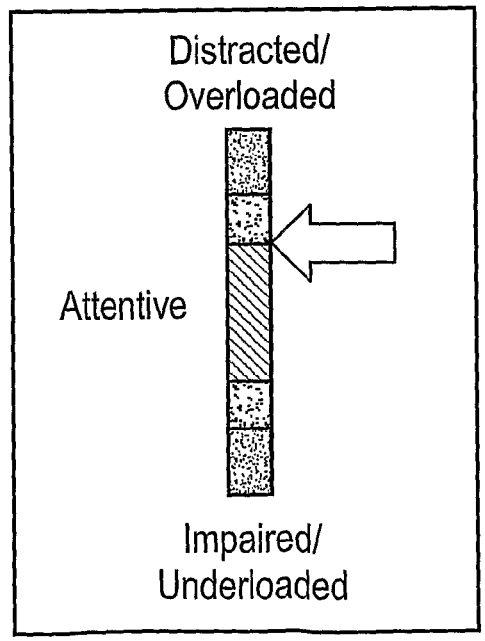
*FIG. 16*

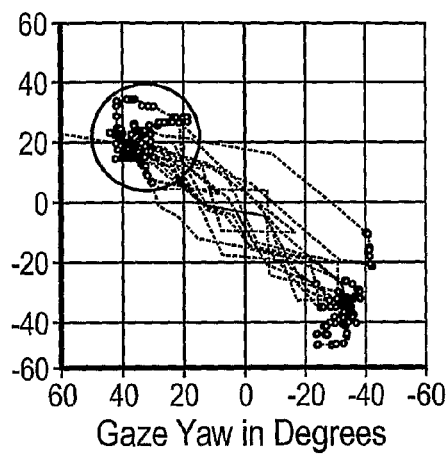 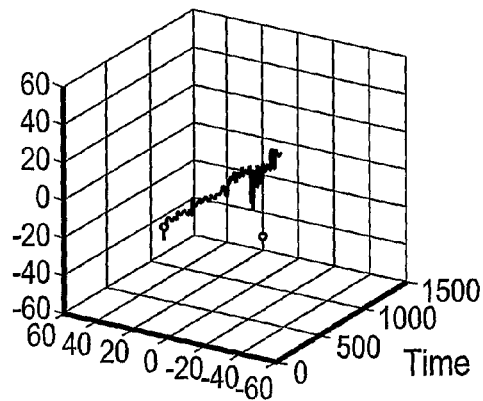
*FIG. 33a*  *FIG. 33b*
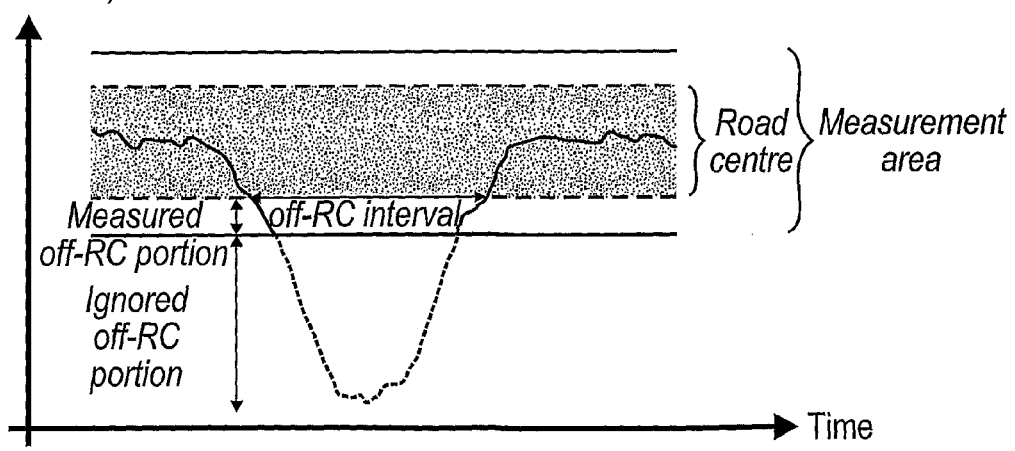
*FIG. 34*

METHOD AND APPARATUS FOR DETERMINING AND ANALYZING A LOCATION OF VISUAL INTEREST

BACKGROUND AND SUMMARY

The present invention generally relates to vehicle piloting; and more particularly, to the visual characteristics and behavior of a driver which is then analyzed to facilitate the driving experience and driver performance.

There is significant ongoing research related to driver fatigue, distraction, workload and other driver-state related factors creating potentially dangerous driving situations. This is not surprising considering that approximately ninety-five percent of all traffic incidents are due to driver error, of which, driver inattention is the most common causative factor. Numerous studies have established the relationship between eye movements and higher cognitive processes. These studies generally argue that eye movements reflect, to some degree, the cognitive state of the driver. In several studies, eye movements are used as a direct measure of a driver's cognitive attention level, and alternatively mental workload.

Knowing where a driver is looking is generally accepted as an important input factor for systems designed to avoid vehicular incidents, an in particularly, crashes. By ascertaining where a driver is looking, Human Machine Interaction (HMI) systems can be optimized, and active safety functions, such as forward collision warnings (FWC), can be adapted on the basis of driver-eye orientation and movements. This may be done as an offline analysis of many subjects, or using an online, or real-time algorithm to perhaps adapt such things as FCW thresholds to the current driver state.

Drivers of all types of vehicles are often unaware of the effects that drowsiness and distraction have on their own abilities for vehicle control. Humans in general, and particularly as drivers, are poor judges of their own performance capabilities. Typically, a driver's self-impression of his or her capabilities is better than actuality. Even persons who have basically good driving skills, will not perform uniformly at all times when behind the wheel of a vehicle. Furthermore, there are many times during driving trips that very little demand is placed on the driver with respect to execution of driving tasks. As a result, drivers are lulled into states of mind where little attention is being devoted to the driving task. Not surprisingly, driver inattention is a leading cause of vehicular collisions, and especially automotive collisions. According to a Nation Highway and Transportation Safety Administration (NHTSA) study of over two and one-half million tow-away crashes in a year's time, driver inattention is a primary cause of collisions that accounts for an estimated twenty-five to fifty-six percent of crashes. In that study, inattention was defined as having three components: visual distraction, mental distraction (looking without seeing) and drowsiness. Common crash types caused by inattention are: rear-end collisions, collisions at intersection, collisions while lane changing or merging, road departures, single vehicle crashes, and crashes that occur on low speed limit roadways.

Drowsy drivers are a well known phenomenon. At least one survey has indicated that fifty-seven percent of drivers polled had driven while drowsy in the previous year, and twenty-three percent had actually fallen asleep at the wheel. It is known that fatigue impairs driver performance, alertness and judgment. Collisions caused by drowsiness are a serious road safety problem, and fatigue has been estimated to be involved in as many as twenty-three percent of all crashes.

From a technological perspective, there is an ongoing and rapid increase of new information systems and functionalities that may be used within vehicles including mobile telephones, navigation aids, the internet, and other types of electronic services. The effect of mobile telephone use on drivers has been foremost in the public eye because of their widespread use, but sales of navigation aids and IT services are also growing fast. Mobile telephones alone have been estimated to have caused 300-1000 fatalities in one years time in the United States, and this is projected to reach 4000 fatalities per year in 2004. Distractions such as handheld telephone use, sign reading, eating food, interaction with other passengers, observing objects and manipulating devices in-the vehicle have the potential for capturing a driver's attention in an excessive way and thus also compromising safety. It is especially important that driving safety not be compromised as these new types of services and activities become more common place in the driving environment.

Driver workload increases based on utilization of these new functionalities and technologies. In this context, "workload" should be understood to refer to how busy a person is and the amount of effort they need to perform required tasks. When a driver has many things to do and is experiencing high workload, a high attention demand is being made on the driver in that there is much to be done at the same time. Drivers often attend to things that are not related to driver control of the vehicle and are therefore technically irrelevant to the driving situation. These things are often called secondary tasks and are potential distracters from driver attention to primary driving tasks. A secondary task becomes a distraction (including visual-, auditory-, cognitive-, and biomechanical distractions) when the driver's attention is captured thereby to a degree that insufficient attention is left for the primary control tasks of driving. As a result, driving performance such as lane keeping and speed control are compromised as ultimately is safety.

Driving tasks and secondary tasks overlap in the sense that some secondary tasks are driving related as diagrammatically shown in FIG. 1. Two difficulties arise from this relationship between the driving and secondary tasks. First, it can be difficult to delineate which secondary task information is "irrelevant to the driving situation" and which is not; and second, certain driving related secondary tasks, for instance, looking for a street sign or planning a driving route may also compromise safety as graphically depicted in FIG. 1.

It should also be appreciated that the driver is often unaware of the effects of distraction on the driving task. Also, drivers cannot reliably determine when they are impaired by fatigue to the point of having a serious vigilance lapse or uncontrolled sleep attacks. The attention management systems outlined herein are intended to increase safety by assisting the driver in drowsy, distractive, and/or high workload situations.

As mentioned above, an interesting use for eye movements is in the ergonomics and HMI fields. For instance, such utilization may be made in determining best placements for Road and Traffic Information (RTI) displays, as well as analyzing whether a certain HMI poses less visual demand than another. These types of analysis can, and are made by studying subjects eye movements while using the device HMI. A primary drawback associated with current methods, however, is that there are few, if any, suitable automated tools for performing the analysis; in their absence, resort is commonly made to labor intensive, manual analysis.

A significant problem in current eye movement research is that every research team seems to use their own definitions and software to decode the eye movement signals. This makes research results very difficult to compare between one another. It is desirable to have a standard that defines visual measures and conceptions. ISO 15007 and SAEJ-2396 constitute examples of such standards in that they prescribe in-vehicle visual demand measurement methods and provide quantification rules for such ocular characteristics as glance frequency, glance time, time off road-scene-ahead and glance duration, and the procedures to obtain them. However, the two standards are based on a recorded-video technique, and rely on frame-by-frame human-rater analysis that is both time consuming and significantly unreliable. As the number of various in-vehicle information and driver assistance systems and devices increases, so will the probable interest for driver eye movements and other cognitive indicators. Thus, the need for a standardized, automated and robust analysis method for eye movements exists, and will become even more important in the future.

Certain eye tracking methods and analysis procedures have been statistically verified to the prescriptions of ISO 15007 and SAEJ-2396. These physical portions of the systems can be configured to be neither intrusive nor very environmentally dependent. At least one example is based on two cameras (a stereo head) being positioned in front of the driver. Software is used to compute gaze vectors and other interesting measures on a real-time basis, indicating such things as head position and rotation (orientation), blinking, blink frequency, and degree of eye-openness. Among other important features in this software are the real-time simultaneous computation of head position/rotation (orientation) and gaze rotation; a feature that has never before been available. Also, it is not sensitive to noisy environments such as occur inside a vehicle. Among other things, "noise" in the data has been found to be a significant factor impacting data-quality-degradation due to such things as variable lighting conditions and head/gaze motion.

It may seem that the previous work done in the area of eye tracking related research is reasonably exhaustive. Yet, as progress is made enabling eye tracking to be more robust and portable, this technology area continues to expand. There are, however, not many on-road studies of driving task-related driver characteristics, and to date, there has been no utilization of eye-tracking data on a real-time basis to calculate measures such as visual or cognitive distraction (see FIGS. 2-4). This is at least partially the result of the time consuming nature of manual segmentation and/or technical difficulties related to the non-portability of commonly used eye-tracking systems. However, in studies conducted in laboratory environments, a variety of algorithms have been developed. Many different approaches have been taken using, for example, Neural Networks, adaptive digital filters, Hidden Markov Models, Least Mean Square methods, dispersion or velocity based methods and other higher derivative methods. Many of these methods, however, are based on the typical characteristics of the eye tracker, such as sampling frequency, and do not work well with other such systems.

Heretofore, there has been no standard for defining what driver characteristic(s) are to be measured, and how they are to be measured. There is no standard that refers to the basic ocular segmentations including saccades, fixations, and eye closures. The standard only concerns glances; that is, the incidence of rapid eye movement across the field of vision.

Interestingly, no current methods take into account smooth eye movements or pursuits; that is, purposeful looks away from the driving path such as looking (reading) a road sign as it is passed. In fact, many studies are designed so that smooth pursuits will never occur, such as by assuring that there are no objects to pursue. This avoidance by current research is understandable; it can be difficult to differentiate a smooth pursuit from a saccade or a fixation. These characteristics are rarely mentioned in the literature. Regardless of the reason(s) that these characteristics have not been considered, smooth pursuits are taken into account with regard to the presently disclosed invention(s) because such smooth eye movement does occur quite often under real driving conditions.

Fundamental to driving a vehicle is the necessity to aim the vehicle, to detect its path or heading, and to detect potential collision threats whether they are from objects or events. This road scene awareness is a prerequisite to longitudinal and lateral control of the vehicle. It should be appreciated that road-center is not always straight ahead of the longitudinal axis of the vehicle, but is often off-centerline due to curves that almost always exist in road-ways to greater and lesser degrees. Even so, research shows that drivers tend to look substantially straight ahead (considering reasonable deviations for road-curvature), with their eyes on the road most of the time; that is, about eight-five to ninety-five percent of the time. Still further, prudence tells the average driver that glances away from the road center or travel path are best timed not to interfere with aiming the vehicle, and to coincide with a low probability of an occurrence of unexpected event or object encounter. Even so, the statistics above demonstrate that even prudent drivers are not always attentive to driving demands, nor are they consistently good managers of their own work loads and distractions when driving.

The theoretical basis for the road center concept considers that the visual guidance of vehicle control is based on optical flow information in the forward roadway region. In order to receive the most relevant visual information, drivers tend to fixate on specific locations, or "anchor points". It has been proposed that information is mainly obtained from two such anchor points: one far point and one near point (e.g. Salvucci and Gray, 2004). For the far region, it has been suggested that the most efficient anchor point is the target that steering is directed to (Wilkie and Warm, 2005), although other anchor points are possible as well (see Victor, 2005 for a review of the literature). The near point is located in the region just ahead of the vehicle (Salvucci and Gray, 2004). The far point has been proposed to account for the rotational component of the optical flow, while the near point is better suited for uptake of the translational component (Victor, 2005).

The region defined by the anchor points is here conceptualized as the road-center (RC). During normal driving, the driver usually shares the visual attention between the road center and other sources of information, e.g. the mirrors, road signs, or other objects inside and outside the vehicle. However, during extended visual time sharing, e.g. when performing a task on an in-vehicle information system (IVIS), the on-road glances need to be focused on the regions most relevant for path control, i.e. the anchor points. This results in a strong concentration of the road-ahead glances (Victor et al., 2005). As mentioned above, this is one of the key motivations for using road-center glances as the basis for visual demand measurement. The second key motivation, also confirmed by empirical results (Victor et al., 2005), is that the great majority of off-RC glances during IVIS task performance are towards the IVIS target.

Road Center Identification—It is important to note that the location of the road center, from the driver's point of view, is determined by the position/orientation of the body and the vehicle relative to the environment. Thus, a substantial amount of variation of the road center is induced by differing physical dimensions of a driver, seating postures, as well as road curvature. For this reason, the RC is estimated from the data in a bottom-up fashion.

Driving is not a particularly demanding task in most instances. For example, it is estimated that during most inter-state driving, less than fifty percent of a driver's perceptual capacity is used. Because of this, drivers often perform secondary tasks such as dialing cellular phones and changing radio channels. When secondary tasks are performed, a time-sharing glance behavior is exhibited in which the eyes are shifted back and forth between the road and the task. This temporal sharing of vision is an implication of having a single visual resource. One could say that the road is sampled while performing secondary tasks instead of the opposite. The problem, which induces collisions, is that unexpected things might happen during the interval when the eyes are off the road and reactions to these unexpected events or objects can be seriously slowed.

The new measures and analysis techniques presented herein exploit this fundamental and necessary driving eye-movement behavior of looking straight ahead or on the vehicle path trajectory. The measures give an accurate off-line assessment of the visual impact of performing visually, cognitively, or manually demanding in-vehicle tasks that have been found to be highly correlated with conventional measures. They also enable a comparison with normal driving. The measures presented herein are importantly also suitable for on-line calculation and assessment of this visual impact and thus represent real-time measures that can be used for distraction and work-load detection. US 2005/0073136 A1 discloses a method for analyzing ocular and/or head orientation characteristics of a subject. A detection and quantification of the position of a driver's head and/or eye movements are made relative to the environment. Tests of the data are made, and from the data locations of experienced areas/objects of-subject-interest are deduced. By utilizing gaze direction data, regardless of whether it is based on head orientation or eye (ocular) orientation, the relative location of the road center and the instrument cluster can be deduced for a particular driver. A concept of identifying the road center is disclosed. WO 03/070093 A1 discloses a system and a method for monitoring the physiological behaviour of a driver that includes measuring a physiological variable of the driver, assessing a drivers behavioural parameter on the basis of at least said measured physiological variable and informing the driver of the assessed driver's behavioural parameter. The measurement of the physiological variable can include measuring a driver's eye movement, measuring a driver's eye-gaze direction, measuring a driver's eye-closure amount, measuring a driver's blinking movement, measuring a driver's head movement, measuring a driver's head position, measuring a driver's head orientation, measuring a driver's movable facial features, and measuring a driver's facial temperature image.

At least one characteristic of the present intention(s) is the provision of validated analysis methods and algorithms that facilitate: automated analysis of behavioral movement data produced by head/eye/body-tracking systems, substantial elimination of human rating, and outputting filtered and validated characteristic data that is robust against errors and noise. Preferably, these facilitations are conducted in accordance with ISO/SAE and similarly accepted present and future standards. Certain algorithms, standards, and facilitations are discussed in U.S. application Ser. No. 10/605,637, filed Oct. 15, 2003 the contents of which are herein incorporated by reference in its entirety.

The present invention provides for a method on analyzing data that is sensed based on the physiological orientation of a driver in a vehicle. The data is descriptive of the driver's gaze-direction and can be defined by a data set. The data is processing using a computer, and from at least a portion of that data, criteria defining a location of driver interest is determined. Based on the determined criteria, gaze-direction instances are classified as either on-location or off-location. The classified instances can then be used for further analysis related to the location of visual interest. Further analysis generally relates to times of elevated driver workload and not driver drowsiness.

A location can be any location of interest, for example a location may include: the road center, a location behind the driver, a location to the left or right of the driver, a rear view mirror, a side mirror, a center console, a car accessory (e.g. radio, window switch, navigation system), a personal accessory (e.g. cell phone, PDA, laptop), or a passenger (e.g. children in car seats or back seat). The above list is not all-inclusive and is provided to show just a few examples of location. As seen from the examples above, the location need not be fixed, but can change with time, for example when the location is a cellular telephone or PDA the location changes with time when the user dials the phone, answers the phone, checks caller ID, checks incoming messages, or sends outgoing messages.

The classified instances are transformed into one of two binary values (e.g., 1 and 0) representative of whether the respective classified instance is on or off location. The uses of a binary value makes processing and analysis more efficient.

Furthermore, the present invention allows for the classification of at least some of the off-location gaze direction instances to be inferred from the failure to meet the determined criteria for being classified as an on-location driver gaze direction instance.

The present invention provides for gaze-direction instances can be sensed and derived from behavioral movements. For example, the gaze-direction instances can be derived from a sensed orientation of: an above-waist portion of the driver's body; an upper torso portion of the driver's body; the head of driver; and/or at least one eye of the driver. Sensors for measuring behavioral movements include a variety of sensors, including, inter alia, cameras, ultrasonic sensing devices, and capacitive sensors.

As seen above, an aim of the present invention is to provide simplified characterization rules which characterize data as either on or off a specified location. In one exemplary embodiment, the characterization is either a road-center visual fixation, or a non-road-center visual fixation. A road-center visual fixation is generally characterized when the driver is looking forward in a typical driving fashion, i.e. the driver is visually fixated on the road-center. Non-road-center visual fixations, where the driver is looking away from the road-center, can be inferred from visual fixations that are not characterized as road-center visual fixations.

In another exemplary embodiment, the characterization is either a rear-view-mirror visual fixation, or a non-rear-view mirror visual fixation. A rear-view-mirror visual fixation is generally characterized when the driver is looking in to the rear view mirror to look behind the vehicle. Non-rear-view-mirror visual fixations, where the driver is not looking in to the rear-view-mirror, can be inferred from visual fixations that are not characterized as rear-view-mirror visual fixations.

Another aim is to adapt certain algorithms to a real-time environment. Another is to identify and provide driver supports that are based on visual behavior and that can assist the driver avoid potentially detrimental situations because of implemented systems that refocus the driver.

In one aspect, the present invention addresses the need for having one standard reference in a vehicle from which various objects and areas that might be of interest to a driver can be located relatively located. A standard frame of reference (defined by relative position/location/orientation {in the context of the present disclosure, utilization of the forward slash mark, /, is utilized to indicate an "and/or" relationship} within the vehicle's interior) to which head/facial/eye tracking data taken from operators of varying size, stature and behavior can be translated is desirable in that it "standardizes" such data for elegant processing for the several purposes described herein.

In at least one embodiment, the presently disclosed invention may be defined as a method for analyzing ocular and/or head orientation characteristics of a driver of a vehicle. It should be appreciated that the analysis techniques or processes described are contemplated as being capable of being applied to stored tracking data that has typically been marked with respect to time, or real-time data, which by its nature, considers time as a defining factor in a data stream; hence the descriptive name, "real-time" data. In any event, this embodiment of the invention contemplates a detection and quantification of the position of a driver's head relative to the space within a passenger compartment of a vehicle. A reference-base position of a "benchmark" driver's head (or portion thereof) is provided which enables a cross-referencing of locations of areas/objects-of-driver-interest relative thereto. It should be appreciated that these areas/objects-of-driver-interest may be inside or outside the vehicle, and may be constituted by (1) "things" such as audio controls, speedometers and other gauges, and (2) areas or positions such as "road ahead" and lane-change clearance space in adjacent lanes, in order to "standardize" the tracking data with respect to the vehicle of interest, the quantification of the position of the driver's head is normalized to the reference-base position thereby enabling deducement of location(s) where the driver has shown an interest based on sensed information regarding either, or both of (1) driver ocular orientation or (2) driver head orientation.

In another embodiment, the presently disclosed invention presents the general concept of road-center (RC) based measures, where visual demand is quantified in terms of glances away from the road center, for both off-line and on-line (real-time) applications. The main advantage of this simplification is that one can allow for lower data quality during glances away from the road (since gaze outside of the RC area, is ignored).

In the event that tracking information is available on both driver head and eye characteristics, sensed information regarding driver ocular orientation is preferentially utilized as basis for the deducement of location(s) of driver interest. A switch is made to sensed information regarding driver head orientation as basis for deducing where driver interest has been shown when the quality of the sensed information regarding driver ocular orientation degrades beyond a prescribed threshold gaze confidence level. As an example, this switch may be necessitated when the driver's eyes are occluded; that is, obscured or covered in some way that prevents their being tracked. The condition of being occluded is also contemplated to include situations in which the tracking sensor(s) is unable to track the eyes because, for example, of an inability to identify/locate relative facial features. For example, eyes-to-nose-to-mouth orientation and reference cannot be deduced (some tracking systems require that a frame of reference for the face be established in order to locate the eyes which are to be tracked and characterized by data values. When the face is not properly referenced, it is possible for some sensor systems to track, for instance, the subject's nostrils, which have been confused for the eyes, or eye-glasses that are being worn distort (refractionally) or obscure (sunglasses) the eye-image. Another example of the eyes being occluded is when the driver's head position departs away from an eyes-forward (predominant driving) orientation beyond an allowed degree of deviation. In these events, the eye(s) of the driver are effectively visually blocked from the tracking equipment (sensors) that is generating the eye-orientation data.

Preferably, a mathematic transformation is utilized to accomplish the normalization of the quantification of the position of the driver's head to the reference-base position. In an onboard installation, it is preferred that the mathematic transformation be performed using a vehicle-based computer on a substantially real time basis.

Probable positions of areas/objects-of-driver-interest relative to the reference-base position are prescribing, in this regard, such prescriptions act as templates against, or onto which the sensed data can be read or overlaid.

Alternatively, probable positions of areas/objects-of-driver-interest are defined relative to the reference-base position based on sensed driver ocular characteristics. In one exemplary development, such definitions of probable positions of areas/objects-of-driver-interest relative to the reference-base position can be established based on the sensed driver ocular characteristic of gaze frequency. Here, establishment of the gaze frequency is based on quantification of collected gaze density characteristics.

In one embodiment of the invention, an area/object-of-driver-interest (which is intended to be interpreted as also encompassing a plurality of areas/objects-of-driver-interest) is identified based on driver ocular characteristics (exemplarily represented as tracking data) by mapping the sensed driver ocular characteristics to the prescribed or defined probable locations of areas/objects-of-driver-interest relative to the reference-base position. That is, identification of an object or area that has been deduced as probably being of interest to a driver can be made by comparison of the observed data (head and/or eye tracking data) to a prescribed template as defined hereinabove, or by comparison to a known data set that has been correlated to particular objects and/or areas in which a driver would be potentially interested:

One example would be that an area-based template devised for a particular vehicle, and relative frequencies at which a driver looks at various locations/object is identified. For instance, it may be found that a typical driver looks in a substantially straight-forward direction about forty percent of driving time and the gauge cluster, including the speedometer about twenty percent of driving time. It is also known that spatially, the center of these two areas is one below the other. Therefore, utilizing gaze direction data (regardless of whether it is based on head orientation or eye (ocular) orientation), the relative location of the road center and the instrument cluster can be deduced for a particular driver. Once that basic frame of reference is established, correspondence to reality for the particular vehicle can be deduced, and a translation to a reference frame can be determined. Still further, glances to the vehicle's audio controls can also be deduced, for instance, if statistically, it is known that a typical driver looks to the audio controls approximately ten percent of normal driving time. Once a period of "learning time" has been recorded, the relative locations of many areas/objects-of-driver-interest can be ascertained on a statistical basis; even independent of any known map of objects/areas, or reference frame in the vehicle.

In another aspect, the disclosure describes tailoring prescribed functionalities performed by the vehicle based on the mapped driver ocular characteristics. This may be as simple as adapting a distraction warning to sound when it is detected that the driver has looked away from the road too long, to causing an increase of the buffer zone maintained behind a leading vehicle by an adaptive cruise control system.

It has been discovered that these areas/objects-of-driver-interest can be identified based either in part, or exclusively on sensed information regarding driver ocular orientation exclusively constituted by a measure of gaze angularity. With respect to at least a reference frame within a particular vehicle (exemplarily identified as a particular make and model of an automobile), angular location of an area/object is particularly elegant because the need to consider distances are removed. That is to say, if an area-location were to be identified as statistically (probabilistically) representing an area/object of probable driver interest, the distance at which that area is located away from the reference frame must be known. This turns on the fact that a defined area expands from a focal point much like a cone does from its apex. An angle from the apex, however, is a discrete measure (see FIG. 5).

The measure of gaze angularity can be derived from a sensed eyeball-orientation-based gaze-direction vector. This could be taken from the observation of one eyeball, but preferably, it is taken as a conglomeration of observations taken from both eyeballs. Therefore, the representative vector is more accurately described as a vector emanating from the region of the subjects nose bridge, and oriented parallel to an average of observed angularity. Furthermore, a measure of gaze angularity could be estimated from the observation of head, face, or other body movements and/or positions.

While the invention has been described with respect to particulars in terms of eyeball angularity herein above, it is also contemplated that related, if not similar results can be obtained from making similar observations based on head orientation. In general, the comparison can be described as using the direction in which the nose points (head-based), as opposed to the direction in which the eyes are oriented from the reference frame defined by the orientation of the reference frame, defining probable positions of areas/objects-of-driver-interest relative to the reference-base position based on sensed head orientation.

In at least one embodiment, the definitions of probable positions of areas/objects-of-driver-interest is determined relative to the reference-base position based on sensed head orientation from which a face-forward direction is deduced. In this case, as with eyeball trajectory measurement data, particular head orientations, and hence a face-forward direction can be established utilizing density mappings indicative of frequency at which a driver looks in a certain direction.

Objects/areas-of-driver-interest can be identified by correlating the representative mapping (therefore, this can also be accomplished from the direct data of angularity) against prescribed/defined probable locations of areas/objects-of-driver-interest relative to the reference-base position.

When addressing head orientation-based analysis, the measure of gaze angularity can be derived from a sensed head-orientation-based gaze-direction vector.

In another embodiment, the invention takes the form of a method for developing a bench-mark (reference frame) for comparison in assessing driver activity and/or driver condition. This method comprises (includes, but is not limited to) collecting (which may also include using a stream of recorded data) a stream of gaze-direction data based on a sensed characteristic of a driver, and based on density patterns developed therefrom, defining gaze-direction-based parameters corresponding to at least one region of probable driver interest.

As before, this method entails utilizing measures of at least one of (1) driver ocular orientation and (2) driver head orientation to constitute the gaze-direction data.

A region representative of typical eyes-forward driving is established based on a high-density pattern assessed from the collected gaze-direction data. Exemplarily, the region may be defined as an area defined in two dimensions such as a parabola or a volume defined in three dimensions such as a cone radiating from the reference frame with an apex thereof essentially located at eye-position of a typified driver relative to an established reference frame.

The collected gaze-direction data is compared to the established representative region, and thereby identifying gaze departures based on the comparison. Based on similar comparison, other qualities of the environment or the driver may be deduced. For example, the gaze-direction data can be used to identify and/or measure such things as driver cognitive distraction, driver visual distraction, and/or high driver work load conditions.

Still further, the method contemplates and provides means for quantifying the severity (degree) of a driver's impairment with respect to performing driving tasks based upon an ascertained frequency or duration (depending on whether occurrences are discrete or continuous incidents) at which such an indicative condition as gaze departure, cognitive distraction, (3) visual distraction and (4) high driver work load is detected in a prescribed time period.

The incidents of interest can be logged, stored and/or transmitted for further analysis by a processor. Conversely, the data representative of the incidents of interest can be analyzed on a real-time basis either locally, or remotely if also transmitted in real-time.

Attention management systems and methods have as an objective to increase safety by assisting drivers in drowsy, distractive, and/or high workload situations. Functional specifications are provided for a number of attention management systems that can be characterized to include drowsiness managers, distraction managers, managers for distraction adaptation of forward collision and lane change warning systems, and workload managers that are at least in part controlled based on driving demand estimations observed or deduced from visual behavior of the driver. A hardware system that can be suitably employed to perform these driver attention management tasks is also described. A "platform" for development of the instant drowsiness and distraction manager based on Human Machine Interaction (HMI) is also disclosed, as is description of continuous and post-trip attention feedback systems. The HMI approach has as an objective thereof to counteract driver inattention by providing both imminent collision warnings, as well as attention-feedback to cause positive behavioral change.

At least one utilization of such analysis is to provide driver feedback when the severity quantification exceeds a prescribed severity threshold level. For instance, a driver may be warned when excessive levels of visual distraction (too much looking away) or cognitive distraction (not enough looking away—staring ahead when preoccupied) occur.

Another utilization of the output from the analysis is to tailor prescribed functionalities performed by the vehicle when the severity quantification exceeds a prescribed severity threshold level. An example would be causing an adaptive cruise control system to institute additional space between a leading vehicle when the driver is assessed to be distracted or inattentive.

One particularly advantageous mode for analyzing the stream of collected gaze-direction data is the utilization of a primary moving time-window of prescribed period traversed across the data series (a well known analysis tools to those persons skilled in the statistical analysis arts), and detecting characteristics within the primary moving time-window indicative of an occurrence of driver time-sharing activity. An example is taking an average of certain data within a moving ninety second window. As the window progresses along the data series, new data is added to the consideration and the oldest data is disregarded (new-in and old-out in equal amounts, based on time).

Utilization of this process can be used to identify periods of high driver workload based on a frequency of threshold-exceeding occurrences of driver time-sharing activity. In order to rid the window of the effect of the detected occurrence, refreshment (flushing or restoring to normal) of the primary moving time-window upon the detection of cessation of an occurrence of driver time-sharing activity is caused. In this way the effect of the occurrence is minimized after detection and analysis, thereby readying the system for a next departure from normal.

As will be discussed in greater detail hereinbelow, several characteristics of ocular activity can be identified based on observed eye activity. Some common characteristics easily recognized by the lay person are blinking and glances. What may not be as readily appreciated by the lay person is that such things as a glance may be characterized or identified based upon lesser known constituent eye-activities such as saccades, fixations and transitions, each of which have measurable defining characteristics.

In another embodiment, the invention takes the form of a method for automated analysis of eye movement data that includes processing data descriptive of eye movements observed in a subject using a computer-based processor by applying classification rules to the data and thereby identifying at least visual fixations experienced by the subject. These rules or characteristics are discussed in greater detail hereinbelow. Analysis is also made of gaze-direction information associated with the identified fixations thereby developing data representative of directions in which the subject visually fixated during the period of data collection that is presently being analyzed.

Applied classification rules comprise at least criteria defining fixations and transitions. The classification rules can also providing criteria to define saccades are additionally utilized.

The data can be segregated, based at least partially on gaze-direction of fixations, into delimited data sets, each delimited data set representing an area/object-of-subject-interest existing during the period of data collection.

In another respect, glances are identified by applying at least one glance-defining rule to the data, each of the identified glances encompassing at least one identified fixation. In this aspect of the invention, the glance-defining rule is generally defined by at least one of the following characteristic including: glance duration, glance frequency, total glance time, and total task time.

In another aspect, a relative density is assessed of one glance set in comparison to at least one other glance set, and based thereupon, the method identifies the represented area/object-of-subject-interest of the compared glance set.

In a similar regard, the inventive method contemplates assessing a relative density of at least one glance set among a plurality of glance sets, and based upon a mapping of the assessed relative density to known relative densities associated with settings of the type in which the eye movement data was collected, identifying the represented area/object-of-subject-interest of the compared glance set. For example, using the percentages for known dwell periods on certain objects or areas of driver interest during normal driving conditions, those objects or areas can be identified from the collected data.

In another aspect, relative densities of at least two glance sets developed from data descriptive of eye movements observed in a spatially known setting are assessed and the represented area/object-of-subject-interest of each of the two compared glance sets is ascertained therefrom. Locations of the represented areas/objects-of-subject-interest are then ascertained in the known setting thereby establishing a reference frame for the known setting because the deduced locations can be mapped or overlaid on known locations of the objects/areas.

In a particularly preferred embodiment, the subject is a driver of a vehicle, and based on a density of at least one of the glance data sets, an eyes-forward, normal driver eye orientation is deduced.

A further aspect of the invention in which a vehicle driver is the subject, contemplates utilizing a plurality of analysis protocols, the selection of which is dependent upon prevailing noise characteristics associated with the data set being processed.

In one development, a first data filter of predetermined stringency is applied to an input stream of data comprising the data descriptive of eye movements observed in a driver of a vehicle. The computer-based processor is utilized, and therefrom, a first filtered data stream is outputted that corresponds to the input stream of data. (This concept of correspondence can be one in which each outputted value corresponds to the inputted value from which the outputted value is derived. Quality of the outputted first filtered data stream is assessed by applying a first approval rule thereto, and data of the outputted first filtered data stream passing the first approval rule being outputted and constituting an approved first stream of data.

In a further development, a second data filter is applied to the input stream of data that is of greater stringency (more smoothing to the data) than the first data filter utilizing the computer-based processor; and therefrom, a second filtered data stream is outputted that corresponds to the first filtered data stream via its common derivation from the input stream of data (again, correspondence/comparison based on having been computed from the same input data value). Quality of the outputted second filtered data stream is assessed by applying a second approval rule thereto, and data of the outputted second filtered data stream that passes the second approval rule is outputted and constitutes an approved second stream of data.

From the two approved data streams, a collective approved stream of data is composed that is constituted by an entirety of the approved first stream of data, and the collective approved stream of data being further constituted by portions of the approved second stream of data corresponding to unapproved portions of the outputted first filtered data stream.

In at least one embodiment, the first and second approval rules are the same; in another, the first and second approval rules are based on the same criteria, but may not be the same rules.

In a further development, the method comprises selecting at least two analysis protocols to constitute the plurality from a group consisting of: (1) a velocity based, dual threshold protocol that is best suited, relative to the other members of the group, to low-noise-content eye and eyelid behavior data; (2) a distance based, dispersion spacing protocol that is best suited, relative to the other members of the group, to moderate-noise-content eye and eyelid behavior data; and (3) an ocular characteristic based, rule oriented protocol that is best suited, relative to the other members of the group, to high-noise-content eye and eyelid behavior data.

In an associated aspect, the selection of protocols for any given data set is biased toward one of the three protocols in dependence upon a detected noise level in the data set. In another aspect, the rule oriented protocol considers one or more of the following standards in a discrimination between fixations and saccades: (1) fixation duration must exceed 150 ms; (2) saccade duration must not exceed 200 ms; and saccades begin and end in two different locations.

In a further regard, quality of the data descriptive of behavior movement is assessed based on relative utilization of respective analysis protocols among the plurality of analysis protocols. Alternatively, or in association therewith, the quality assessment can be made considering time-based, relative utilization of respective analysis protocols among the plurality of analysis protocols over a prescribed time period.

BRIEF DESCRIPTION OF DRAWINGS

FIGS. 15(a)-(c) illustrate various "active" graphical displays for displaying realtime driver information according to the teachings of the present invention;

FIG. 16 provides an illustration of real-time driver feedback in a comparative format against an indication of an optimal level of attention;

FIG. 33a provide a two dimensional graph demonstrating identification of the road-center ahead area based on glance behavior; and FIG. 33b provides a three-dimensional graph demonstrating identification of the road-center ahead area based on glance behavior as a function of time; and FIG. 34 illustrates an alternative determination of road-center area.

DETAILED DESCRIPTION

Figure 1:
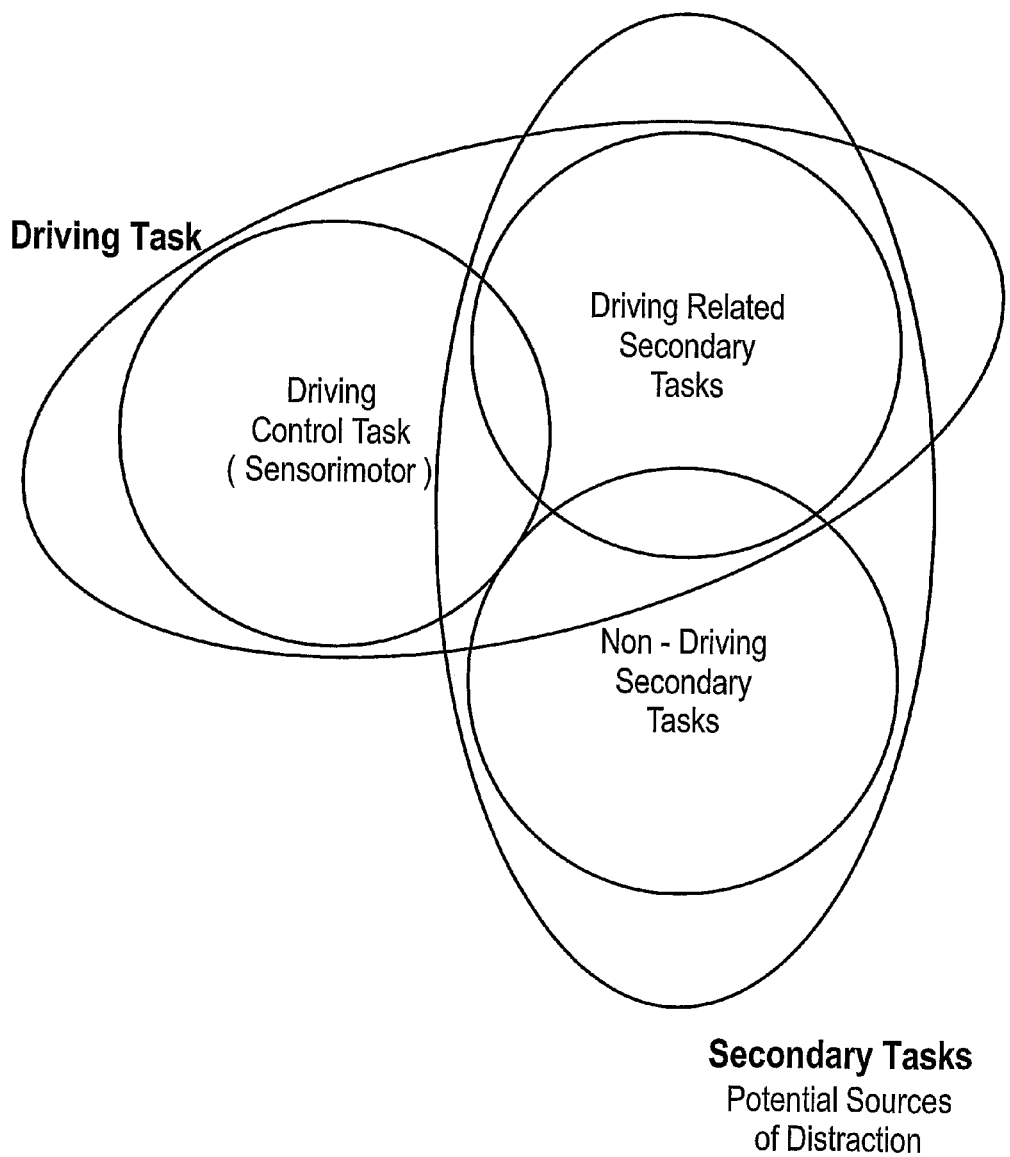
FIG. 1 is a diagrammatical representation of the interrelationship of driving control tasks and secondary tasks.
Figure 2:
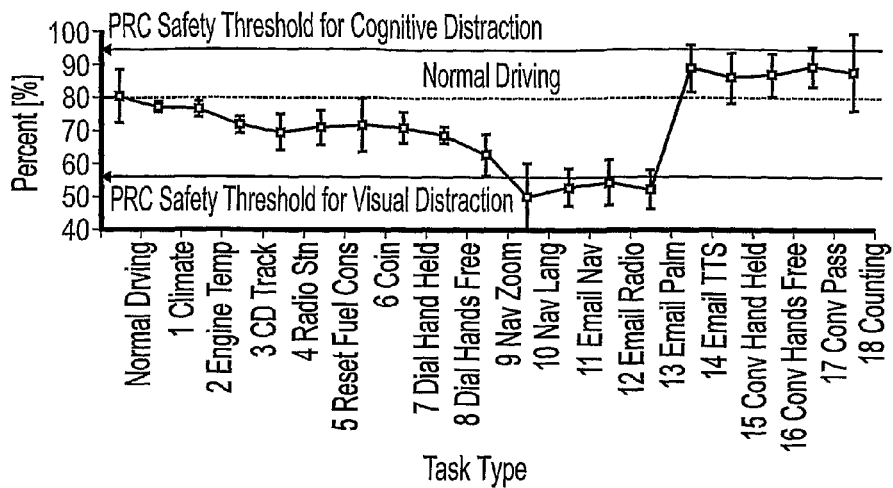
FIG. 2 is a graphical demonstration showing the use of percent road center to measure the relative impact of various in-vehicle tasks.

Before the actual data treatment techniques that are the focus of the presently disclosed invention(s) are described, some basic information will be provided regarding rudimentary characteristics of eye movements, as well as some general information about typical tracking systems that can be used to sense, quantify, and optionally record data descriptive of head and/or eye orientation (location and movement characteristics) in an effort to facilitate those readers possessing less than ordinary skill in these arts.

With respect at least to eye movement-based systems, presently available sensing systems used for gathering eye movement data deliver "raw" eye-movement signals that are rather noisy and which includes artifacts. As will become evident from reading the balance of the present disclosure, typically, head orientation tracking data can be utilized as an approximation, and therefore often a valid substitute for eye tracking data.

Algorithms of the present invention(s) process this information and produce output representing such things as measures of glance frequency (the number of glances toward a target area during a pre-defined time period), single glance duration, total glance time and total task time. The algorithms embody rules that are defined to trigger different warnings; for example, if the driver looks at his/her cellular for more than two seconds without looking back to the road. The defining of the exact trigger rules is the product of trimming in the real-time systems that are continually under development.

Aspects of the presently disclosed inventions include two differently based algorithms; one for off-line post data-gathering processing, and one for real-time processing that takes place essentially simultaneously with the data gathering (when the quantified characteristic is being performed). They are similarly based, but the real-time algorithm has an initialization procedure and lacks some of the off-line features. A primary purpose and benefit of off-line analysis is the treatment of recorded or stored characteristic data. A primary purpose of real-time analysis is to immediately treat collected data, and make it available for essentially simultaneous utilization for such things as feedback to the observed subject, or adaptation of relevant systems such as to vehicular systems when the subject of the observation is a vehicle driver.

Concerning drivers, one of the purposes for the off-line algorithm is to analyze eye-movement data from tasks, such as changing radio station or using the RTI system (while driving), to determine how much visual demand the unit poses on the driving task. A purpose of the real-time algorithm is to determine how much the driver looks at the road. One objective of the present invention is to adapt or enable the real-time algorithm so that results similar to that from the off-line algorithm are obtainable.

Eye movements can generally be divided into two categories: saccades and fixations. A fixation occurs when the eyes are fixated on something; for instance, the letters on this page. This is also when the brain can assimilate information which is interpreted as the visual images of the thing(s) upon which fixation is focused. A saccade on the other hand is the movement in between fixations; that is, changing the point of regard. Saccades are very fast (with peak velocities at 700% for large amplitudes) and the viewer's brain suppresses recognition of these incidents because light is moving across the retina at these times too fast to be interpreted by the brain.

A glance towards something, for instance a mobile telephone, is a combination of a saccade away from a predefined target area (e.g. the road), initiation of the glance, and fixations at a new target area (e.g. the mobile telephone). The glance is terminated when a new saccade away from the second target area is initiated. Successive saccades and fixations within the same target area are defined as part of the same glance.

Certain of the goals and advantageous aspects of the present invention(s) can be summarized as: (1) The hybrid algorithm, even at the level of just combining velocity and dispersion based algorithms, is new especially when combined with ocular rules. Heretofore, the physical capabilities of the eyes have not been taken into account when segmenting eye-movements; (2) The idea and procedure to localize the road center area using the density function peak as its center that is more detailed than merely designating the mean value of the "mountain;" (3) The algorithms, as a whole, and the way each different algorithm part cooperates with the others. The concepts of Percent Road Center (PRC) and Absolute Percent Road Center (A-PRC) as measures of driver attentiveness.

The algorithms are not only intended to produce the described measures, but can also be used to determine all measures defined in the ISO 15007-2, as well as the measures in the SAEJ-2396.

Oculumotor concepts are well studied; generally, ocular motion is divided into several different categories that may be exemplified as saccades, microsaccades, smooth pursuit, vergence, tremor, drift, and the like. For purposes of the present invention, however, ocular motion is divided into two fundamental categories: saccades and fixations. The rational of the present invention is that all data points that are not saccades, are fixations. This includes smooth pursuits, which occur frequently during driving, in the fixation conception described hereinbelow.

Figure 6:
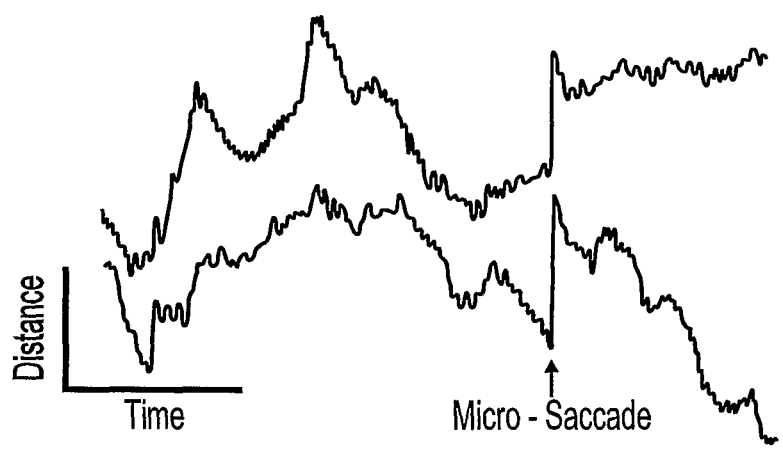
FIG. 6 is a graphic view of details of two eye movements demonstrating a micro-saccade, drift and tremor.

Fixations are defined as pauses over informative regions where the eyes can assimilate information. To be a valid fixation, the pause has to last for at least some 150 ms, the same being about the time the human brain needs to utilize the information. Although it is referred to as a "fixation," the eyes still move, making micro movements like drift, tremor and micro-saccades while "fixed" on the area. These small movements are of very low amplitude and are part of what defines a fixation. FIG. 6 represents a typical fixation with drift, tremor and a micro saccade. Therein, activity of a subject's two eyes are graphed, one above the other; time is charted on the horizontal axis, while distance is represented on the vertical axis. These movements are fortunately either very slow (typically on the order of 4 and 200 s.sup.-1) or very small (typically on the order of 20 40 inches), which prevents their detection by typical equipment used in these types of applications. This is a benefit, because these deviations would other-wise be viewed as noise.

Figure 7:
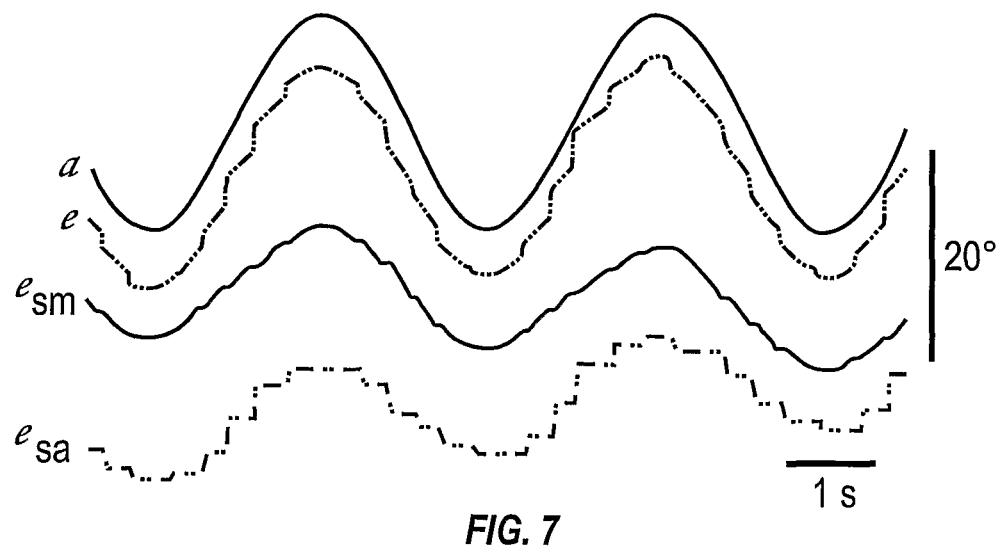
FIG. 7 is a graphical demonstration of different component characteristics of an eye movement sample.

Other larger movements, but still with sub-saccadic velocities, are termed smooth pursuits. They are a subcategory of a fixation; that is, a fixation on a moving target or a fixation on a stationary (or moving) object while the observer is in motion. When we track a target, the eyes use small saccades to bring fovea on to the target, then slower, continuous movements are performed that track the target, and are dependent upon its speed. The slow movements, with velocities ranging roughly between 80 and 160 degrees per second, constitute smooth pursuits. This behavior is shown graphically in FIG. 7 were a subject is tracking a point moving on a sinuous path represented by the curve (a). The curve (e) represents the entire eye-movement, including saccades and smooth pursuits. The curve (esa) represents the removal of smooth pursuits, and (esm) shows the curve with saccades removed. In general, the entire tracking behavior is referred to as a smooth pursuit and can be considered to be a drifting fixation. For this reason, this type of behavior is referred to herein relative the present invention(s) as a fixation due to the fact that information is being processed during this movement and the saccades are two small to be detected with available eye-movement tracking systems.

Saccades are rapid eye movements that occur as a person's view changes between two points. Saccadic movement varies in amplitude, duration, velocity and direction. The duration of saccades larger than about five degrees in amplitude will be about 20-30 ms; thereafter, about two milliseconds can be added for every additional degree. Peak velocities typically range from some 10 degrees per second for amplitudes less than 0.1. degree., to more than 700 degrees per second for large amplitudes.

Figure 8:
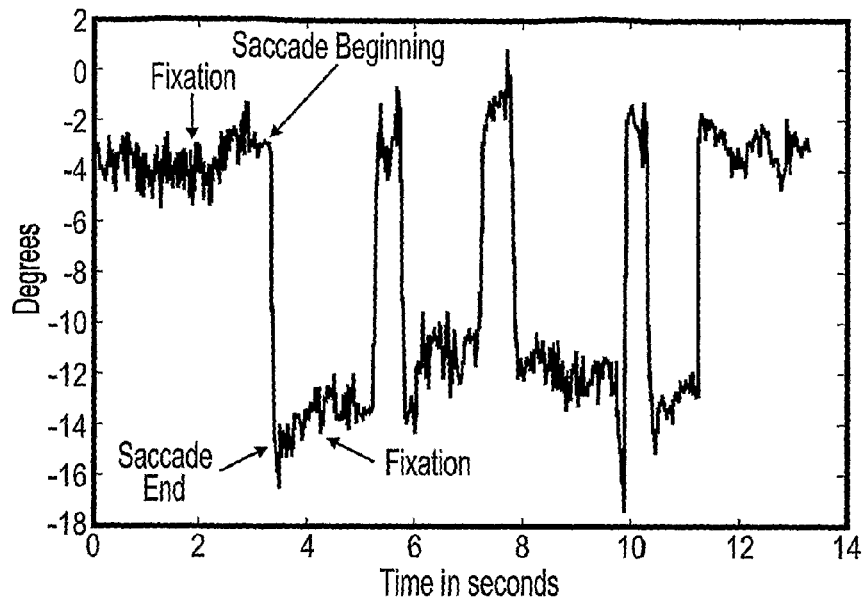
FIG. 8 is a graphical depiction of a plurality of fixations and saccades.

Typical saccades from one point of regard to another are shown in FIG. 8, which depicts an example of a good tracking measurement with virtually no noise. An exemplary saccade is shown beginning at point (A) and ending at point (B). Also, the illustrated eye movement only consists of movement around one axis; that is, no saccades were measured in the horizontal plane.

During saccadic movement, the human brain generally does not perceive information since light is moving too fast over the retina. It should be appreciated, however, that it has in fact been shown that some information is actually being processed during saccades. Recognized perception only occurs if an observed object is moving at the same speed and in the same direction as the eyes. The general absence of information forces the brain to make a calculation of amplitude and duration in advance. Inaccuracy and noise in this process almost always generates an over- or under-shot on the order of some degrees. This is corrected by drift or a new saccade that is much shorter than the previous, and therefore more precise. Here, a saccadic undershot represented by the long vertical portion of the trace (A) is corrected by the shorter vertical portion representing a corrective mini-saccade (B). Such a corrective saccade is often of such low amplitude that it is undetectable using known eye-tracking machines, and is considered instead as added noise.

Apart from these three kinds of movement, there is a different kind of visual behavior commonly referred to as blinks. Humans normally blink about once every two seconds; a characteristic that has a devastating impact on gaze estimation. During the actual closure of the eyes during a blink, gaze cannot be measured and since blinks do occur during both saccades and fixations, it is hard to anticipate where the eyes will be looking when again visible to the tracking machine. Fortunately, blinks are very fast; on the order of 200 ms for an entire blink. This means that the eyes are totally occluded for only about 100-150 ms. Because subjects are generally totally unaware of the occurrence of blinks, the present invention achieves a more coherent and stable perception of reality by suppressing the recognition of both saccades and blinks.

Properties of the eyes work in favor of segmentation, meaning there are physical boundaries for ocular movements that provide rules for classification. For example, one saccade cannot be followed by another with an interval less than some 180 ms; this means that it is unlikely for a saccade to last for more than 200 ms. A 200 ms saccade would have an amplitude of about 90 degrees which is very uncommon. Still further, any measured saccade that is longer than about 220 ms is more likely to be two saccades, with one fixation in-between. Another interesting fact is a subject's suppression of blink recognition mentioned above. Subjects are generally unaware of the occurrence of blinks, and therefore can generally be removed from the analysis since eye behavior is not affected by their occurrence. The following constitute physical boundaries of the eyes that are relevant to the present invention(s): fixations last for at least, about 150 ms; a saccade can not be followed by another with an interval less than some 180 ms; the human visual field is limited; a fixation can be spatially large (smooth pursuit); saccades are suppressed by the visual center; blinks are suppressed by the visual center.

For the Driver of a vehicle there could be even more restrictions such as: it is not likely to find fixations on the inner ceiling or on the floor during driving, especially not during a task; a significant proportion of a subject's attention (and fixations) are likely to be found on the center of the road and smooth pursuit velocities are low to moderate. As an example, oncoming traffic and road signs trigger most measured pursuits. In the present invention, these boundaries are used to define a framework that can be used as a part of the segmentation of driver eye movements.

According to the present inventions, ocular measures are divided into two groups, glance based measures and non-glance based measurers. These two groups are formed by the outcome of a basic ocular segmentation where fixations, saccades and eye-closures are identified.

As intimated above, different researchers have different methods of analyzing data and defining fixations/saccades. Having uniform rules and benchmarks are important so that all such analysis methods can be based on a generally accepted international standard. This is why the measures in this work are based on the definitions in the ISO 15007-2 and SAEJ-2396 standards. They both standardize definitions and metrics related to the measurement of driver visual behavior, as well as procedures to guarantee proper conduction of a practical evaluation. The SAE document depends on many terms of the ISO standard, and each works as a complement to the other.

Human Machine Interaction (HMI) are also considered; examples of such HMI concepts have been more thoroughly described in U.S. Pat. No. 6,974,414 filed 19 Feb. 2003 and entitled SYSTEM AND METHOD FOR MONITORING AND MANAGING DRIVER ATTENTION LOADS, the disclosure of which, in its entirety, is hereby expressly incorporated. Therein, concepts for how to present these warnings are presented.

In at least one embodiment, the present invention provides a system and method that enables the implementation of attention management concepts in a vehicle, including exemplary hardware upon which the inventive functionalities can be accomplished. Several basic questions and goals are addressed herein, including: what visually derived support do drivers need and how should it be conceptualized to achieve acceptance; how can real-time recognition of driver visual behavior be applied to reduce driving errors and prevent accidents; what is the commercial feasibility of implementation. Functional descriptions are provided for drowsiness managers; distraction managers, distraction adaptation of forward collision and lane change warning systems; and workload managers. Systems and methods for implementing driving demand estimation from visual behavior are also included.

One or more of these systems and methods are individually, as well as collectively, described as making-up a so-called attention management system. One possible component of these systems, as well as a component of the several inventions described herein, is the attention support demonstrator that can be used to implement these systems and methods for demonstration and testing. Examples of driving demand estimation from visual behavior are also described herein.

Figure 9:
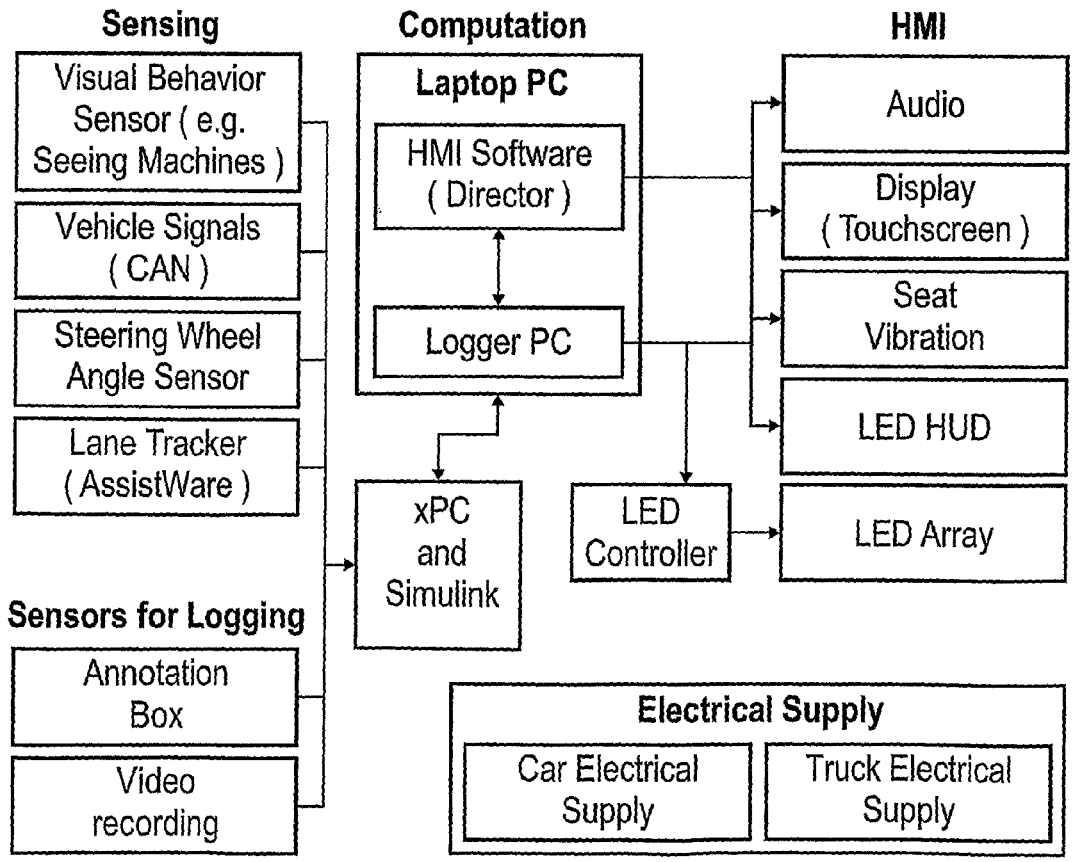
FIG. 9 is a flowchart representing one embodiment of an attention management system that includes hardware and functional modules for sensing, computation, HMI, and electrical supply.

In one embodiment, the attention management system includes hardware for (1) sensing, (2) computation, (3) HMI, and (4) electrical supply. The units or functional modules can be exemplarily configured (interrelated) as illustrated in FIG. 9, and are suitable for implementation in such vehicles as automobiles and trucks.

A visual behavior sensor is employed such as that which is available from the company, SeeingMachines, and which can be adapted to be installed in a vehicle. This type of system can include (1) a stereo camera head, (2) a personal computer (PC), and (3) appropriate driving software. A visual behavior sensor such as that produced and sold under the trade name SMARTEYE may also be optionally employed. Other visual behavior measurement devices also may include, for example, cameras, ultrasonic devices, and capacitive sensors. Cameras are can be used for performing image processing for obtaining eye movement, eye closure, and/or head movement data. Ultrasonic devices and capacitive sensors can be used for providing positional information, for example, body posture and head position.

In one example, vehicle performance signals can be acquired from the CAN bus. A steering wheel angle sensor can also utilized, as well as lane tracking hardware and software. An annotation box and video recording hardware is utilized. An onboard personal computer, or similarly capable computing device is utilized. Alternatively, and especially to facilitate testing and implementation, a laptop computer can be employed that exemplarily runs such software as "Director" and "Simulink." An xPC can also be installed and utilized. From a hardware perspective, LED controller hardware is employed. Audio HMI (warning sounds, recorded messages) are provided for via the computing device. A touchscreen for user input can also be utilized. It should be appreciated that some of these embodiments are suitable for product development and facilitate system testing, but when commercialized, the several components are integrated directly into the vehicle.

A seat vibration arrangement or similar driver alert can be included. In a preferred embodiment, a LED HUD (heads up display) is employed. A LED array (display), controlled by a LED controller can also be utilized. An electrical supply for the entire system can be tapped from the carrying vehicle.

A drowsiness manager can be implemented in two configurations. In a first example, it is entirely PC based; that is, no external hardware or external communication capabilities are required. This embodiment is scenario based; that is, tracking of a drowsiness episode based on real PERCLOS (analysis that considers scan patterns, number and length of fixations, saccade latency and the like) data rather than in real-time. The hardware functionality stimulates the driver via such stimuli as a visual display such as LED-based or HUD, or physical stimulation such as seat vibration, in another embodiment, HMI hardware and Simulink communication is implemented.

A "platform" upon which several drowsiness manager countermeasures may be implemented is desirable, and upon which tests may be conducted. An exemplary platform for such implementation is schematically illustrated in FIG. 10.

Figure 10:
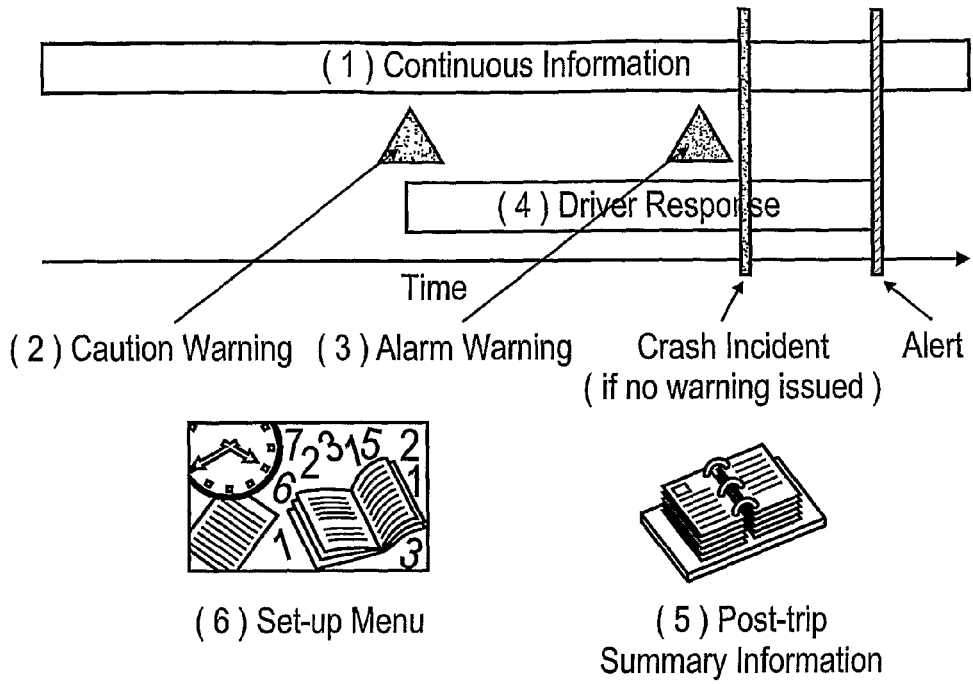
FIG. 10 is a diagrammatical representation of a platform upon which several drowsiness manager countermeasures may be exemplarily implemented.
Figure 11A:
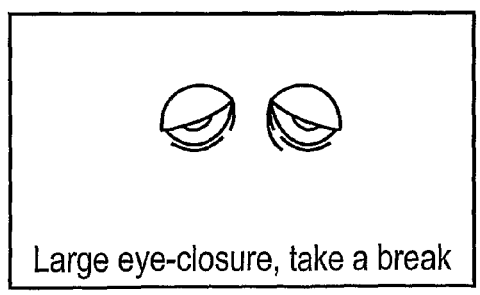
FIG. 11 depicts exemplary representations of possible display warnings to a driver.
Figure 11B:
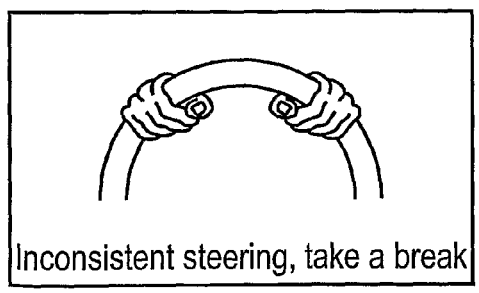
Figure 11C:
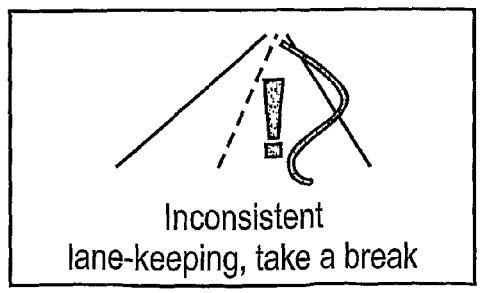
Figure 11D:
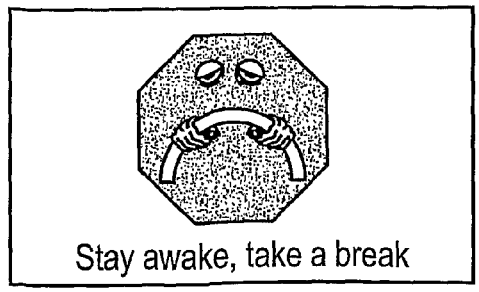

The illustration of FIG. 10 may be considered to depict a director program. Such an arrangement is easy to change with respect to different HMI components; for instance, to provide (1) continuous information streaming to the driver, to provide (2) cautionary warnings, (3) eminent danger warning alarms, (4) driver response tests, (5) post trip summary information, and (6) operator input set-up menu(s).

In one embodiment, a caution warning to the driver is provided. The driver is able to choose between warning versions, but is not able to completely disable the warning. Exemplarily, a beep followed by an optional voice message warning can be played to the driver such as "<automated insertion of drowsiness cause>, 'take a break.'" An icon can be alternatively displayed to the driver either individually, in conjunction with an audible warning, or together with a printed version of the warning.

Exemplary icon warnings are shown in FIGS. 11(a)-(d) for (a) large eye closure detection, (b) inconsistent steering detection, (c) inconsistent lane-keeping detection, and (d) driver drowsiness detection. One or more of these icons can be simultaneously displayed depending upon detected driver conditions.

In another embodiment, a microphone is included so that the driver can record or supply his or her own warning much like in a telephone answering machine and other customizable audio play-back devices.

In still another embodiment, driver physical-stimulation warnings are applied. Preferably, the driver can choose between warming-types in the set-up menu, but in at least one embodiment the operator is prevented from completely disabling the physical warning. An example of such a physical stimulation would be seat vibration.

In another version, a flashing "HUD" LEDs may be used to sharply stimulate the driver; again, alone or in conjunction with the other types of warnings described herein. In a preferred embodiment, capabilities are provided to the driver for enabling up to three of the described warning types to be simultaneous presented when active.

A driver response functionality; that is, reaction-time to a signal, is also provided. With regard to this functionality, the driver is able to both enable and disable, as well as choose between warning versions in the set-up menu.

Figure 12:
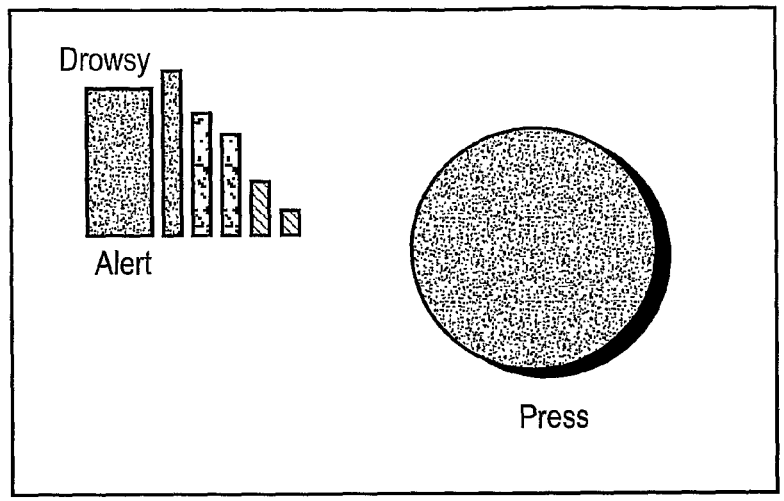
FIG. 12 depicts an exemplary, interactive, driver response panel.

In a predetermined amount of time, for example five to eight seconds post-warning, a driver response function operates. Exemplarily, there will be a beep, with text "Press" under a button presented on a touch screen as illustrated in FIG. 12. If the driver does not react within the prescribed amount of time, or according to some other reaction time based algorithm, then an alarm warning will issue. This continues until the driver stops the vehicle, becomes alert and this fact is system-detected, or the driver turns the function off.

In order to provide customizing capabilities to the operator, exemplary options that may be selected via the HMI components are illustrated below:

HMI Component Option(s) (1) Continuous drowsiness feedback on/off feedback Choice of one of several versions (2) Caution Voice message Warning on/off Default message on/off User supplied message on/off Use multiple icons or Use default icon (3) Alarm/Choice of following Stimulation (at least one Warning must be checked) Seat vibration on/off Sound on/off HUD visual warning on/off Fan (not implemented in iteration 1) Scent (not implemented in iteration 1) Cut gas (not implemented in iteration 1) Drive to roadside (not implemented in iteration 1) Use multiple icons or Use default icon (4) Driver Response Driver response on/off A distraction manager can be implemented in two embodiments. In a first embodiment, the distraction manager is entirely PC based with no external hardware or communication capabilities. It is scenario based; that is, a timeline of a distraction episode is given rather than in real-time. The hardware functionality is simulated. A second embodiment is based on a hardware implementation that includes the capability of real time communication.

Another aspect of the invention is safety threshold based distraction warnings. Warnings are provided that inform the driver of safety compromising distractive behavior. As appreciated hereinabove, drivers are often unaware of the effects of their distraction on their driving capabilities. Thus a goal of the safety based distraction warnings is to give the driver feedback about driving control task performance decrements. That is, if distraction is detected (i.e. glance behavior is over an appropriate safety threshold and/or vehicle performance deteriorates during glance behavior), the system provides one or more of the following alerts. A sound such as a simple beep or a performance-specific voice message referring to which performance decrements have been detected may be provided. For example, if glance behavior is above glance safety threshold standards (e.g. EU recommended 4 glances or 2 second single glance duration, US AAA recommended 10 second total glance duration), then the message "Visual Distraction Detected" or "Eyes off road extensively" can be issued. If steering is deviant during secondary task glance behavior, then the message "Inconsistent steering during visual distraction" can be issued. If lane keeping is deviant during secondary task glance behavior, then a message such as "Inconsistent lane-keeping during visual distraction" can be provided. If large_speed_reduction is detected during secondary_ask_glance_behavior, then a message such as "Large speed reduction during visual distraction" can be issued. If multiple_causes are detected, then a generic message such as "Visual distraction detected" can be issued. If control task intrusion is detected during secondary task glance behavior, during different road types or different demand levels, then a corresponding warning is issued. The form(s) of the warnings can include a driver recorded or provided message, a seat vibration in a front part of seat or gaze redirection as described hereinbelow.

Figure 13:
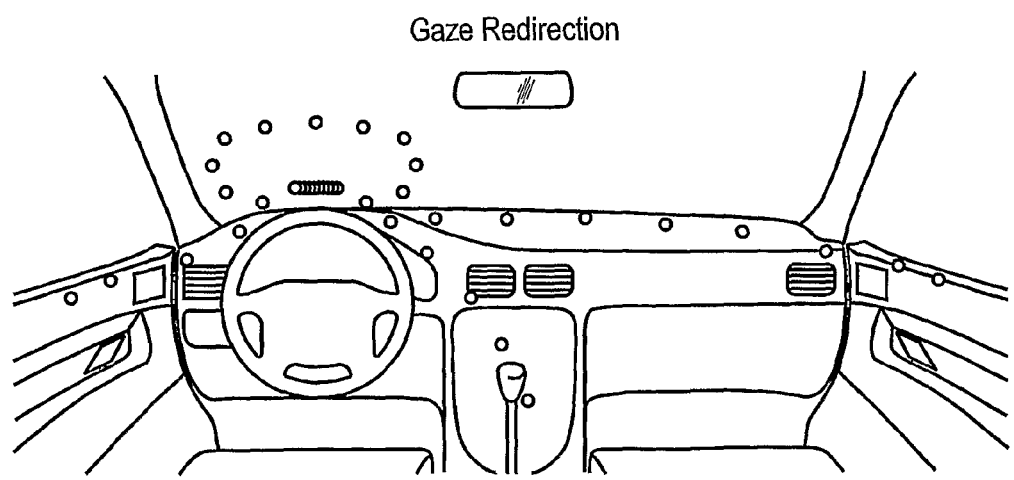
FIG. 13 depicts an exemplary embodiment for driver gaze redirection.

The present disclosure also includes a new concept of "gaze redirection" that is illustrated in FIG. 13. Therein, an interface directs the driver' eyes to the forward driving scene (i.e.; through the front windshield) if driver distraction is detected. Exemplarily, a wave of light following one or more of the three LED "lines" (left, center, or right) will be initiated depending on where the drivers' gaze detected. After a wave of light, a large circle may optionally light up and then the central line of LEDs will light up; each purposed to more clearly focus the driver's attention where needed. The exact placement and timing of the several LED lights is not critical, nor is the color, in fact, the timing may be subliminal; that is, so fast that they are not consciously perceived. Alternatively, the appropriate lights may be first slowly flashed and the driver evaluated by the system to determine if corrective behavior has taken place. If not, the flash timing, as well as light intensity may be increased.

The set-up menu for distraction feedback may have exemplary logic as shown below:

HMI Component Option(s) (1) Continuous distraction feedback on/off (2) Safety

Voice message on/off threshold Performance specific message on/off based Default/multiple cause message on/off distraction User supplied message on/off warning Seat vibration on/off Gaze redirection on/off.

In another aspect, the present invention incorporates the concept of workload management with driving demand estimation derived from visual behavior of the driver. In general, the concept of a "workload manager" is a prioritization system that categorizes information and potentially delays presentation of the information to the driver until his or her workload is sufficiently low to avoid risk associated with the information's reception. The interfaces of integrated, in-vehicle information systems can be adapted to ensure that proper attention is being given to the driving task. The output from the distraction management algorithms referenced herein can be used as input to workload managers.

Workload managers of the type disclosed herein accurately measure driver workload using the driving demand visual activity measure of driving demand. Exemplarily, this is a non-bodily contact, on-board measure of how "visually active" a driver is; that is, head and eye movement (rotation) variability.

One aspect of the workload manager is to pause dialogue of audible conversation or information. As examples, this includes system-initiated or auto-initiated information (e.g. text-to-speech email and non-critical navigation system information) and randomly-initiated spoken dialogue (e.g. incoming and outgoing telephone conversations) can be paused during periods of high visual activity.

As an example, a series of emails can be being delivered to the driver, for example, ten new emails from memory that are being "read" out loud by a text-to-speech system. During the course of such audio transmission, a period of high driver visual activity is detected by the management system, in response, the system pauses the audio transmission to avoid increasing the driver's attention load beyond pre-selected levels; such levels exemplarily corresponding to attention loads beyond which driving capabilities are compromised. Optionally, the management system can include an audible indication to the driver of such interruption via a tone or the like which may also serve as notice to the driver of the high attention load condition. The audible transmission can be resumed based on driver initiation or system initiation that is dependent on the system's detection of a sufficient reduction in attention load to a pre-selected level exemplarily corresponding to safe conditions for driver receipt of such audible information.

In another aspect, continuous and/or post-trip attention load feedback is enabled via the disclosed management system. This aspect has been enabled pursuant to the fundamental human behavior characteristic commonly referred to as the feedback principle; such principle generally holding that feedback enhances performance. This is true for both task/skill learning (e.g. learning to drive safely) and for job motivation. As appreciated hereinabove, drivers are typically poor judges of their own performance. The degree to which direct, accurate, immediate, and continuous information on task/skill performance is available is a key element in enhanced driver performance and motivation. Attention feedback constitutes a form of intrinsic driving feedback that has heretofore been otherwise unavailable to the driver. The approach is one of positive behavioral adaptation and lifestyle change rather than imminent collision warning. For example, some researchers believe that the main mechanism for increased alertness is "decision influence." The concept of decision influence stipulates that information of this nature (driver attention load and state-of-alertness) will influence a driver' decision about whether to stop for rest, drink coffee, reduce alcohol consumption or change other such behaviors.

An objective of attention feedback is thus to encourage positive behavior change over one or more of a plurality (multiple) of time-frames, for instance: (1) immediate (e.g. short-term compensatory behaviors like changing posture or aborting a complicated task); (2) trip (e.g. stopping for a nap, turning off mobile phone); (3) day-to-day (sleeping more after a low attention day, removing video screen from front seat), (4) and long-term (adoption of a different sleep lifestyle or distraction attitude). This feedback increases driver self-awareness of inattentive behavior and enables better self-management.

Two main feedback types are considered. The first is continuous in-vehicle feedback that provides the driver with real-time attentive performance information, for example information presented while driving. This information is communicated in a way that, in itself, does not jeopardize safety. The concept is to provide a sort of attention-meter, alertness meter (alert-o-meter), or safe/unsafe driving performance meter. The second feedback type is post-trip feedback that provides the driver with more detailed attentive performance information once driving has stopped.

Saving post-trip feedback "to file" further allows fleet-based safety feedback to focus on source behaviors as opposed to outcome measures such as accident incidents. One option, perhaps contributing to driver acceptance, is the provision of a tiered system, in such a tiered system, drivers have continuous access to data, fleet managers have access to summarized data, and regulating agencies can be granted access to summary data. Therefore, in the instance of fleet drivers, the invention can be better enjoyed as a helpful tool, without necessarily having to induce driver apprehension about employer-reporting characteristics.

Figure 14:
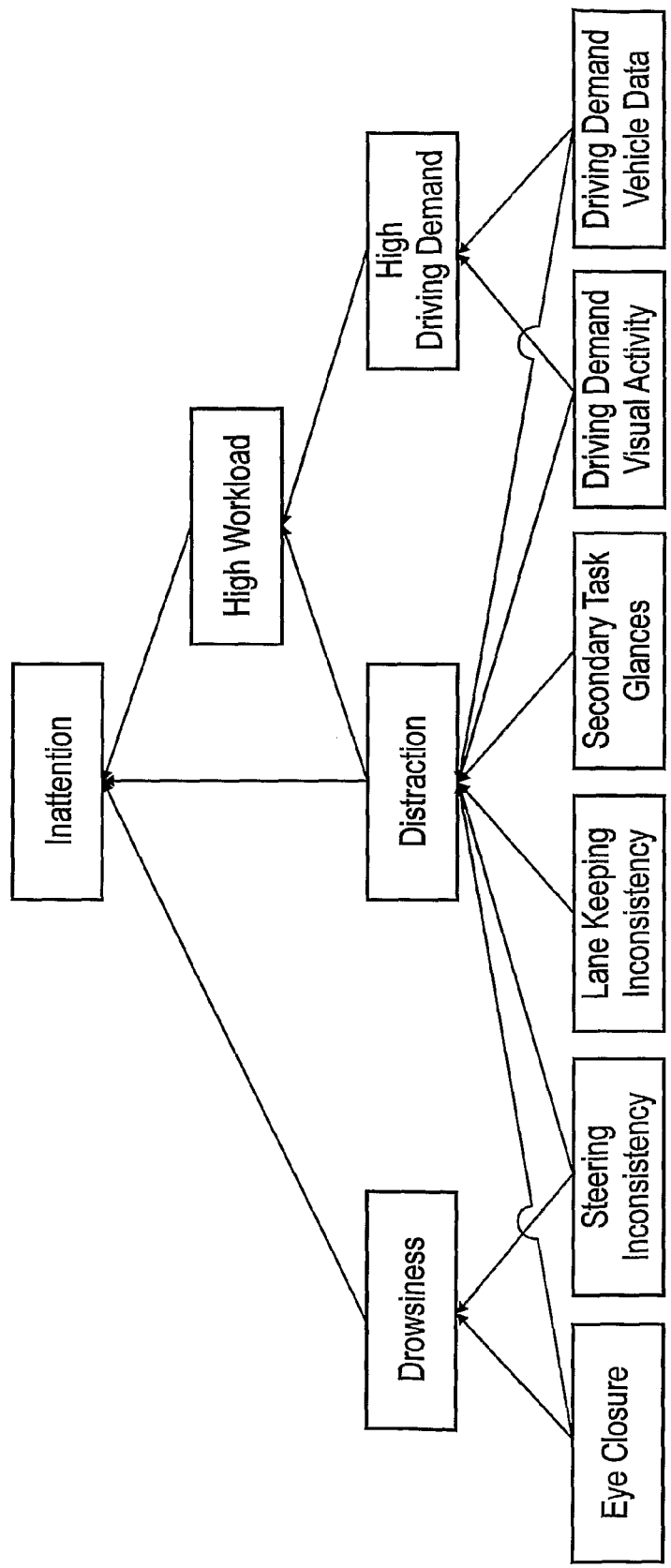
FIG. 14 diagrammatically illustrates interaction of constituent components of driver inattentiveness.

To be able to give attention feedback, the management system has to be operationalized. Inattention may be seen as being comprised of drowsiness/impairment, distraction, and high workload factors. Therefore, and as illustrated in FIG. 14, an integrated model considering each type of inattentiveness is preferred. Therein, one system model configured according to the present invention is shown that can selectively consider driver inattention, workload, and personal characteristics such as drowsiness and distraction.

In another aspect of the present invention, unique ways are provided for displaying various information or feedback to the driver. In the instance of continuous attention-feedback, FIGS. 8(a)-(c) demonstrate various "active" graphical displays for displaying real-time driver information that has been sensed or generated by the management system. As an example, the display can be of a "generic" or synthesized attention feedback quantity such as the level of attention/inattention as a combined measure of drowsiness, distraction, and workload. In the instance of FIG. 15(a), a simple stack of lights with no trend information is exemplified. In the instance of FIG. 15(b), an "aircraft radar type" display is utilized in which a box is positioned around the current level and trend information in the form of "fading out" is enabled. FIG. 15(c) demonstrates a histogram in which instantaneous "real time" information is shown as an elongating/retracting bar (relatively wide) on the right, with aggregate statistical values (average, median, and the like) for periods of preselected duration represented by the more narrow bars on the left. In this manner, trend information is demonstrated. In the illustrative example of FIG. 15(c), five previous periods are represented. It should be appreciated that any previous periods may be displayed according to the control logic for the display and memory capacity.

Figure 17:
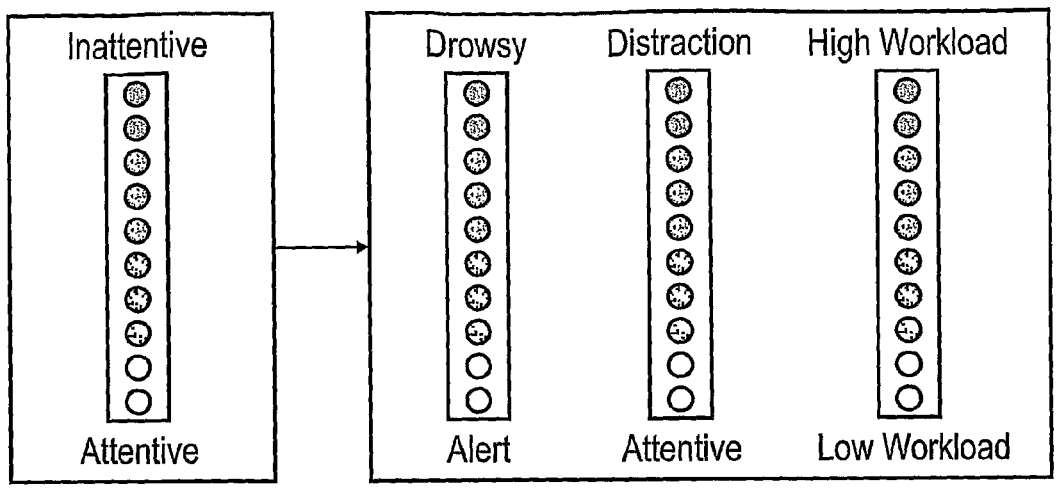
FIG. 17 provides an illustration of an exemplarily formatted explanation of the basis for the detected increased workload/inattention level.

In another aspect, the present invention also provides real-time driver feedback in a comparative format against an indication of an optimal level of attention. An exemplary embodiment of such a display is illustrated in FIG. 16 where a driver may observe his or her degree of distraction or overload relative to optimum attentiveness.

in still another aspect, the invention may be used to measure detected periods of driver inattention, with notification of the state provided. The driver may then "ask" (e.g. by touching a screen, for instance) what the problem was and receive an explanation of the basis for the detected increased workload/inattention level. Such feedback can exemplarily be provided in the form of verbal messages and/or graphically as shown in FIG. 17. Therein, three graphic representations of drowsiness, distraction, and workload are depicted on the right, and a combination of the effects is demonstrated on the left where relative driver attentiveness is indicated.

Figure 18:
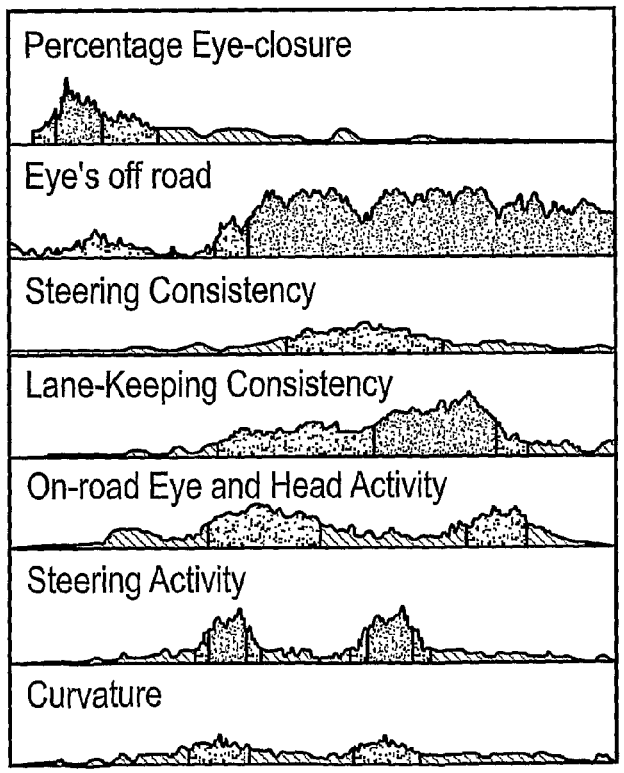
FIG. 18 provides an exemplary illustration of on-screen post-trip feedback.

As explained above, the aspect of trip-reporting can be highly advantageous for the driver' learning and behavior modification. Therefore, inventive ways to provide on-screen post-trip feedback are disclosed and exemplarily illustrated in FIG. 18. In this illustrative example, a menu choice from a display screen has been selected for post-trip feedback and the associated display of such measured characteristics as percent eye-closure, steering consistency and the like have been displayed in a historical format. Of course, this same information can advantageously be logged for later analysis and use.

The driver capabilities that have been discussed above can also be utilized for distraction adaptation of other vehicle systems such as forward-collision, rear-collision and lane-change collision warning (FCW, RCW and LCW)_systems. Rear-end collisions account for approximately twenty-eight percent of automotive crashes. Because driver inattention is a contributing factor in more than sixty percent of these collisions, collision warning and avoidance systems are important tools for reducing crashes and saving lives. One objective of the present attention management systems is to detect the co-occurrence of inattention and safety critical events in the traffic environment; for example, sudden braking of a lead vehicle and driver eyes-off-road conditions. Two examples of this can be used as visual behavior information to adapt forward collision—and lane change—warnings.

Integration of detection of quantified secondary tasks (e.g. by detecting button presses or eye movements) greatly enhances the collision warning system by dynamically adjusting the collision warning threshold according to whether the driver is engaged with a potentially distracting device or other type task. For example, the collision warning system could generate a warning earlier if it is detected that the driver is involved in a cellular telephone conversation. An early collision warning helps the driver react more quickly and avoid more collisions compared to late warning, or no warning at all. If the driver is inattentive with respect to a certain aspect of the driving task, for example looking away from forward when a likelihood of forward collision is detected, or has not looked sideways when a possible lane change collision is detected, then warnings of such conditions are initiated earlier. Studies have shown that even a one second earlier warning when drivers are looking away is highly effective for avoiding collisions.

If it is detected that the driver is attentive, then the warnings can be delayed or even cancelled, A delay in warning presentation allows more time for the forward collision and lane change warning algorithms to more certainly ascertain that a warning is needed, thereby reducing false alarms. Still further, driver cancellation wherein the driver chooses not to have collision warnings active when looking at the road or side mirrors would also eliminate annoying false alarms.

Figure 19:
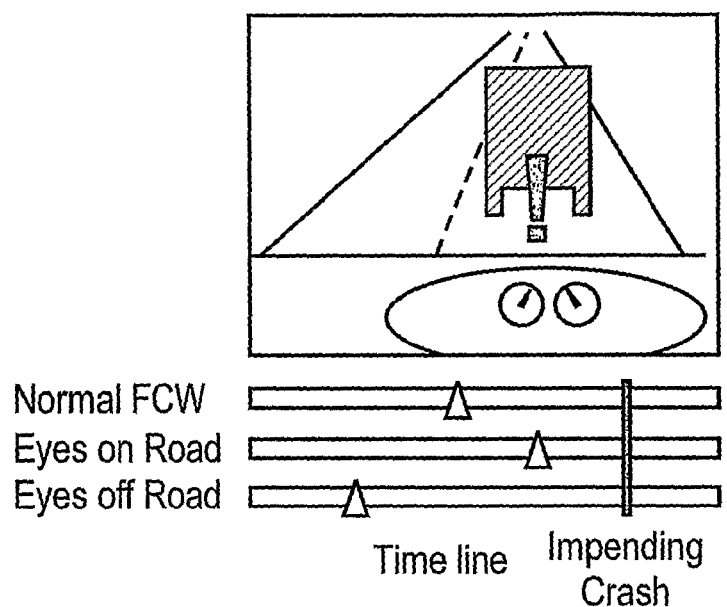
FIG. 19 provides an exemplary illustration of a heads-up or screen display warning for forward collision situations.
Figure 20:
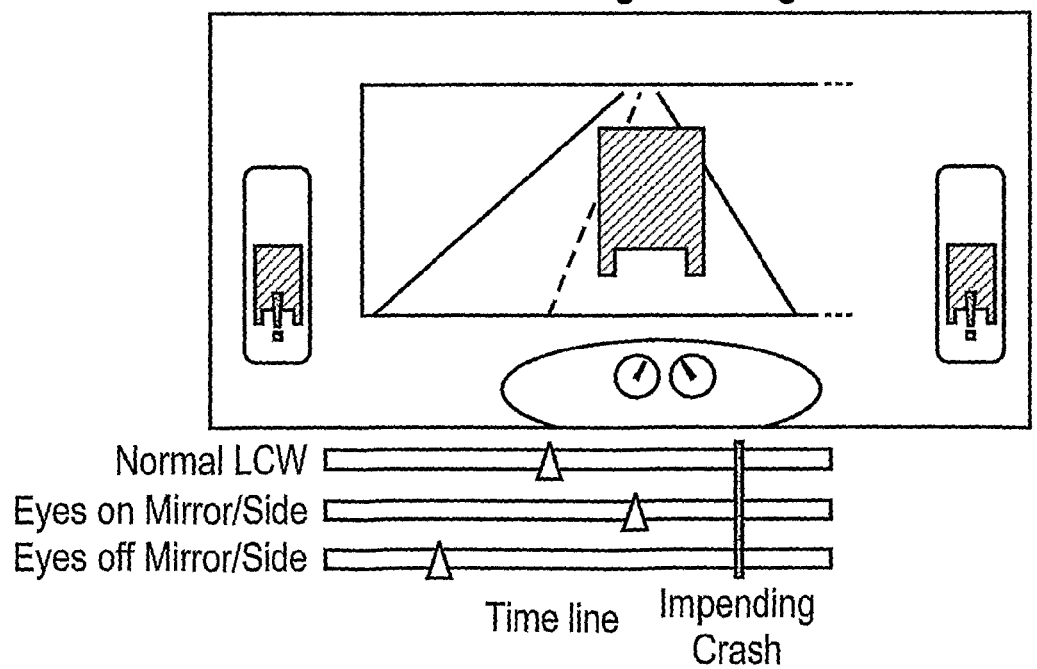
FIG. 20 provides an exemplary illustration of a heads-up or screen display warning regarding lane-change collision situations.
Figure 21:
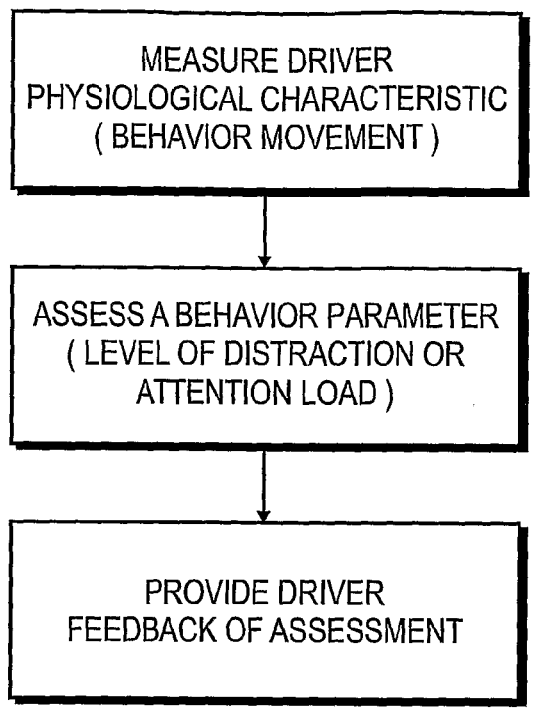
FIG. 21 provides an exemplary flow chart for a system and method conducted according to the present invention in which a measure is made of a driver physiological characteristic. In another step, a behavior parameter is assessed such as level of driver distraction or attention load, in still another step, feedback regarding the assessment is made to the driver.

As an implementation strategy, in a first stage, such warnings may be "soft," but increasing in intensity as conditions worsen and a crash becomes more imminent. In the instance of forward collision warning, a heads-up or screen display warning may first be called up, but later being joined by an audible warning sounded as crash conditions intensify. An example of such a warning and its control parameters (which may or may not be displayed to the driver) are depicted in FIG. 19 regarding forward collision situations and FIG. 20 regarding lane-change collision situations.

The detection features described hereinabove with regard to driver characteristics may be utilized in other environments and for other purposes than expressly described. The detection features may also be integrated for employment in other in-vehicle systems. For instance, as a passive safety feature, a "smart" airbag may be enabled that detects when the driver'/passenger head is not in a proper position to receive a deployed airbag. Responsively, deployment of the airbag may be modified to accommodate the sensed head position.

In another capacity, sensed behavior could be used to identify the driver, or at least rule out that an authorized driver is behind the wheel thereby facilitating theft protection. The head and eye sensors could also be used to automatically configure mirrors, seat positions and the like. Mouth tracking can be used to enhance speech recognition accessories. Filters for oncoming headlights can be adapted, as can displays for the driver based on eye position and motion.

In the course of describing the present invention(s), equipment and procedures are identified that are suitable for both simulated environments, as well as for on-the-road trials. Both standards (SAE and ISO) are, however, based on a video technique utilizing, for example, camera and recorder, with manual (off-line) classification of fixations and saccades performed by human raters. The manual video transcription is a time consuming and potentially unreliable task. Therefore, an automated method such as that upon which the present inventions are based, is preferable. The incorporation and exemplary reliance on the ISO/SAE-type measures can be advantageously relied upon using any system that classifies eye movement, either manually or automatically.

Following, three subsections of basic ocular segmentation are described, as well as two groups of measures. Basic ocular segmentation divides eye movements into the smallest quantities measurable with available eye-tracking systems. These eye-movement "bricks" represent a base from which all glance-based and statistical measures are derived. In summary, they include: (1) saccades that define the rapid movement occurring when looking from one area of interest to another; (2) fixation which addresses alignment or steadiness of eyes position so that the image of the target upon which fixation is being made falls on the fovea for a given time period; (3) eye closures where short duration eye closures are referred to as blinks and long eye closures may be characterized as drowsiness.

Figure 22:
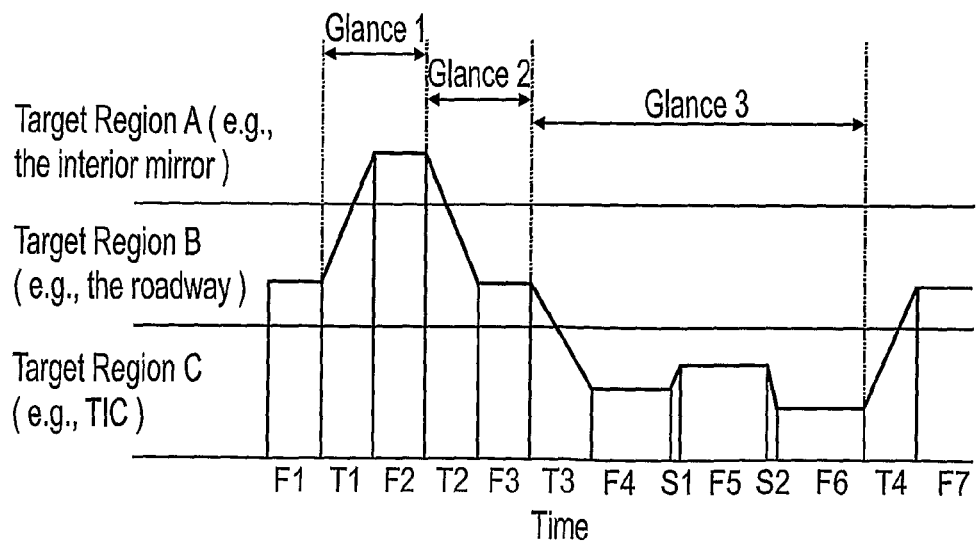
FIG. 22 illustrates eye movement components that constitute glances.

In order to comprehend the measures utilized in the ISO/SAE documents, it is important to be familiar with the definition of a glance, which by SAE standards, is considered as a series of fixations at a target area until the eye is directed at a new area. For example: if a driver initially looks straight-ahead (on the road) and then to the radio, fixating first on the display and then the volume control, he or she performs two fixations (not counting the first one straight-ahead) and two saccades, all of which compose one glance. The glance is initiated as the first saccade away from the road begins (this saccade is called a transition) and terminated as the last fixation at the radio ends. FIG. 22 provides a graphic illustration of the components of a typical driver three-glance series. Therein, fixations, saccades and transitions are quantified as components of the several glances.

All glance-based measures are derived from these definitions and are to be considered a "higher-level" description of eye movements that constitute the "bricks" described in the previous section. These measures reflect different properties such as time-sharing, workload and visual attention demand. The measures defined and utilized in the ISO and SAE protocols are: (1) glance duration defined as the time from which the direction of gaze moves towards a target to the moment it moves away from it. Rather long durations are indicative of a high workload demand in that area; (2) glance frequency defined the number of glances to a target within a pre-defined sample time period, or during a pre-defined task, where each glance is separated by at least one glance to a different target. This measure should be considered together with glance duration since low glance frequency may be associated with long glance duration; (3) total glance time defined as the total glance time associated with a target. This provides a measure of the visual demand posed by that location; (4) glance probability defined as the probability for a glance to a given location. This measure reflects the relative attention demand associated with a target. If calculated over a set of mutually exclusive and exhaustive targets such a distribution can be used to make statistical comparisons; (5) dwell time defined as total glance time minus the saccade initiating the glance; (6) link value probability defined as the probability of a glance transition between two different locations. This measure reflects the need to time-share attention between different target areas; (7) time off road-scene-ahead ("road scene ahead" excludes the rear view and side mirrors) defined as the total time between two successive glances to the road scene ahead, and which are separated by glances to non-road targets; (8) transition defined as a change in eye fixation location from one defined target location to a different i.e. the saccade initiating a glance; (9) transition time defined as the duration between the end of a fixation on a target location and the start of a new fixation on another target location. Since there is very little or no new information during transitions, increased transition time reflect reduced availability for new driver information; (10) total task time defined as total time of a task which is in turn defined as the time from the first glance starting point to the last glance termination during the task.

Non-glance based measures are all other measures that can be calculated other than those that are defined in the ISO/SAE standards. Two examples include: (1) mean value and standard deviation of fixation position within different clusters, for example, the road scene ahead and a cellular telephone; and (2) mean value and standard deviation of fixation dwell-time within different clusters and/or different tasks. These types of measures are interesting when analyzing, for example, normal driving compared to driving during high cognitive load periods such as would occur if a driver were to be involved in a mathematic task.

A general objective of the present invention is to provide automation of the data analysis of eye movements with focus on the measures prescribed in the ISO 15007-2 and SAEJ-2396 methods for measurement of driver visual behavior with respect to transport information and control systems. Exemplary tools utilized in the present automation include eye tracking systems that are otherwise discussed in greater detail herein. Advantageously, the algorithms and implementing systems should only require a minimum of human interaction, such as loading/saving data and visual inspection of detected clusters and outliers.

A starting-point for the present disclosure was a showing that an automated analysis is possible using available sensing system; the particular study revealed high correlations on all measures. In this example, the signal was filtered using a sliding thirteen-sample median window filter to reduce noise, eliminate some outliers and blinks. A velocity threshold algorithm was developed to differ saccades from fixations (smooth pursuits were considered to be fixations) and a manual delimitation of clusters provided a base for glance classification. The procedure required significant operator input and attention; for instance, the signals had to be filtered, and outliers, short fixations, and other artifacts were manually identified. As the inventions have evolved to the point of the present disclosure, these operator-time intensive procedures have been eliminated.

Originally, the median filter width was not optimal for all subjects; the length needed to stand in proportion to the noise level. Responsively, different filter types and parameters were utilized. Also, it was learned that the velocity algorithm was sensitive to noise. Hence, the threshold was set to 340 degrees per second that is substantially above saccadic start and ending velocities. To compensate for this, the two samples preceding and following a saccade were also marked to have saccadic velocities. Since saccades vary in amplitude and peak velocity, so does their acceleration. Thus, this precursor method provided a good approximation of saccade beginnings and endings, only. Therefore, an objective of the presently evolved invention is to provide a robust technique for saccade/fixation identification that is more accurate.

Furthermore, a need for a clustering technique that automatically identifies glance target areas and glances was identified. An objective was to eliminate outliers and other artifacts in an automated way, other than by the traditional means of human rating.

An understanding of the origin and properties of the data disclosed herein is important when designing detection algorithms. Therefore, the available data and the technical platforms used to obtain that data are described.

Figure 23:
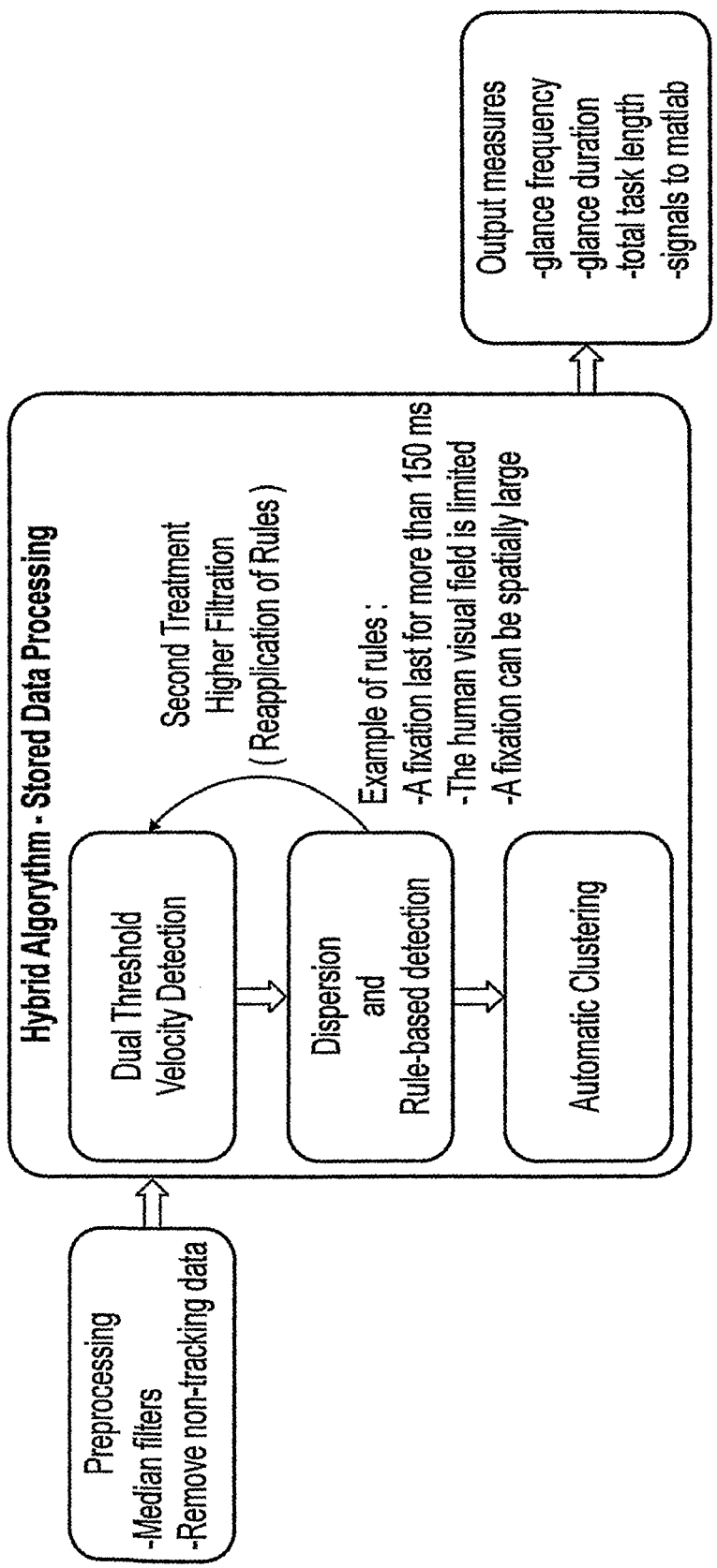
FIG. 23 is a diagrammatic illustration of and off-line hybrid algorithm.

Regarding the invention(s) at hand, FIG. 23 of the accompanying drawings provides a general overview of an exemplary off-line analysis algorithm. Raw eye movement data is input at the upper left-hand box where pre-processing is performed. Exemplarily, such pre-processing includes a median filter that subdues noise, artifacts and blinks. Also, all non-tracking data is removed at this functional station.

The large, intermediate box, represents an exemplary algorithm that as illustrated, is a hybrid treatment between two commonly used data-treatment-algorithms (Dual Threshold Velocity Detection and Dispersion and Rule-Based Detection). As indicated in the right-portion of the intermediate box, the applied ocular rules are based on known limits or parameters of certain aspects of ocular behavior such as minimum length (with respect to time) of a fixation generally defined by human ocular capabilities. The bottom box inside the hybrid algorithm represents an adaptive clustering algorithm that clusters fixations, based on one or more characteristics thereof, and in practice makes the clusters tend to "float" into place as the number of sampled glances increases.

Figure 24:
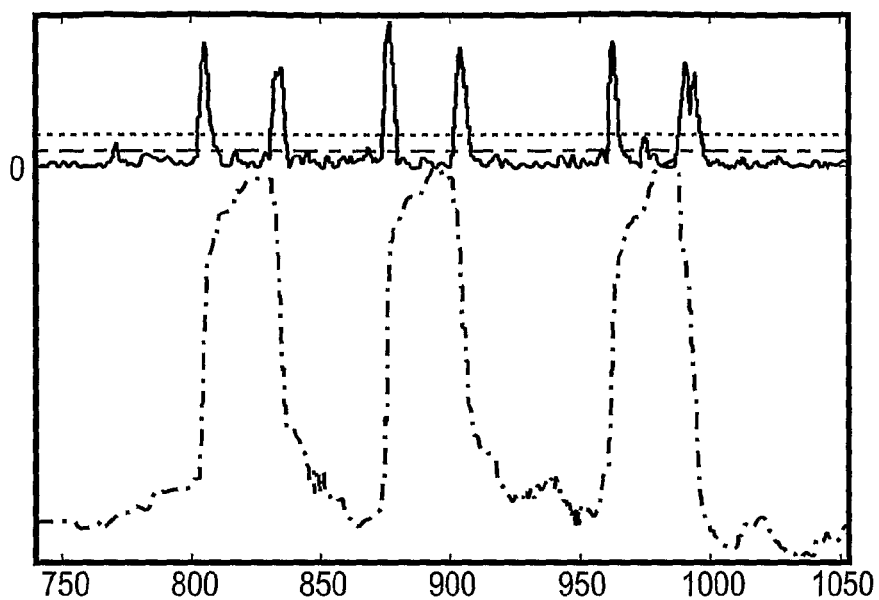
FIG. 24 is a graphic view demonstrating threshold rules that define fixations and saccades.

The Dual Threshold Velocity Detection algorithm represented by the upper box inside the hybrid algorithm is based on eye movement velocity (degrees/second). Referring to FIG. 24, a high threshold (top, flat, dotted line) differentiates fixations between those that have low velocities, from saccades. The lower dot-and-dash curve represents an actual eye-movement, illustrated in one dimension, and the solid peaked curve represents the derivative thereof, or eye-movement velocity. Once a saccade is detected, a low-threshold (short-and-long dashed line) is applied to determine the start and ending points. The reason to use two thresholds is to avoid noise triggers caused by saccade detection. It should be appreciated, however, that as noise increases, so does the error in this protocol.

In addition to saccade detection, a dispersion protocol is used in conjunction with applied ocular rules. The rules determine when detected saccades and fixations are not natural; that is, their defining data is in some way outside of accepted characteristic parameters for the assigned classification (saccades and fixations).

Examples of such rules could be that a fixation has to last for more than 150 ms and a saccade is measured by some predetermined shorter period. Also, a saccade cannot return to the same area from which it started. Whenever these rules are applied to change a fixation into part of a saccade or a saccade into part of a fixation, the dispersion algorithm determines how the situation will be handled. For example, if two successive fixations at the same target are detected with a 60 ms saccade in-between, it can be deduced that it might have been noise that triggered the saccade detection. Whether it is noise or not is determined by the dispersion protocol. If the two fixations are within a certain distance from each other (the dispersion threshold), they are a part of the same fixation, and the saccade is changed into part of that fixation, otherwise it is most probably a correct detection.

Figure 25:
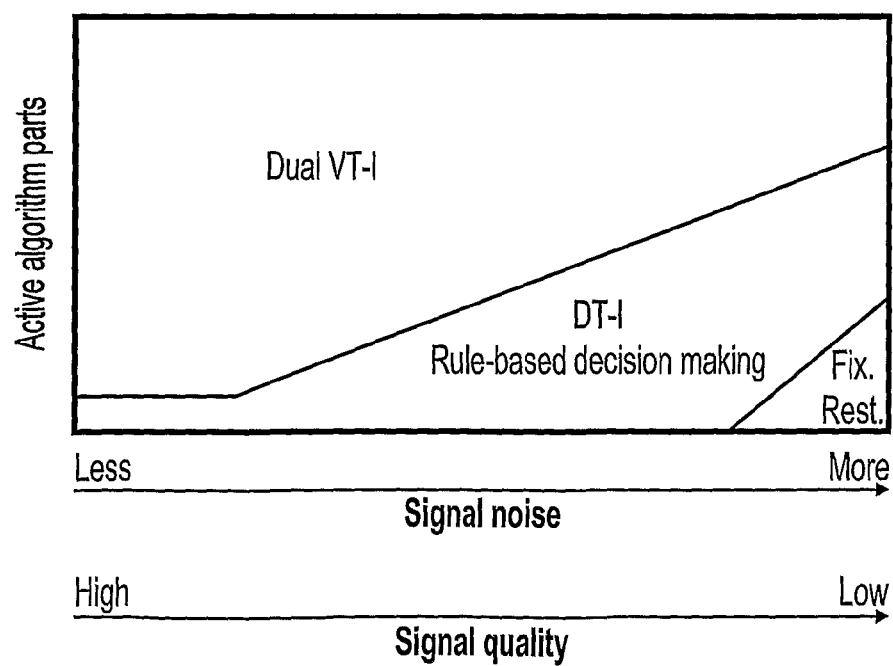
FIG. 25 is a diagrammatic illustration demonstrating analytical tool choice based on signal noise quantity.

A main precept of the hybrid algorithm is that it automatically biases the "decision" as to which treatment algorithm (or parts thereof) will be applied to the data based on the current noise level. As depicted in FIG. 25, relatively noiseless tracking data that is of higher quality will be treated predominantly using Dual Threshold Velocity Detection. The presence of an average or intermediate amount of data noise/quality increases the influence of the Dispersion Detection treatment of the data. Finally, and as represented at the right-side of FIG. 25, fixation restoration can be affected when the data is very noisy and of low quality. Usually such low quality or noisy data will only be a transient effect and not apply to the overall data stream. In the event that portions of the data are of such low grade quality, restoration of that portion takes place by applying a stringent filter to the corresponding data to see if it can be "calmed" (smoothed) enough to discern the behavior underlying the extreme noise. The restoration is accomplished by a "substitution" of the heavily treated portion when the more stringently filtered output passes the "validity" rules that the more mildly filtered data failed.

When the detection of all fixations and saccades has been finished, the data is input to the clustering algorithm that identifies glances based on the outcome of a performed cluster analysis, exemplary details of which are developed more fully hereinbelow.

Figure 26:
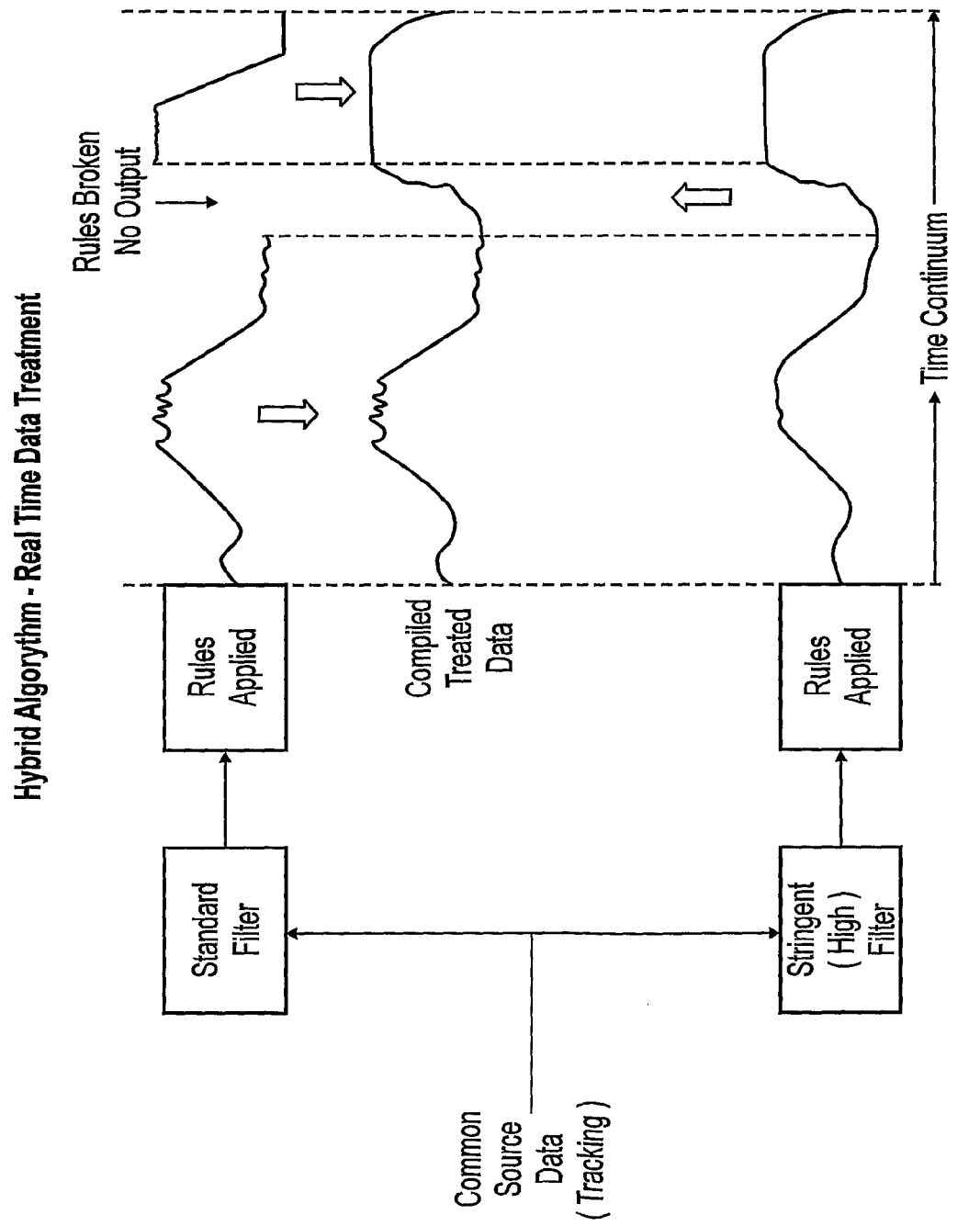
FIG. 26 is a diagrammatic illustration of and on-line hybrid algorithm.

FIG. 26 depicts a hybrid algorithm that is utilized to perform real-time tracking data treatment. Raw tracking data, typically in any data-stream form, is obtained from a sensory system regarding head and/or eye orientations and movements. Because the processing is taking place on a real-time basis, the luxury of being able to recycle the data for any further filtering pass if it fails to meet rule criteria is not enjoyed. Best possible data must be made available at all times. Therefore, the real-time hybrid algorithm essentially runs two tandem treatments of the same data. As depicted in FIG. 26, the source data is treated above using a standard filter and simultaneously, in parallel below, using a more stringent filter. At the same time, the differently filtered source data is treated with a rules set. Usually the rules that are applied to each filtered data stream are identical, but each might be tailored depending upon the respective filtration characteristics.

From each of the two rule treatments, a data stream is produced. As may be appreciated from FIG. 26, the character of the two outputted, filtered streams is different. Preferably, the standard filter has been quite mild with respect to smoothing the data, and the rules set applied to the data stream endeavors to determine whether or not a valid fixation or saccade is occurring. If the rules cannot be met, then no data stream is outputted. This blank in the data may be appreciated in the top, right-hand corner of FIG. 26. It is possible that simply too much noise is present in the portion of the stream of data that fails to meet the applied rile(s).

During this entire time, the data is also being processed with the stringent filter as described above. Typically, the stringent filter does significantly "smooth" the data in an effort to remove noise. The outputted data may be less sharp, but when the same rules are applied to the more highly filtered data that corresponds to the blank zone, non-rile compliant standardly filtered data portions, saccade or fixation characteristics are discernible. When that is the case, the rules are passed, and valid characterization of the data is obtained. This rile-passing portion of the highly filter data corresponding to the blanked-out, rule breaking lesser filtered data zones is merged into the outputted stream that has passed after standard filtration. This is illustrated as the compiled treated data stream in FIG. 26.

The compiled data stream, while possibly having short blank portions where neither of the differently filtered data streams passed the applied rule(s), is substantially contiguous if the source data is of acceptable quality (lack of noise) in a general sense. That is to say, very low-quality data will never be acceptable, and cannot typically be filtered or treated to be made acceptable. But where the source data is generally acceptable except for certain substandard portions, the exemplary hybrid algorithm for treating real-time tracking data produces an outputted stream of compiled data composed of classifiable fixations and saccades suitable for further processing, such as cluster and density analysis as is described in greater detail herein.

Figure 27:
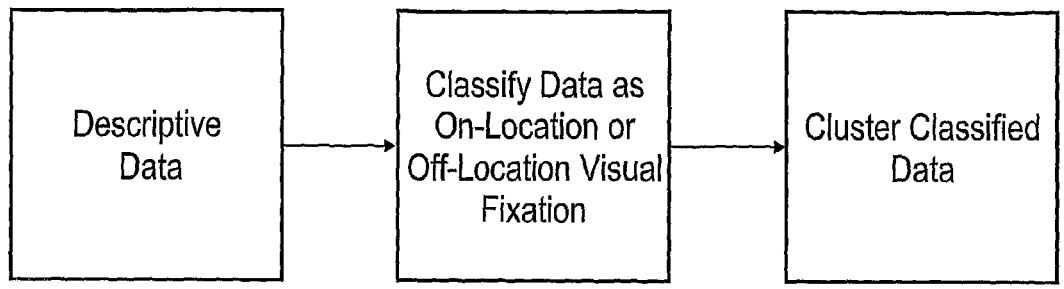
FIG. 27 diagrammatic view of an arrangement for classifying and clustering on-location and off-location data.

FIG. 27 provides a representative schematic of an algorithm relating to the descriptive data collection, on-location or off-location visual fixation classification, and clustering of the classified data.

A location can be any location of interest, for example a location may include: the road center, a location behind the driver, a location to the left or right of the driver, a rear view mirror, a side mirror, a center console, a car accessory (e.g. radio, window switch, navigation system), a personal accessory (e.g. cell phone, PDA, laptop), or a passenger (e.g. children in car seats or back seat). The above list is not all-inclusive and is provided to show just a few examples of location. As seen from the examples above, the location need not be fixed, but can change with time, for example when the location is a cellular telephone or PDA the location changes with time when the user dials the phone, answers the phone, checks caller ID, checks incoming messages, or sends outgoing messages.

in one configuration, the data treatment process begins with a determination of whether a visual fixation can be classified as an on-location or off-location visual fixation. Furthermore, if desired, off-location visual fixations can also be determined based on a determination of on-location visual fixations. For example, if the data is classified as an on-location visual fixation, the data is classified as such. If the data is not classified as an on-location visual fixation, the data may be classified as an off-location data. The main advantage of this simplification is that one can allow for lower data quality during glances away from the road since gaze off-location can be ignored.

Furthermore, this configuration provides for a more robust estimation of behavioural movements than previous solutions that require processing the portions of the signal where the driver looks at eccentric positions, i.e. off-location. For example, behavioural movements that are not classified as on-location visual fixations can be ignored and estimated as off-location visual fixations.

As a result, the present configuration lowers the demand on the technology and allows for simpler and cheaper measurement devices. For example, fewer and less technologically advanced measurement devices could be used to reduce costs of implementing the system. Likewise, less powerful processors could be used to process the information obtained from the measurement devices.

Figure 28:
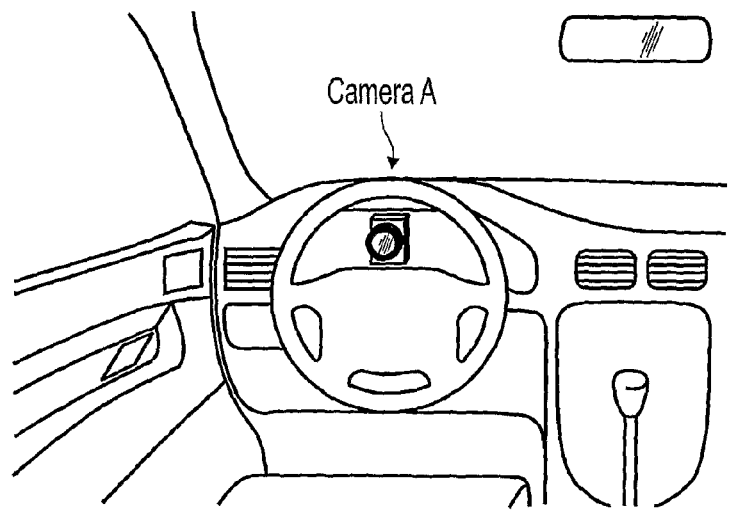
FIG. 28 is a perspective view taken inside a vehicle toward the instrument panel where a single tracking camera or monitor resides.

Only the area where measurement devices provide the optimal performance is regarded, thus high quality measurements are assured. For example, measuring road-center visual fixations may include a measurement device placed substantially directly in front of the driver as seen in FIG. 28. Glances away from the road are inferred from situations when the driver does not look on the road. In another example, measuring rear-view-mirror visual fixations may include a measurement device placed in or around the rear-view mirror.

Figure 29:
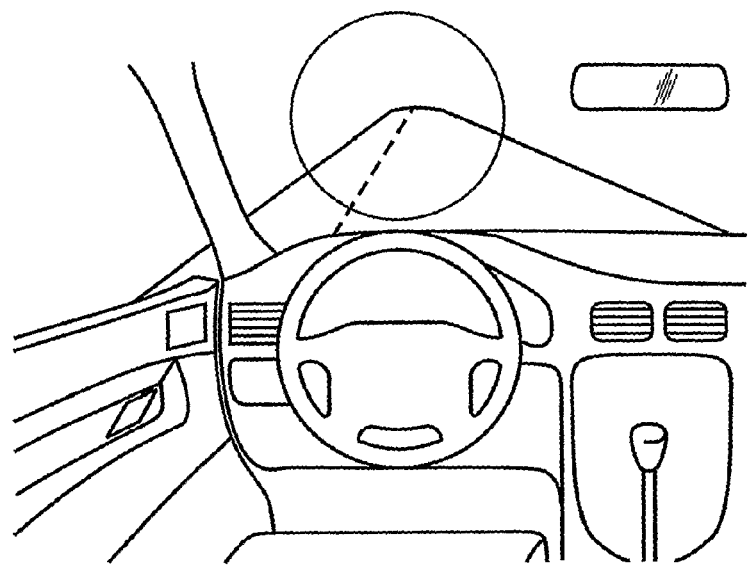
FIG. 29 illustrates schematically the environment of the road-center area concept of the present disclosure.

FIG. 29 provides an instructive illustration of the road-center area concept. It should be appreciated that the road-center concept is applicable to both off-line post-collection analysis of driver awareness, and to real-time driver awareness functions.

The exact location of the RC area is important, as the actual road-center cluster as measured by the measurement devices should be constrained by the pre-defined RC area. Therefore, the location of the RC area could beneficially be adjusted continuously in real-time. A priori information about the relative geometric position of the RC cluster and other clusters in the forward scenery (from the driver's point of view) may also be used to further enhance the estimation of the location of the RC area.

The size and shape of the road-center area may beneficially be adjusted for its intended application. Moreover, multiple RC areas may be defined in an overlay fashion when different visual behaviour correlating to different road characteristics is desired to be measured with high sensitivity, and when specific functions are to be realized. For instance, a large RC area is defined and used by a safety-critical real-time application that needs to know for sure when the driver is positively looking away from the road. Another application is simultaneously interested in off-road glances but uses a smaller area in order to capture more of the off-road glances.

The following Table presents a summary of ISO measures and the corresponding RC approximations:

| Measure (Eye, Head, 6DOF, Body) | Short Name | Definition | Corresponding ISO 15007 measure (Eye, Head, 6DOF, Body) |
|---|---|---|---|
| Non-RC glance frequency | NRC_GF | The number of glances away from the RC during an interval of interest | Glance frequency |
| (Mean) Non-RC glance duration | NRC_GD | The average duration of the non-RC glances during an interval of interest | Mean single glance duration |
| Number of non-RC glances longer than 2 seconds | NNR_2 | The number of non-RC glances longer than 2 seconds during an interval of interest. | Number of glances >2 seconds |
| Total non-RC time | TNRT | The total time the gaze is directed away from the RC during an interval of interest | Total glance time |

Most currently available head/eye measurement devices measure head movements more robustly than eye-movements (the head movements are easier to track when the subject looks away from the sensors). In one embodiment of the invention, that head movements may be used provide a better estimation of the direction of the measured eye-movements by simultaneously regarding the direction of the head movements (and thus estimating the likelihood that the eyes move in a certain direction). In another embodiment, the head movements provide the estimation of the direction of eye-movements (i.e. head movements are used as an approximation of eye-movements when the eyes are tracked poorly, or not at all). Head movements can be measured with respect to rotational movements, such as pitch, yaw, and roll; and can also be measured, alone or together with positional movements such as heave, sway, and bob. Together the three rotational and three positional movements are referred to as the six-degrees-of-freedom (6DOF).

When analyzing the 6DOF, the head movement is generally described by three head rotation components (Pitch, Yaw and Roll), and three head translation components according to a Cartesian coordinate system with the axis x, y and z (Posx, Posy, Posz). These six components can be combined to a head movement signal HMOVE that completely describes the head movement.

Preferably, each of the six signal components is pre-processed to remove measurement noise and long term postural changes of the driver. One way to achieve this is to use a high-pass filter to remove the long term postural changes, which by nature are of low frequency, and a low-pass filter to suppress or at least attenuate the signal noise. Both can of course be achieved by an appropriate band-pass filter as well.

After this pre-processing, the global measurement of the total head movement can, e.g., be expressed and calculated as a function of the six degrees of freedom and their first-degree and second-degree time-dependent derivatives according to equation (1.1):

$$HMOVE = \mathfrak{F}\left(Pos_x, Pos_y, Pos_z, \text{Pitch}, \text{Yaw}, \text{Roll}, \frac{\partial}{\partial t}Pos_x, \right. \tag{1.1}$$
$$\frac{\partial}{\partial t}Pos_y, \frac{\partial}{\partial t}Pos_z, \frac{\partial}{\partial t}\text{Pitch}, \frac{\partial}{\partial t}\text{Yaw}, \frac{\partial}{\partial t}\text{Roll}, \frac{\partial^2}{\partial t^2}Pos_x,$$
$$\left. \frac{\partial^2}{\partial t^2}Pos_y, \frac{\partial^2}{\partial t^2}Pos_z, \frac{\partial^2}{\partial t^2}\text{Pitch}, \frac{\partial^2}{\partial t^2}\text{Yaw}, \frac{\partial^2}{\partial t^2}\text{Roll}\right)$$

This general function or model can be chosen and tuned differently for different applications. For example, a global head movement measure could be defined according to equation (1.2):

$$HMOVE = \sqrt{A*pitch^2 + B*yaw^2 + C*roll^2 + D*Pos_x^2 + E*Pos_y^2 + F*Pos_z^2} \tag{1.2}$$

wherein A to F are weighting factors which determine the sensitivity for different types of head movements and thus the sensitivity of the measurement.

In another embodiment, body position could be used be used to provide an estimation of the direction of the measured eye-movements. The orientation of a driver's body may be used to provide a better estimation of the direction of the measured eye and head movements by simultaneously regarding the direction of the body (and thus estimating the likelihood that the eyes move in a certain direction). In another embodiment, the body movement provides the estimation of the direction of eye-movements (i.e. body movements are used as an approximation of eye-movements when the eyes and or head are tracked poorly, or not at all).

Depending on the characteristics of the measurement device, additional signal processing may be required (or beneficial) to handle situations where the on/off location classification becomes incorrect. For instance, blinks may occasionally misinterpreted by the measurement device as looking down. This may be handled in various ways, for instance by applying a filter that ignores glances shorter than a specified length as being too short and thereby unlikely to be real natural glances. This filter may operate on the measured signal or on the binary on-off location classified signal. The filter operation is applicable to both offline and online (real-time) analysis.

Figure 31:
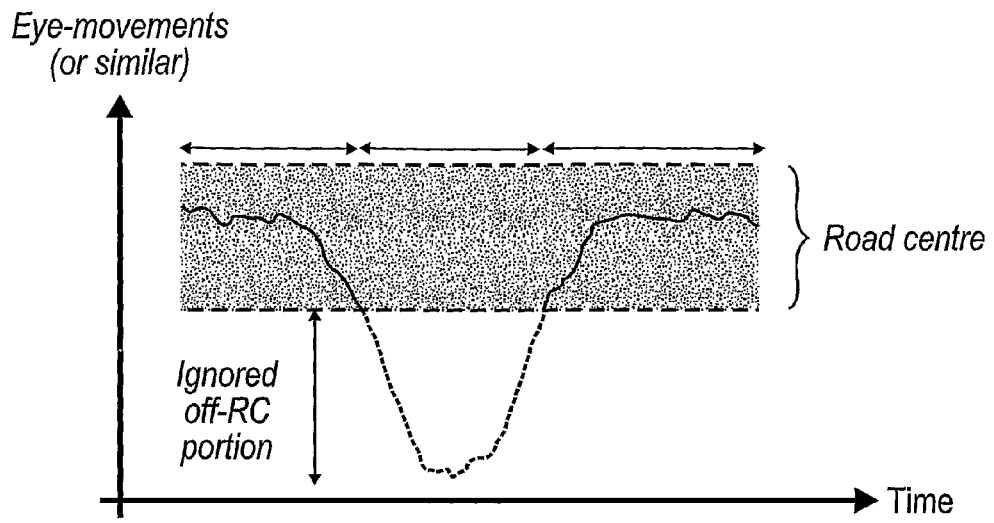
FIG. 31 is a graph plotting eye-movement against time.

Outputted from a remote measurement device is a measurement signal representing the angle, amplitude and/or direction of behavioural movements. Here, these signals are used to make an on/off-location classification of each sample of the signal by applying the methodology proposed above; see FIG. 31.

The result (output) of the classification step is a classification signal which determines in each sample (or unit of time) whether eyes/head/face is directed on or off the road (i.e. the RC region). Operationally, this is done by regarding the Euclidean distance of the measured gaze point (or head/face direction coordinate) in each sample (or unit of time) to the origin of the RC area. If the result falls within the perimeter/boundary defined by the RC area it belongs to the on-RC region and is classified as such, otherwise it is classified as belonging to off-RC.

Occasionally the sensor may loose the tracking of the driver (i.e. no measurement of eye/head/face/body movements). In most cases this will be due to the fact that the driver is looking away from the road and the lost-tracking will be interpreted/classified as off-road glances. Depending on the nature (e.g. duration, magnitude and similar) of the lost-tracking episode it may be necessary to treat the loss of tracking with special filters.

Figure 32A:
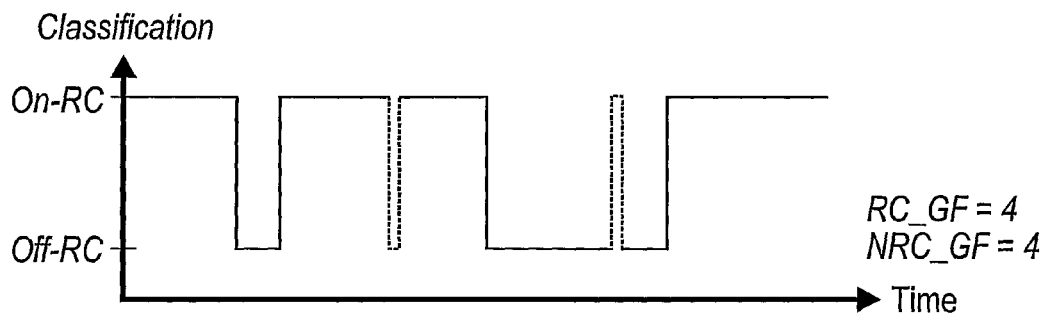
FIG. 32a is an illustration demonstrating non-filtered data.
Figure 32B:
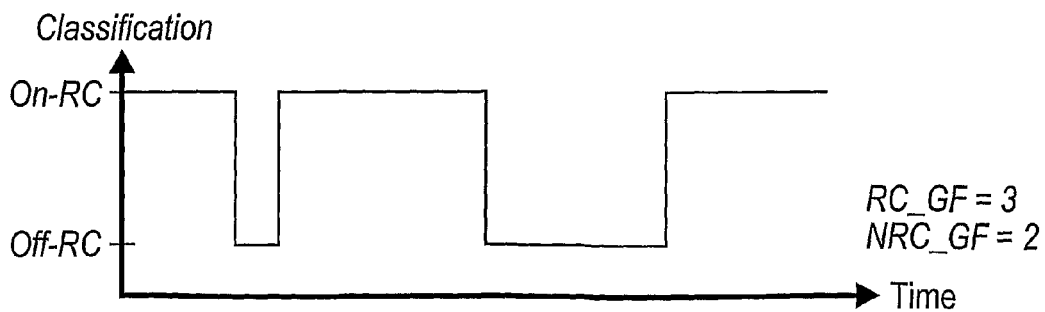
FIG. 32b is an illustration demonstrating data filtering.

FIGS. 32a and 32b demonstrate an example of how the resulting classification can be filtered to remove unnatural (i.e. most likely misinterpreted) glances away from/or towards the location, in FIG. 32a, the original classification is demonstrated, in FIG. 32b, very short glances (shorter than 20 samples) have been filtered or ignored, i.e., re-classified as belonging to the "main" glance.

When the estimated location and the actual cluster formed by the driver's gaze to the location does not align, errors may be introduced in the classification step when gaze is directed on the edge of the location (thus alternating between on/off location although gaze is more or less directed at the same location in space). This is largely managed by the same approach as presented in FIGS. 32a and 32b.

A priori knowledge about the physiology of head and eye-movements may also be used to further enhance the performance of the algorithms. The speed of saccadic transitions and minimum dwell times can supply a physiological basis (or motivation) for determining which glances are correct thus applying a plausibility test on the real-time classification made by the algorithm.

The presented binary on-off location classification can be extended to allow several areas of interest.

After the classification has been made, computing the glance frequency and glance duration measures presented above merely involves counting the number of ON and OFF intervals, respectively, in the classification signal. The glance duration is computed by also regarding the start and end of each continuous segment classified in the same way.

FIGS. 33a and 33b provide an illustrative example of glance behaviour, in FIG. 33a the circle demonstrates where the road-center area is located and graphically illustrates a driver's view of the road at the up-ahead scene. FIG. 33b signifies the same view, but with a time axis added.

In an associated way, the measurement area can be extended by regarding a larger area surrounding the actual road-center area for situations where the measurement device provides a decidedly good gaze or head tracking ability in a larger area. In such instances the extra measurement can provide extra robustness as illustrated in FIG. 34.

Figure 35:
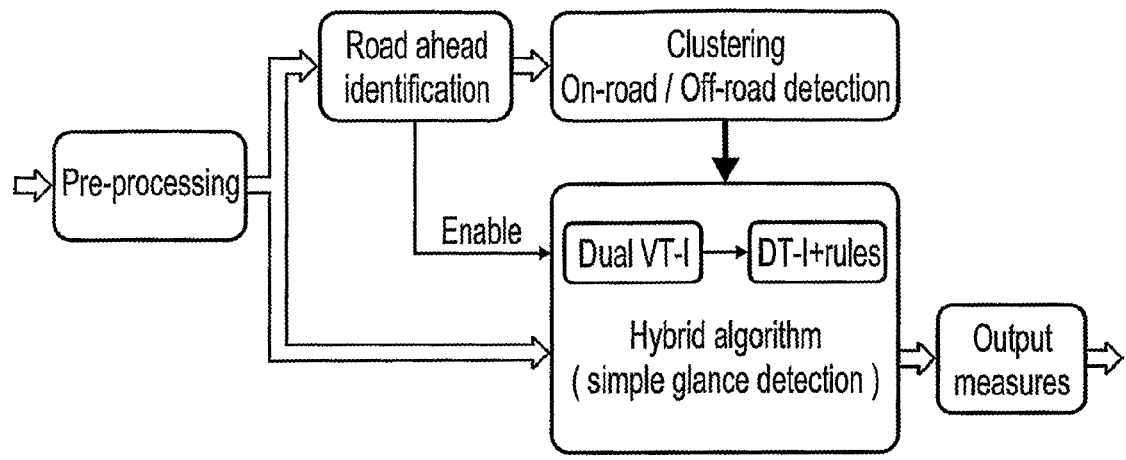
FIG. 35 is a diagrammatic view of an alternative arrangement for affecting realtime analysis of orientation data.

FIG. 35 provides an alternative representative schematic of the real-time algorithm relating pre-processing of data, road-ahead identification, clustering and application of a hybrid algorithm which all together ultimately yield meaningful output measures.

Figure 30:
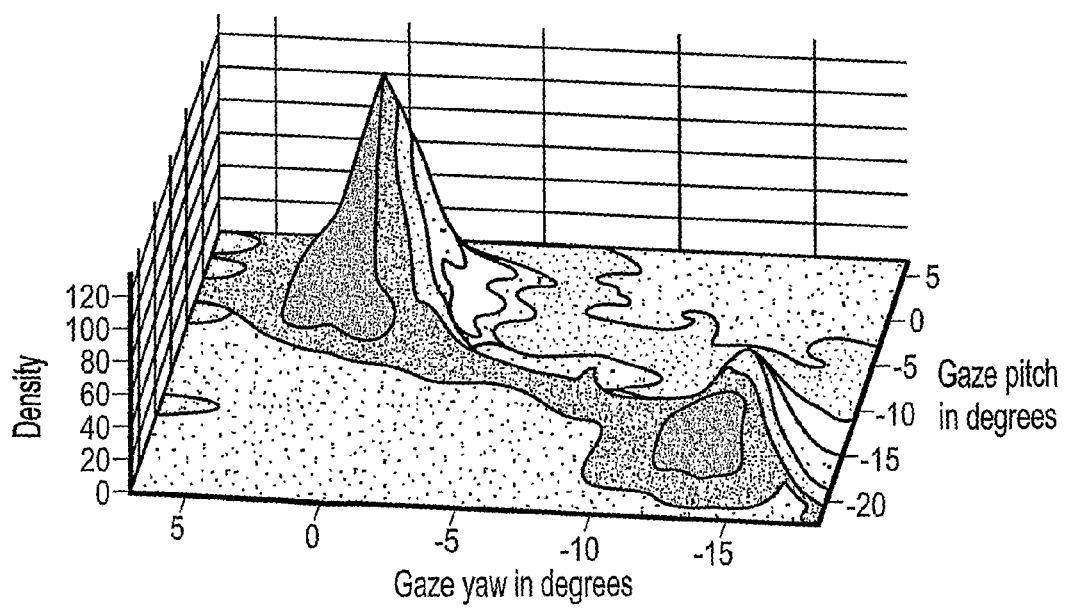
FIG. 30 is a graphic view showing two areas/objects of subject interests based on cluster or density of fact.

In this configuration, the data treatment process begins with an automatic initialization that finds what is defined as the road-scene-ahead. This is done by forming a density surface, where the time the driver looks in a certain direction is described by the gaze density in this area. For example, the more the driver looks at an area the more the gaze density will increase in that area. Most of a driver's attention is likely to be found in what is termed the center of the road-scene-ahead; there will be a "peak of attention" in the center of this area as illustrated in FIG. 30 in this illustration, the plane from where the two peaks rise should be taken to be perpendicular to the driver's face when facing the windscreen. The high peak represents the road-scene-ahead and the lower peak represents a point of concentration. In the mapped example, the subject had been asked to change the language on a Navigation system, which is what the lower peak represents.

During driving, the high (left) peak gradually builds up, and after approximately two minutes, the peak road center (PRC) position is stable. The road center area is defined as the base of this mountain and the peak as its center. The base is considered to be the 95% confidence values calculated based on the approximation that the mountain has a Gaussian shape and the mean value is the peak position. Once this has been done, glances away from the road-ahead position can be detected, and thus attention and driver workload might be calculated using the definition of peak road center as described hereinbelow.

Figure 36:
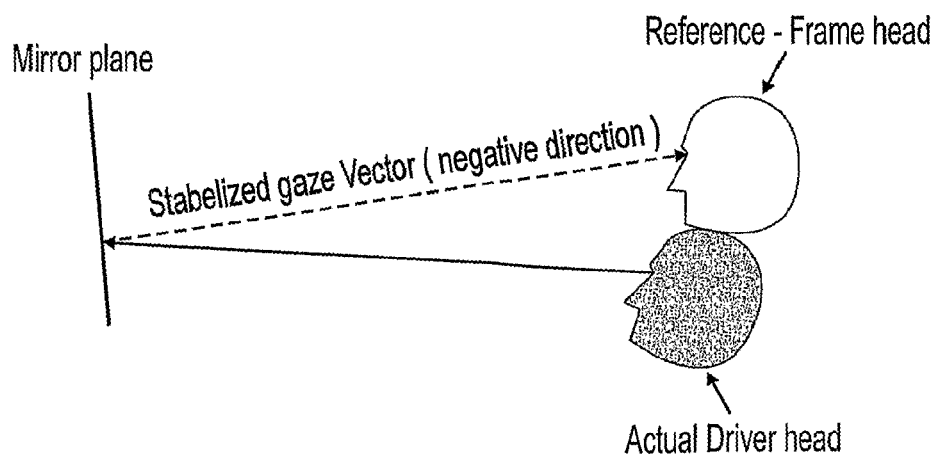
FIG. 36 is a schematic demonstrating the translation of an actual head position to a reference frame.
Figure 37:
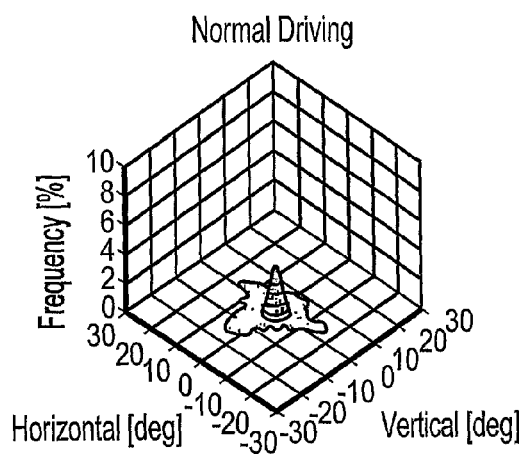
FIGS. 37-40 variously demonstrate, graphic depictions of day cluster or density collection exemplarily identifying percent or peak road-center.

In a further development of the concept of identifying the road center, preprocessing of the data is performed utilizing pure mathematical translations and rotations, as well as signal filters. Since eye-gaze is a vector that originates from a point between the eyes, it becomes dependent on the position of the head. Every object in the driver's field of view can be positioned by a visual angle from the driver's eye. The angle though is highly dependent on the driver's head position and rotation, which in turn is dependent on the driver's height and preferred driving position. Different head positions/rotations affect the properties of the gaze signal as well as head movements. In order to minimize these effects, the head position is normalized to a reference position, advantageously taken as approximate mean position of most drivers. This is accomplished via a theoretical mirror plane located in front of the driver as depicted in FIG. 36.

Therein, measured gaze and head angle is projected via this plane onto a static or reference head. In this embodiment, it is the static head's gaze and head angle that is used in the algorithms.

When gaze confidence is low, for instance when the eyes are occluded, the algorithm automatically switches over to head orientation and uses the face-forward pointing direction as if it was the gaze vector. The resulting signal is then feed into the hybrid algorithm described herein, and road center is localized via the gaze density function. The initialization procedure takes approximately twenty seconds of normal driving with a speed greater than 70 km/h. In this particular application, road center was defined as an oval, 20 by 40 degrees, centered by the density function estimate of the straight ahead view. The road center geometry could, however, be dependent on speed and/or environment.

The oval described above is ideal for speeds above 70 km/h and below approximately 120 km/h on two-lane motorways with medium traffic. Other geometries can work best for some environments, travel being under-taken at different speeds, and for other applications. Measures of long glance duration; that is, one glance extended in time, seems to work better with a horizontal band of 20 degrees, centered vertically by the gaze density function.

The road center defines the only world object in the driver view. The driver either looks at the road center, or not. A transition delay is used in order to avoid a flickering signal when gaze is right on the edge of road center. Gaze has to remain constant on one of the two objects (on or off road) for more than 100 ms for a transition to be recorded.

Once road center is valid (i.e. the gaze density function is stable), PRC (taken here to mean either peak-road-center, or percentage-road-center) will start to calculate. Out of necessity, the algorithm pauses whenever there is no source tracking data. Still further, and preferred embodiment, the algorithm is disabled whenever the vehicle speed falls below 65 km/h. This also resets the value of the PRC to 80 percent.

in one version of the PRC algorithm, a maxPRC parameter prevents PRC from climbing above 80 percent. This is a simple way to stabilize PRC during normal driving (for some subjects normal driving varies between approximate PRC values of 75 and 85 percent. Using this restraint, PRC will always fall to a certain level (from PRC 80%) for a certain number of glances. The same reasoning goes for minPRC and cognitive distraction.

A shorter PRC window (3-10 seconds) is used to indicate time-sharing behavior; i.e., multiple glances between two target areas. The time-sharing behavior indication is used to reset PRC to 80% when the behavior is ended; e.g., at the end of a secondary task.

Three different warnings/feedbacks to the driver can be exemplarily given. Even if PRC falls below a threshold, the warning is not given until the driver looks away from the road (the cognitive warning is an exception of this). In the case of visual distraction, a tickle level is reached when the subject is slightly distracted; i.e., when PRC falls below 65%. The warning is given a maximum of two times during a 10 second period, and only when the driver looks away from the road; that is, the warning will be given the first two glances away from road-center after PRC has fallen below 65%. Another warning level is reached when the subject is severely distracted; i.e., when PRC falls below 58%. In this case, immediately after this warning is issued, PRC is reset to normal driving; i.e., 80%.

In the case of cognitive distraction, the cognitive warning is issued when the driver is cognitively distracted; i.e., when PRC is above 92%. PRC is then reset to 80. A long glance (away from the road) warning is issued whenever a glance outside of road center lasts more than four seconds.

Using a time window might not be the optimal solution. A one-minute time window has a one-minute history, thus what the driver did half a minute ago will affect PRC, as well as the current task. If the driver tunes the radio and thus has four glances to the radio, he will be punished by these four glances for at least half a minute; that is, PRC will remain low for at least 30 seconds even though the driver is back to normal driving (this is assuming that the task lasted for a maximum of 30 seconds). There are several ways to deal with this problem.

One is to use a shorter window with a dampening factor (to obtain the approximately same window dynamics). Another is to flush the window whenever a task is completed. Still further, a much shorter time-window, for example 3-15 seconds, can be used to decide weather a task is being performed or not.

The time-sharing detector may be used to decide weather the PRC-Sum (usually the total time of all on-road-center glances within the time window) should neglect on-road glances; that is, while performing a task, the PRC-sum decreases proportional to the off-road-center glance time, but neglects the on-road-center glance time and thus gives the same dynamic of the sum as the window would.

Another problem with the current algorithm is that blinks quite often are interpreted as glances down towards the instrument cluster. Standard data filtration will not filter out blinks due to slightly different properties in the gaze signal. Proposed solutions include using the eye-opening signal to determine weather it is blink or a glance. This requires the eye-opening signal to be present in the log data when the program is in "non-latency mode." An alternative is to design a blink detector. A blink is too short to be a glance and could thus be stopped in a filter. This will, however, introduce a delay in the system of at least 150 ms.

The algorithm above is tuned for medium traffic motorway driving at approximate speeds of 70-120 km/h. There are several ways to adapt the algorithm to different speeds and environments. One is to adapt the road-center area to speed and environment. As speed decreases, road-center will increase in size, mostly in the horizontal field. Road-center is increased so that normal driving in this speed and environment has an approximate PRC of 80%. There are two ways to do this. One is to adapt to each driver on-line. Another is to provide predefined road-center geometries for different speeds and environments. Still another is to adjust the warning thresholds according to the PRC level of normal driving for the particular speed and environment. Yet another is to provide a description of the environment, or at least the environment indicated by the driving behavior.

A limitation is that the algorithm will fail if the driver's head is turned more than about 60 degrees away from the road center; that is, if the driver looks over his shoulder or to the side to see if there is a car in the adjacent lane. Pattern recognition may be used to fill in those blanks.

Apart from direct warnings, PCR can be used to enable/disable a third party system or set it into different modes. For example, PRC can be used to set a forward collision warning (FCW) system into "sensitive" mode, and the instant eyes-on-road-center signal can be used to decide weather a warning should be enabled or not. It could also be used to adjust the time-gap for an Adaptive Cruise Control (ACC) control loop (increase or decrease the safety distance) or enable/disable other warnings and systems.

Many of the measures outlined herein make use of a reference calculation of the Road Center Point (RCP). The vertical and horizontal Road Center Point is calculated from a segmented eye-movement data set (segmented into fixations/smooth pursuits and saccades) of, for example, three minutes of data. First, every fixation data-point is added to a vertical and horizontal bin; for example, a bin-size of 0.98 by 0.98 degrees (128 times. 128 for +/−30 degrees from straight ahead, or the zero point). Next, the mode of the bins (largest frequency in bin) is set as the Road Center vertical and horizontal point. These data-point-based measures are more fully described illustrated in FIGS. 37-40 where the road center point is identified based on sample density of driver eye positions. Eye movements in normal driving conditions on a straight two-lane freeway are depicted in these Figures. The data is concentrated around the road center point, and the road center point is set to zero based thereupon. The frequency in units represents the percent of total frequency per bin (one bin equals 0.98 degree by 0.98 degree). Left and upward eye movements are positive, right and downward eye movements are illustrated as being negative.

For each step in a moving time-window, for example, a one-minute time window with a 60 Hz update frequency, the following is calculated. Each fixation data-point within the time window is classified as being either of a type "1" representing a "road-center" or a type "0" representing a "non-road-center," the differentiation being made on the basis of being inside or outside the defined Road Center Area. The Road Center Area is, for example, calculated by taking the distance in degrees/radians from the Road Center Point and setting a cutoff threshold, for example, eight degrees as a radius around it. Those fixation data-points that fall within the cutoff threshold are classified as "road-center" and those that fall outside are classified as "non-road-center." In this example, the cutoff threshold defines the shape of the Road Center Area.

Figure 38:
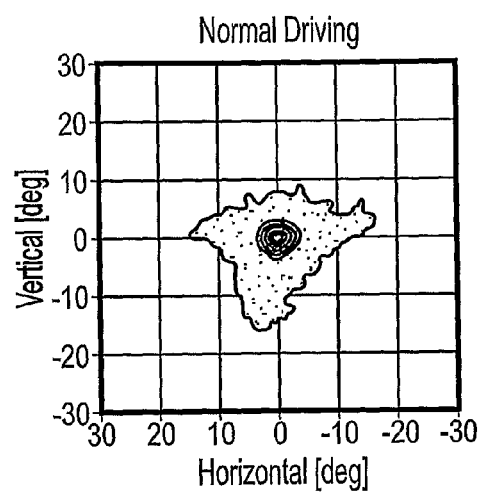
Figure 39:
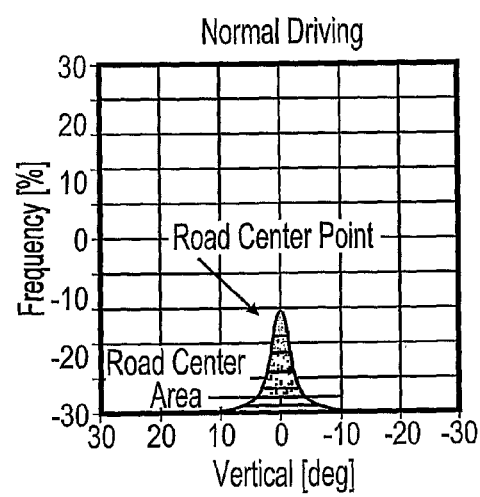
Figure 40:
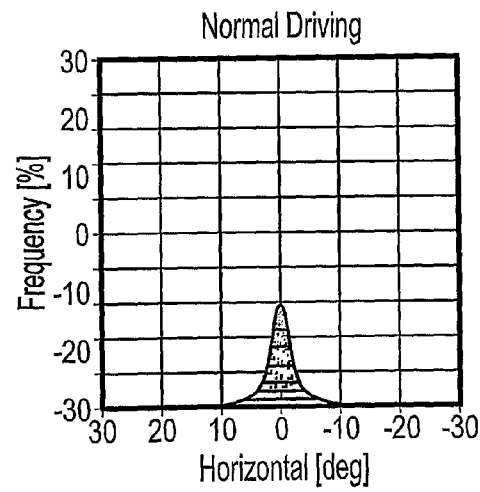

The Road Center Area can also be defined in other ways as an alternative to using a radius cutoff threshold. For example, the Road Center Area can be defined as a non-symmetrical shape. A non-symmetrical Road Center identification is useful when driving in a curved or busy road environment. Some ways to define a non-symmetrical shape are: (1) a threshold level can be set at a frequency per bin such as the horizontal Road Center Area line shown in FIG. 39. A geometric shape like the outline of FIG. 38 is the product; (2) the Road Center Area can be defined as data within, for example, one or two standard deviations from Road Center Point. Standard deviation can be defined based on the radius of the center point or separately based on the vertical and horizontal components. A vertical/horizontal standard deviation definition would enable the shape to be calculated as being oval; (3) in curved road environments, most fixation data-points are centered around the vehicle's future path. Instantaneous path trajectory is commonly calculated from vehicle yaw rate (or measures based on steering wheel angle). This curved path trajectory (converted to visual angles) can be used to define an area of valid "on-path fixations." This trajectory can be used to define an "On Path Area" of, for example, glances within a certain distance from vehicle path. Thus, PRC, A-PRC, and PLG can be calculated in the same way as described above substituting Road Center Area with On Path Area. Finally, a calculation of percentage is made by dividing the number of road-center data-points by the total number of fixation data-points within the window, and multiplying the product by 100. The percentage calculation thus ignores saccades and missing data.

Figure 3:
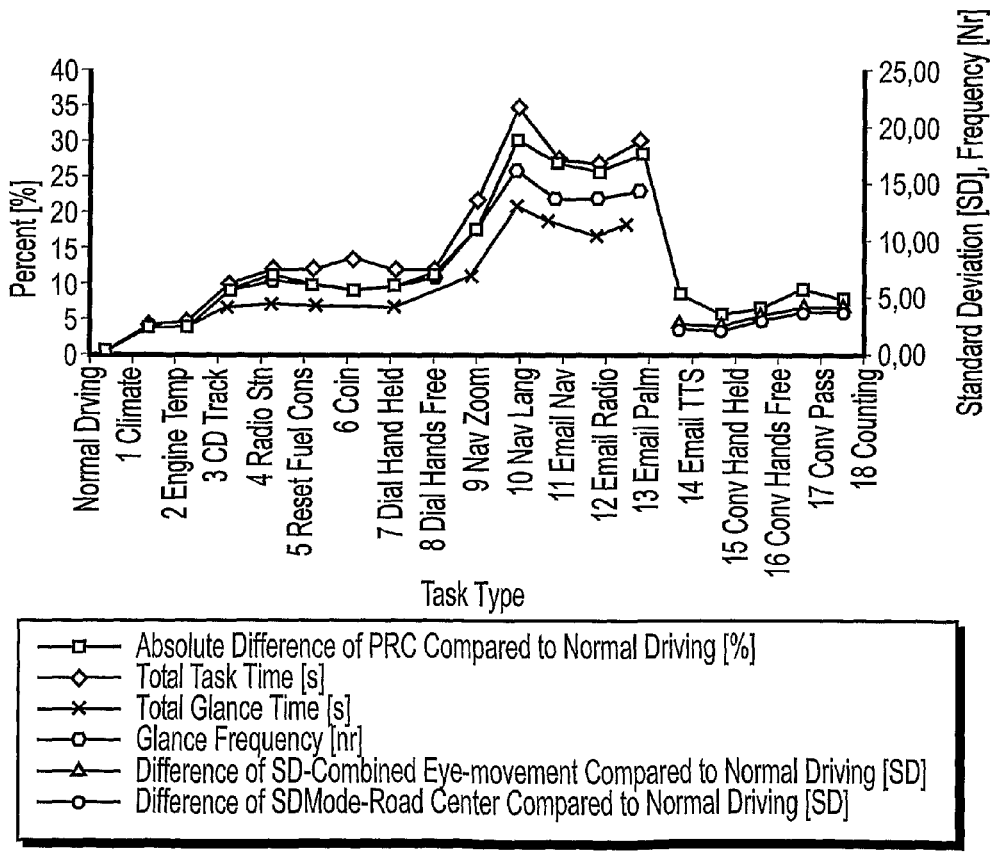
FIG. 3 is a graphical demonstration of absolute percent road center shown in relation to other measures of distraction.

Absolute Percent Road Center (A-PRC) is calculated, in the same time window as above, as the absolute difference from a given PRC value; for instance, the PRC value of normal driving. FIG. 3 shows a comparison of the A-PRC with some other common measures of distraction.

Figure 4:
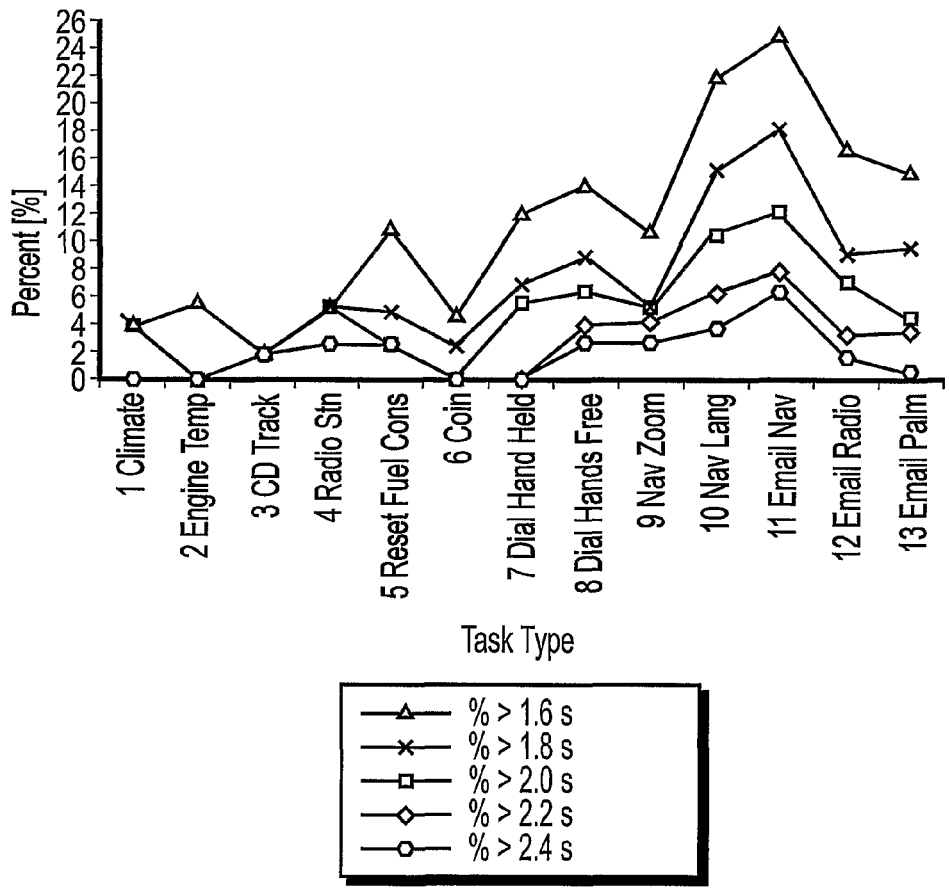
FIG. 4 is a graphical demonstration of percent long glances away from the road center for different time thresholds.
Figure 5:
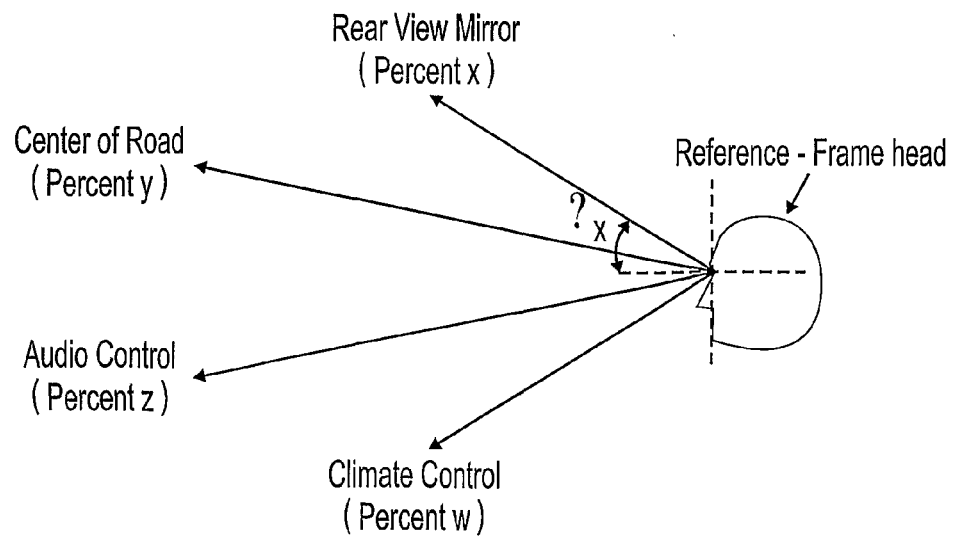
FIG. 5 is a schematic view demonstrating a measure of gaze-direction.

Percent Long Glances away from Road Center (PLG) is calculated, in the same time window as above, as the percent of fixation data-points which are classified as glances (as defined by the SAEJ-2396 standard) over a certain time threshold, for instance, two seconds as exemplified in FIG. 4.

Standard Deviation from Mode Road Center (SD-MRC) is calculated, in the same time window as above, according to the standard deviation formula, but with the exception that the mean is replaced with mode as exemplified by:

DistRoadCenter=sqrt(((VerticalPos−VerticalMode) {circumflex over ( )}2)+((Horizontal-HorizontalMode) {circumflex over ( )}2))
SD-MRC=sqrt(sum((DistRoadCenter) {circumflex over ( )}2)/length(NonFixation-s))

Percent Outside Vehicle (POV) is calculated, in the same time window as above, as the percent of fixation data-points that fall outside the vehicle and fixation data-points that fall on the rear or side mirrors. The interior of the vehicle is defined as a geometric area in degrees or radians.

An example data set was gathered relevant to the present inventions. A validation study was conducted in a simulator environment using a 7.5 m×2.2 m "powerwall" screen with one hundred and eleven degrees of view and with a resolution of 2456×750 at 48 Hz. Fourteen subjects took part in the study and various in-car tasks, such as using a mobile phone, changing radio stations and the like where preformed. The data was collected and is also available in video transcribed form according to the ISO 15007-2 method (ISO 1999). In what is referred to as the GIB-T Vigilance Study, the same simulations were performed in the environment described above and included twelve persons driving on a four-lane motorway in light traffic. Each person participated on two occasions, one drives thirty minutes under normal conditions and approximately two and one quarter hour with sleep deprivation; the results were recorded using a video recorder. This set is part of a larger on-road experiment where sixteen subjects participated. Each person performs various in-car tasks during a thirty kilometer drive and about fifteen minutes of normal motorway driving.

Figure 41:
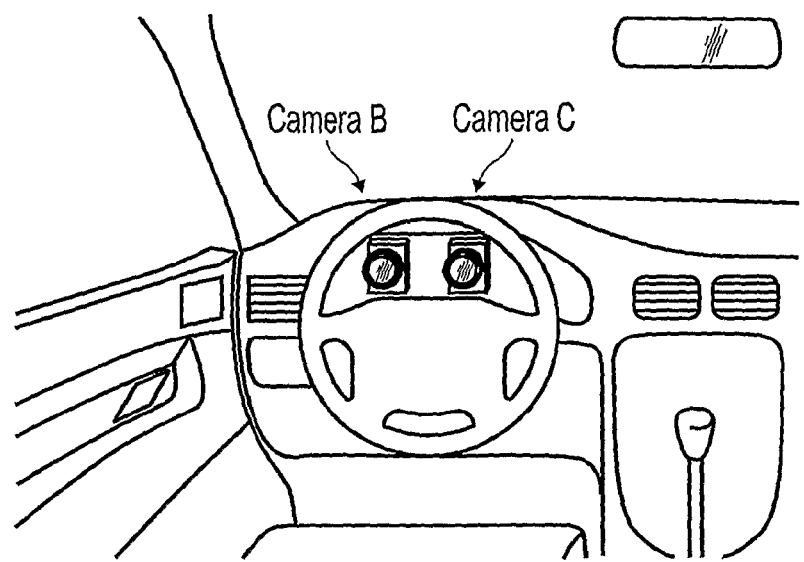
FIG. 41 is a perspective view taken inside a vehicle toward the instrument panel where two "stereo" tracking cameras or monitors reside.

Tracking systems have the ability to track the head position and angle, as well as the gaze angle with respect to a fixed coordinate system. Tracking systems uses stereo-vision; that is, two cameras positioned in front of the subject driver ahead of the instrument clusters, but behind the steering wheel as depicted in FIG. 41 for tracking head position and gaze. Alternatively, and preferably, a single camera may also be utilized as illustrated in FIG. 28. This is a considerable improvement to other existing eye tracking systems that are intrusive. A tradeoff using this technique, compared to non-vision based strategies is slightly poorer gaze estimation (±3°) compared to systems that use some kind of corneal reflection (±1°). These other types of vision-based systems depend on mono-vision, and do not work as well. One substantial advantage of the presently disclosed system is that it outputs both head and eye vectors, simultaneously.

The utilized system uses a template-matching algorithm to find facial features, such as eyebrows, corner of the mouth and eyes. Each template is considered part of a 3D rigid body face model. When several features are found in both pictures, a 3D position of the head and eyes are calculated using a least-squares optimization of the model rotation and translation. The solution to this problem is biased towards points that are tracking well which make it robust with respect to occlusion, noise and perspective distortion. Furthermore, a Kalman filter is used to reduce noise and predict the head-pose in the next iteration, this reduces calculation time for the next frame.

The eye-gaze estimation is based on the head-eye position. Using a measurement of the eyeball center of rotation and the center of the iris, gaze is computed as a ray through these two points. When both eyes are visible, the gaze direction is calculated as the mean of the two vectors, otherwise the visible eye-ray is used. If none of the eyes are detectable, for example when the subject's head is turned more than some sixty degrees, or when the eyes are occluded, the face normal is used as gaze direction.

An eye-closure detection algorithm is utilized to determine whenever a subject is blinking. The distance between the upper and lower eyelids, scaled by the distance between the eye corners, is used as a measure of eye-closure. In order to compute these distances, the system uses edge detectors and then approximates parabolas, one on each eyelid, which passes through both eye corners. The eye-closure measure and a few other measures (eye-image region vertical optical flow, region temporal rate of change, nr of pixels with color of eye sclera and eye template correlation coefficient) are then weighted together and a threshold determines whenever the subject is blinking.

The system outputs a number of signals, a few example of which include, but are not limited to: (1) the gaze signals "gaze_rotation_raw" and "gaze_rotation_filtered" are the same signal in the instant case since the filter parameters were set to zero in all studies. The signal consists of two directions, pitch and yaw, given in radians. (2) the "gaze_confidence" signal provides a confidence measure for the gaze estimation algorithm. (3) the "head_position_filtered" and "head_rotation filtered" uniquely determines the 3D position and rotation of the head. These are the same as "head_position_raw" and head_rotation_raw" since all filter parameters where set to zero in the available data. (4) "tracking" status indicates whether the system is in tracking or search mode. (5) "blinking" indicates whether the subject is blinking. (6) "time" is the CPU time associated with each estimation.

It would seem that the information content in the gaze signal is not at all constant, but rather varying over time. During recordings, there are occasional glances towards objects that are unlikely to be focused at this point such as the subject driver's knees, inner ceiling of the vehicle and the like. Some of these glances can be referred to as undetected eye-closures that cause a dip in the gaze signal. The system can also be sensitive to different lighting levels. It is capable of handling changes in background lighting, however not when the change is rapid such as when the vehicle moves out from a shadowy road strip into a sunny one. The result is a high noise level and sometimes almost non-existent information content. Direct sunlight into the camera lenses makes the signal even noisier due to lens flares. Occasionally this leads to the loss of tracking for several seconds.

Figure 42:
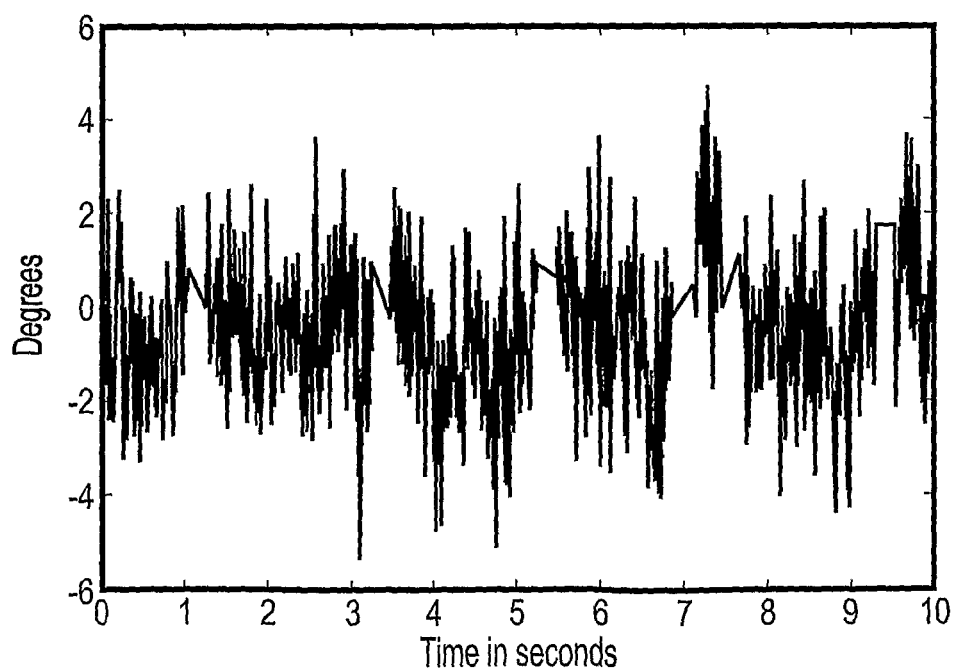
FIG. 42 is a graphical demonstration of a gaze horizontal signal with interpolated blinks.

The "dip" mentioned above during eye-closures is doubtlessly due to the fact that the eyes are closing which leads to an approximation failure (as mentioned in the introduction). The dip is very obvious in the pitch signal, some 30-40 degrees, but can also be perceived in the yaw signal. A typical blink lasts on the order of 300 milliseconds, but a dip, however, lasts only for about 100 milliseconds. Thus, the estimation does not collapse until the eyes are almost shut. The dips are easily removed in the preprocessing stage using a median filter. In an exemplary embodiment, the system simply cuts out the blinking part indicated by the blink signal and linearly interpolates between the last known sample and the first new one as is exemplified in FIG. 42 where blinks have been interpolated. The result is that significant portions of data, often almost 300 milliseconds worth, is removed and replaced with a somewhat rather unnatural representation; that is, a straight line. Since blinks often occur during saccades, no proper measurements can be made. It would be advantageous to reconstruct these features in order to make accurate measurements.

The blink signal is not always consistent with reality. This is obvious when the subject performs tasks and, according to the blink signal, never blinks but in reality it is known that blinking had to have occurred. In the exemplary system, the more a subject moves their gaze, the less accurate is the blink signal.

The gaze confidence signal could be used to overcome a large portion of the deficiencies described above. Experience, however, shows that the signal quality and gaze confidence measure does not always correlate. It can differ significantly, not only for different subjects, but also for different samples taken from the same subject. Further more, the confidence measure drops to zero with every blink. In the instance of an undetected blink, it is not possible to be certain that the incident was in fact a blink that drove confidence to zero, or an artifact. Hence, the confidence signal can not be absolutely relied upon.

The fact that the computation rate of the system is "about 60 Hz," the sampling interval is not constant but rather dependent of the computation time for each frame. In the exemplary system, however, time is available both in seconds and milliseconds, as well as a computation delay-signal in milliseconds. The delay is on the order of 150-200 milliseconds.

Finally, different subjects have different facial features making them more or less suitable for system-based measurements. Facial features with good contrast often correlate with good data quality, so does correct head position that is centered in the camera view.

The design of change detection algorithms is always a compromise between detecting true changes and avoiding false alarms. Varying noise and signal properties makes the gray zone even larger. Since the signal quality varies the idea was to use an adaptive filter to overcome this problem. Generally when an adaptive filter is proposed, it are the filtering coefficients that adapts to the signal using some kind of estimation process; for example, Least Mean Square (LMS). However, the data signals proved to have characteristics, such as changing information content and strange artifacts, which makes them less suitable for this kind of adaptation. Instead, a hybrid algorithm that makes use of two pre-processing median filters was developed. This is described in this chapter both for an off-line and a real-time algorithm. But first a brief review of some different algorithms commonly used for eye movement segmentation.

The work of Salvucci and Goldberg has been defined in "Identifying Fixations and Saccades in Eye-Tracking Protocols" wherein several different techniques have been gathered for identifying saccades and fixations.

Velocity-based
Velocity-Threshold Identification (VT-I)
HMM Identification (HMM-I)
Dispersion-based
Dispersion-Threshold Identification (DT-I)
Minimized Spanning Tree (MST) Identification (MST-I)
Area-based
Area-of-Interest Identification (AOI-I).

Since verified work had already been done on the VT-I method, a first approach was made using the DT-I method. The DT-I algorithm is considered quite accurate and robust, however, the inaccuracy and noise of the eye tracker used here makes it less suitable. Saccades are identified due to noise and spikes, and fixations beginnings/endings are inaccurate due to the signal properties; for example, occasional drift before a fixation becomes more or less stationary. Another problem is smooth pursuits, which causes the algorithm to collapse when smooth pursuits are considered as one fixation. Thus, the dispersion method cannot be used alone.

The HMM-I, on the other hand, makes use of probabilistic analysis to determine the most likely identification. The HMM model in HMM-I is a two state model. The first state represents higher velocity saccade points; the second state represents lower velocity fixation points. Given its transition probabilities, the HMM-I determines the most likely identification of each protocol point by means of maximizing probabilities. The algorithm is considered to be accurate and robust, given the right parameters. These are estimated using a re-estimation process, the primary intricacy of HMMs. The implementation of this estimation is both complex and tedious.

The VT-I algorithm does not have the problems mentioned above. However, the velocity threshold is a compromise between picking up noise and identifying accurate fixation beginning and ending. In order to minimize this problem, a dual-threshold algorithm was adopted (DualVT-I). A high threshold ensures proper saccade identification. If a saccade is detected, the low threshold is used to calculate the beginning and end.

The primary disadvantage of the VT-I algorithm was the lack of robustness. This is however greatly improved in the DualVT-I.

None of the identification methods described in the previous section are in any way perfect; they all have different flaws. Hence, a combination of two algorithms and the additional rules for eye movements where chosen for this work, namely the DualVT-I and DT-I. This combination works as an adaptive algorithm in the sense that the decision-making is automatically biased towards the DT-I and rule-based part while preserving the DualVT-I properties as noise increases. This combines the exactness of the DualVT-I velocity protocol and the robustness of the DT-I dispersion protocol. One way to look at it is to consider the rules as algorithm control, meaning they bias the "decision" towards the algorithm part working most accurately at the present time. The algorithm cooperation is illustrated in FIG. 25.

Regarding preprocessing, the raw-data needs to be preprocessed prior to segmentation. It is more or less noisy and contains blinks and non-tracking parts.

Figure 43:
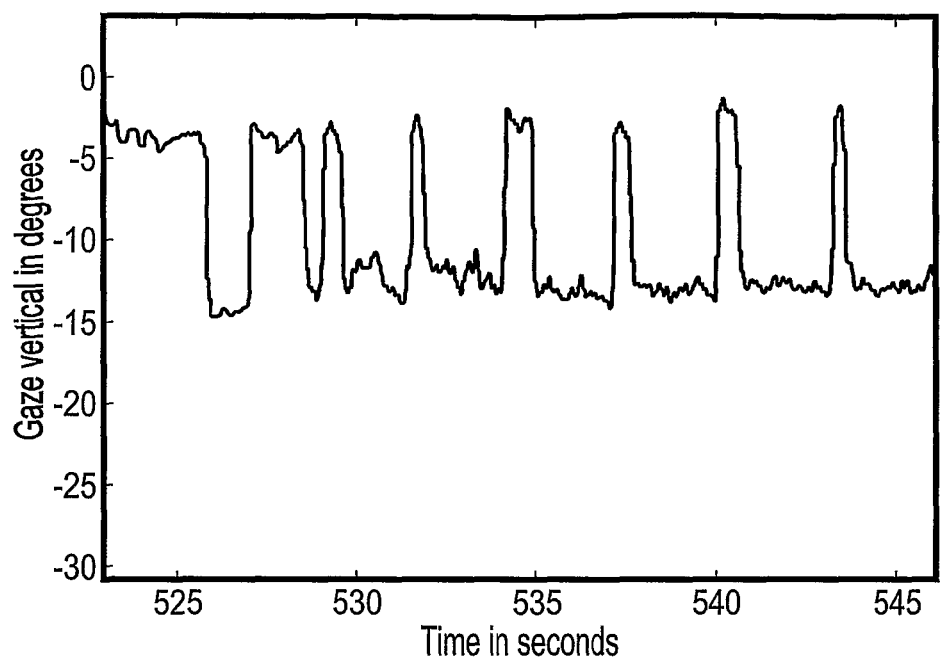
FIG. 43 is a graphical demonstration of horizontal gazes and showing three dips due to blinking.

Many researchers have pointed out median filters and FIR-hybrid-median (FHM) filters to be appropriate for eye movements. The median filters special characteristics to preserve sharp edges while noise and outliers are subdued is suitable for saccadic signals. In general FHM or a weighted-FHM filter is considered to work best, however a 15 sample sliding-window median filter reduces noise sufficiently. As a positive side effect it also suppresses the "blink dips", produced whenever the subject blinks, enough to pass the segmentation undetected as demonstrated in FIG. 43.

A completely different problem is the blink interpolation as described earlier and in which the gaze signal is replaced by a linear interpolation. If this occurs during a fixation, it is usually no problem. However, humans often blink during saccades that only last for some 100 ms while 200-300 ms are replaced with a straight line. To get around this problem a reconstruction is necessary. The present invention employs a simple, robust solution that provides a proper number of glances, whereas time based measures are less accurate. Noise, of the same amplitude as present in the signal, is added to all blinks with dispersion less than five degrees and all other blinks are marked as saccades. The five-degree threshold was set based on all the data available, without detecting any false fixations. Fortunately, subjects tend to blink less during tasks with multiple glances.

As mentioned earlier, the identification algorithm chosen is a hybrid between the velocity and dispersion protocol as well as rules outlined by the physical properties of the eyes and eye tracker equipment. In the off-line version, the processes run in series, at first the velocity protocol using a dual threshold is applied and then the dispersion protocol with the rules. This is illustrated in FIG. 23. A fixation restoration algorithm is used when noise or some other property of the signal has prevented the detection of a fixation (that should be there according to the ocular rules). This is illustrated as an arrow back from the DT-I and rule-based block to the DualVT-I block. Also, the automatic clustering algorithm has been included into the hybrid shell. It administers the glance detection.

Each algorithm part will now be further described. The derivative (velocity) estimate is computed by means of a two-point central difference:

$$\partial y(x) = \frac{y(x+h) - y(x-h)}{2h}$$

applied to each gaze component and then weighted together with a square-sum-root to form the 2-D velocity. Noise is always a problem when differentiating a signal, one way to handle this problem is to low-pass filter the derivatives. The central difference however, can be described as an ideal differentiator and a low-pass filter in series. The frequency response is calculated:

$$\dot{Y}(\omega T) = \frac{Y(\omega T) j \sin(\omega T)}{T}$$

Figure 44:
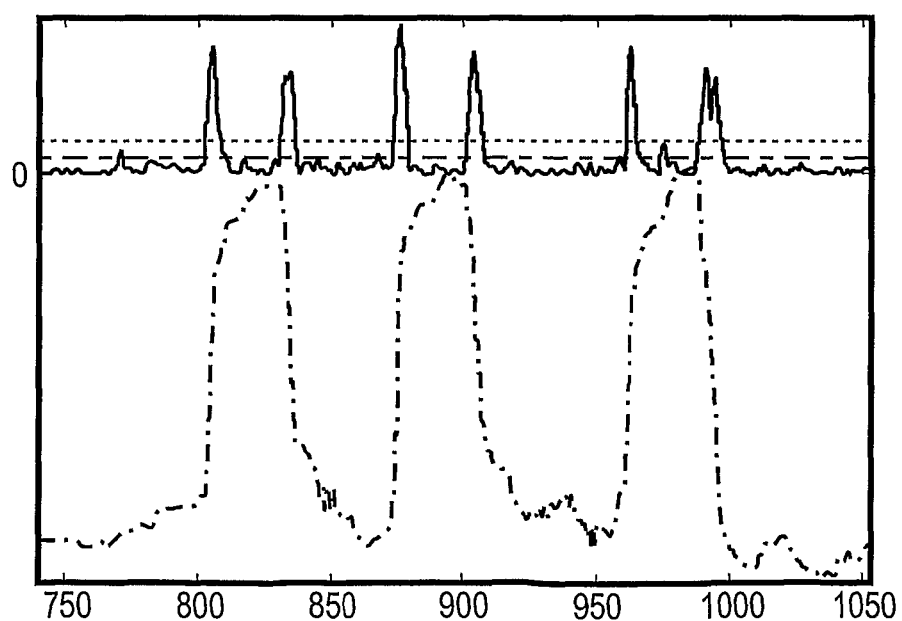
FIG. 44 is a graphical demonstration on eye motion velocity with respect to thresholds.

With the sampling rate set to approximately 60 Hz, this filter has a 3 dB cut off frequency of about 14 Hz. This rather low cut-off prevents aliasing, ensuring that frequencies of more than 30 Hz are subdued but still high enough not to distort saccade beginnings and endings. The dual thresholds and the velocity estimate are shown in FIG. 44.

One experimental comparison of five derivative algorithms found the two-point central difference to be the most accurate technique for 12-bit data. Among the advantages of this method are that it is simple, accurate and fast.

Thresholds for the saccade detection where set primarily by comparing the results with the results of previously performed semi-automated analysis.

Figure 45:
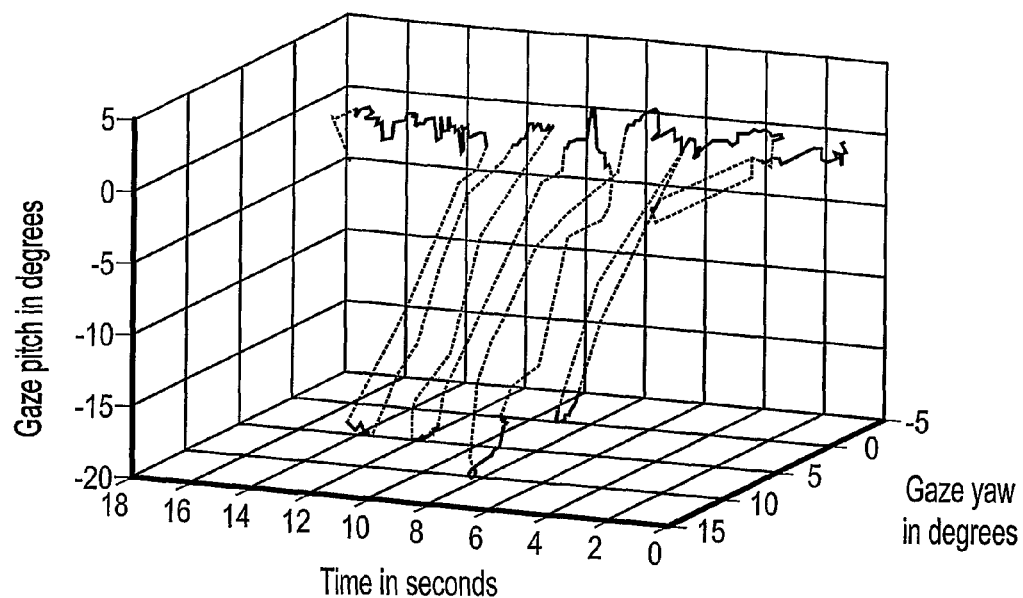
FIG. 45 is a graphical demonstration of a segmented gaze signal.

Now, although the derivative approximation is automatically low-pass filtered it is still very noisy, the noise level being at approximately 70°/s. However, since the data gathering system has an inaccuracy of ±3° at the best, and the peak velocity of saccadic movement is higher than 100°/s for amplitudes larger than some three-four degrees, no problem is posed. Despite this, practical evaluations have shown that the occasional error may slip through, especially when noise increases. Those inaccurate identifications are detected and removed by the DT-I part in the next step of the segmentation process. Thus the accuracy tradeoff using three samples for the velocity estimation has proved to be negligible.

in the second step, the physical criteria stated hereinabove, and parts of the dispersion-based algorithm determine if detected saccades and fixation are valid (rules application). A three-dimensional representation of exemplary saccades and fixations is provided in FIG. 45. When the noise level is high, the derivative approximation becomes more sensitive and confusing artifacts are occasionally detected within fixations. Their removal has a few ground rules preventing misjudgment: 1) A saccade can be altered into part of a fixation if the new fixation dispersion is less than a threshold; and 2) A saccade can be altered into part of a fixation if the variance of the fixations is less than a threshold.

If these criteria are fulfilled, the two fixations are joined using a linear interpolation with some added noise. The noise is introduced in order to avoid making this part of the signal non-physical. The original signal often contains a spike of some sort, hence the interpolation.

Figure 46:
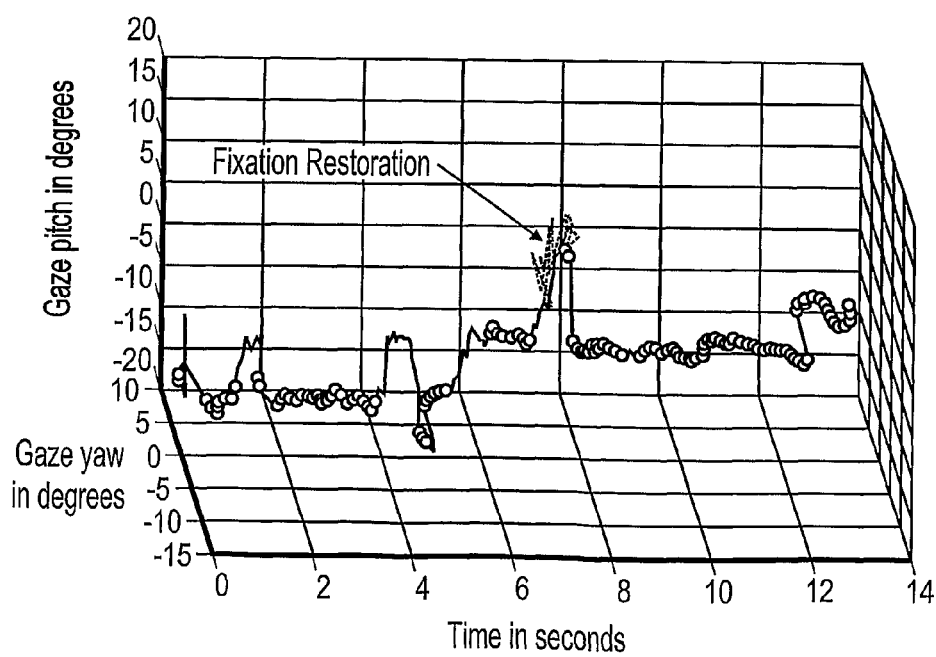
FIG. 46 is a graphical demonstration of a restored fixation.

Likewise, fixations are removed and simply marked as saccades if they are non-physical, meaning the duration is less than some 150 ms. This occurs when the signal's information content is low.

in the offline version (when a long delay is acceptable), a fixation restoration algorithm as illustrated in FIG. 46 has been developed to compensate for the, sometimes, low information content in the gaze signal. This can occur in the beginning of a fixation when the algorithms have not stabilized themselves. It works under the assumption that a saccade is not likely to last longer than some 200 ms and if that is the case, it is most probably two saccades and an undetected fixation in between. Based on this the algorithm locates saccades that might contain an undetected fixation and then filter them using a sliding median filter somewhat longer than the one used in the preprocessing (20 samples). This calms the signal noise enough to, sometimes, detect a new fixation. Now, this may seem as a straightforward and dangerous method, more or less forcing detection. It is, however, merely an adaptive property of the segmentation formula and has been proved to correlate strongly with reality with respect to the validation portion.

The glance classification algorithm works in two steps. At first, all clusters are automatically localized based on their total dwell-time. In the second step these clusters are clustered themselves, based on the same dwell data, and world model objects are formed. A world model is a simple description of different pre-defined view areas, for example, the right rear view mirror or the road strait ahead. All models are defined in a plan perpendicular to the driver when he/she looks at the road straight ahead.

Figure 47:
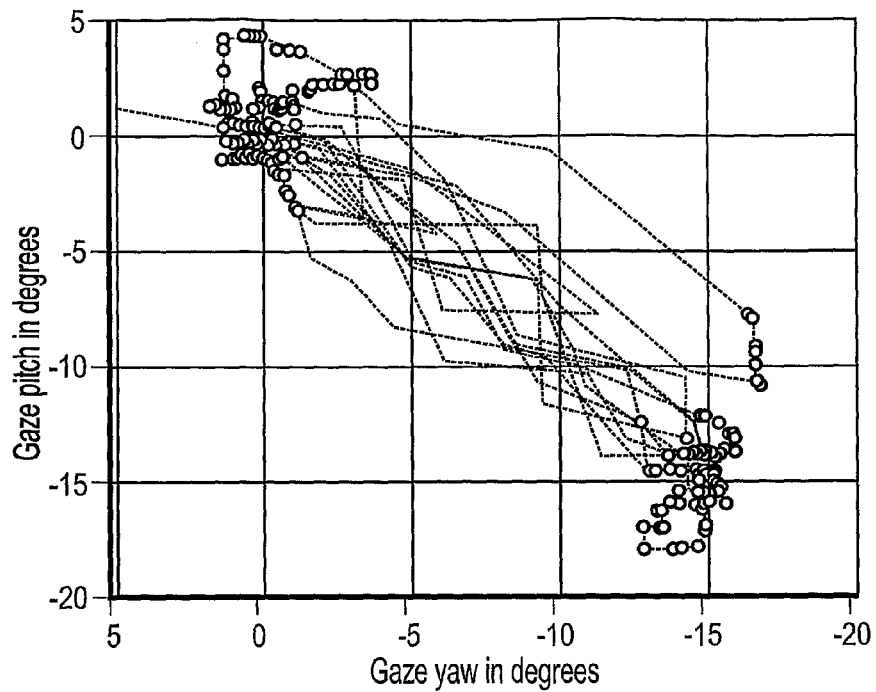
FIG. 47 is a graphical demonstration of multiple glances away from the road-ahead-scene.
Figure 48:
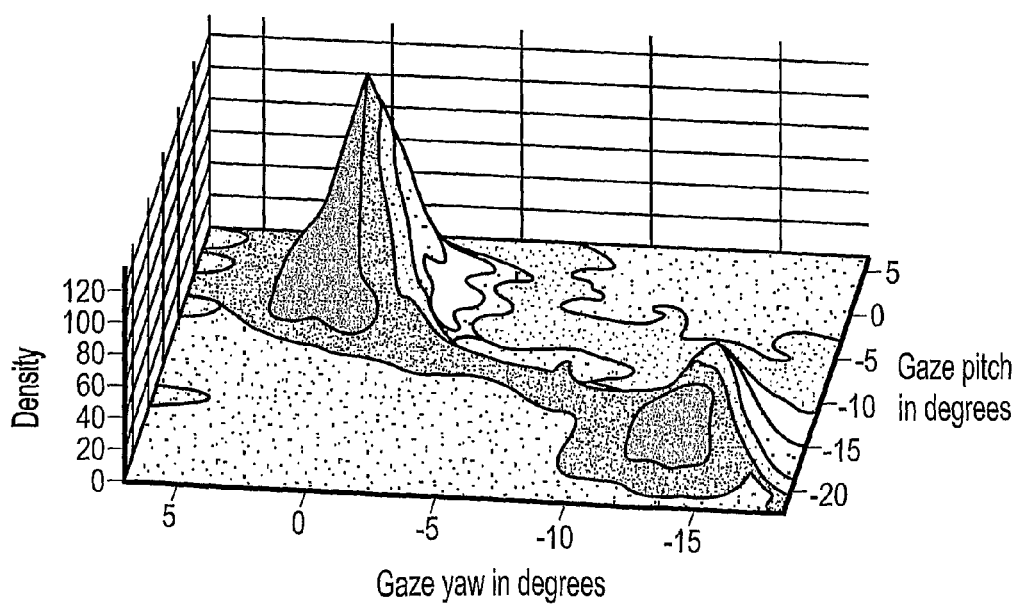
FIG. 48 is a dwell histogram showing two areas/objects of interest.

In the first step, a rough approximation of cluster locations is done using a 2D dwell-time-histogram; that is, total fixation time in different view areas based on the duration and mean position of each fixation as depicted in FIGS. 47 and 48. Usage of the mean position has proved to be a simple way to reduce noise problems. The histogram bin-size was set to 3-by-3 degrees, mainly by trial an error. This creates a nice, smooth histogram where every peak indicates the approximate position of a cluster. Since gaze data is given in radians, the actual cluster plane is not a plane, but rather the inside of a cylinder. Thus, the gaze angle does not affect the cluster size. Once the approximate cluster positions are determined, every mean fixation-point is assigned to the nearest cluster-point, by Euclidian means. All clusters are then updated to the mean position of the points associated to respective cluster.

The algorithm also creates a classification log where every classified event is stored in a matrix with its position, beginning, termination, duration, associated cluster and type encoded into numbers where the type is saccade or fixation. The log-matrix is simply a data reduction and, later on, used as base for statistical function calculations.

in the second step, all clusters are mapped onto a world model. Different geometric areas, for example boxes, circles or combinations of the same or other shapes, define objects such as mirrors, center stack, instrument clusters, and the like. Several clusters are usually within the same area belonging to the same glance. These are now joined to one cluster and its mean position recalculated. The number of world model objects varies with the task. A base model of three objects has been chosen for this work and an algorithm based on the dwell histogram makes the objects "float" into place. It then calculates the standard deviation of the distance between the objects center and all cluster positions. The clusters that fall within the 95% confidence values of an object are considered to be a part of it, thus the object size is adjusted to enclose the cluster. The number of world model objects is easily controlled via a parameter.

This is one step that can require inspection and, sometimes, correction from the experimenter. This is because decisions on what is and what is not an object are very difficult due to noise and non-tracking in the raw signal; qualified guesses have to be made by the experimenter. One way to eliminate the need for human rating is to avoid sunny days when collecting data. Direct sunlight into the cameras is the one cause that stands for almost all fixation dislocations.

The world model approach could be very useful for other measurement purposes besides glance classification; e.g., on-road off-road ratio and larger scale visual scan-patterns. It is also useful when the gaze signal is noisy or corrupt (e.g. by sunlight) and fixations are scattered in larger areas forming more clusters than there really are. During the process, the log-matrix is updated continuously.

When templating areas of interest, there are two primary problems: 1) it needs to be calibrated for each and every subject, and run; and 2) the objects often need to be defined larger than they really are due to the inaccuracy of the sensor system. It is difficult to determine how large a world object needs to be before examining the data. If the object is too large there is always a possibility that outliers are included or that objects has to overlap each other.

In light of this, it is easier to define the world model when analyzing the data and let it adapt to the current situation.

At last, the statistical measures are produced using a log-matrix. The measures are as defined as: 1) dwell time; 2) Glance duration; 3) Glance frequency; 4) Total glance time; 5) Glance probability; 6) Link value probability; 7) Time off road scene ahead; 8) Total task time; and 9) Transition time.

Once the glance classification is performed, the calculation of these measures are straightforward, and are therefore not included.

An exemplary real time implementation is very much like the off line algorithm.

The differences are that only "road-scene-ahead" and "other-areas" are defined as world model objects. The output is, for each task, total number of glances and total glance-time on and off road. Task beginning and ending are indicated in the log-file by annotations or time-gaps (this is done manually during logging).

Before any classification is performed, the road-scene-ahead world object is localized. This is done using an initialization phase, calibrating the setup for the particular subject and run. The road-scene-ahead area is localized by means of a gaze density function. Most of the driver attention is directed in this area and the dwell time density function always have a very significant peak in the center of it as shown in FIG. 48. The distribution of fixations in this area is approximated to be Gaussian. Thus, the standard deviation can be computed using the highest point in the dwell histogram as the average fixation position value. Technically, it is not the standard deviation being calculated, but rather deviation of mode. The road-scene-ahead is then considered to be within the 95% confidence values. The procedure is done for both yaw and pitch respectively, thus forming an oval area that represents the road-scene-ahead.

Figure 49:
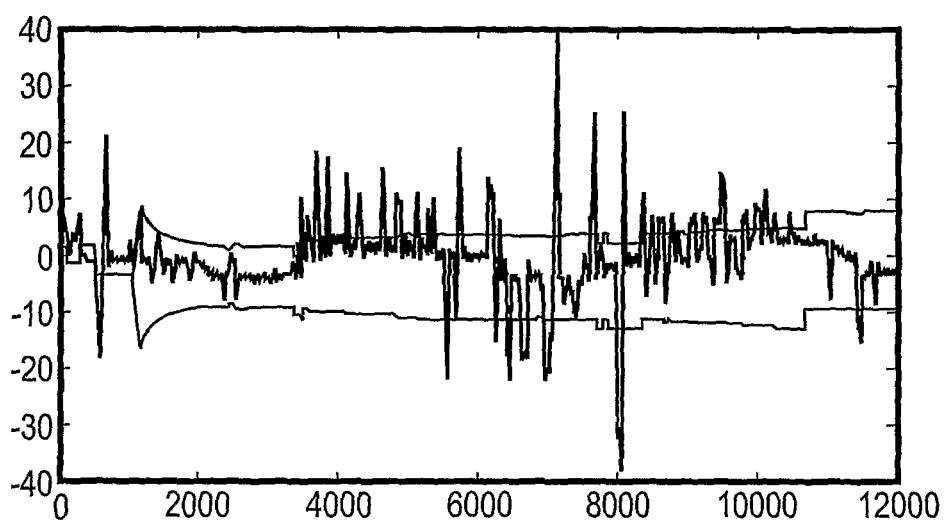
FIG. 49 graphically demonstrates the establishment of road-scene-ahead boundaries.
Figure 50:
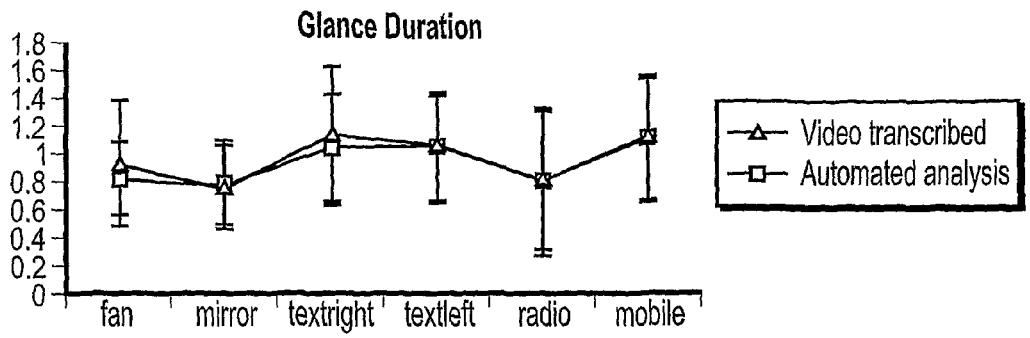
FIGS. 50-53 are graphical demonstrations of various components are aspects of typical glances made by a driver.
Figure 51:
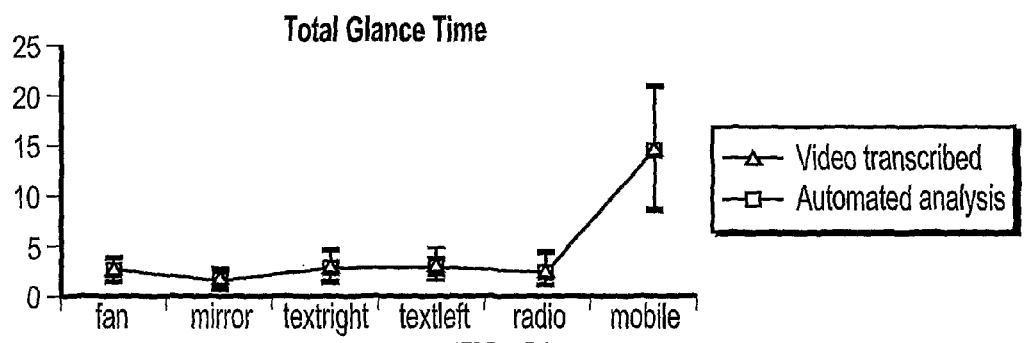
Figure 52:
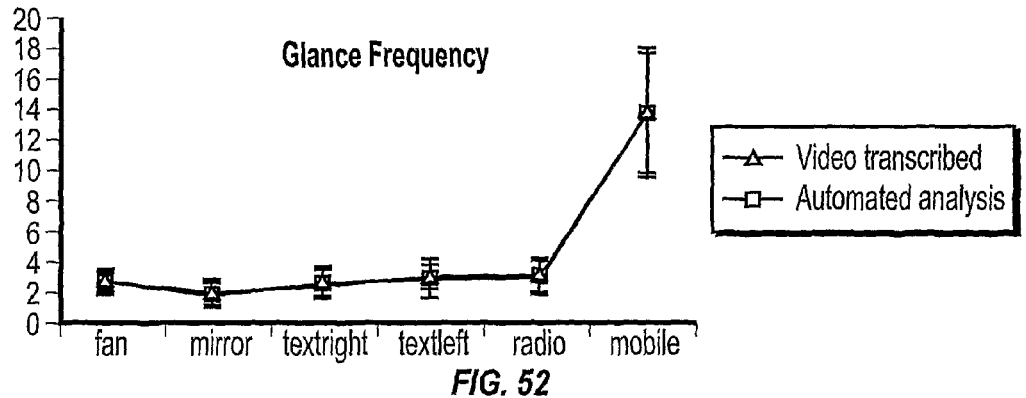
Figure 53:
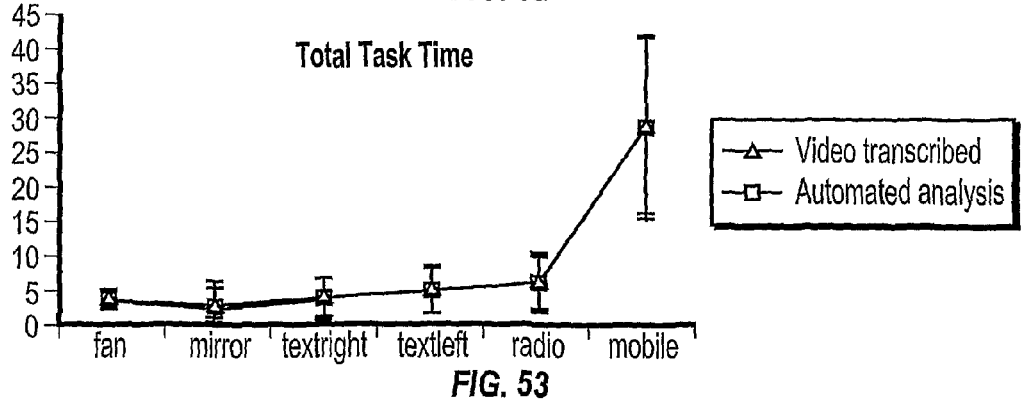

During the initialization the search area is limited to what probably is the road-scene-ahead; typically a circle with radius 10° and center in (0,0) and only fixations falling into this area are used for calculations. Despite this, the 95% confidence boundaries had to be biased about 2 degrees down and to the right in order to make it work with some subjects; a characteristic that arises when a subject's gaze follows the road curvature. Simple solutions to these deviations are exemplarily longer initialization periods or an additional calculation, using a time window that allows it to follow the curvature. If yaw-rate was available, the center of road-scene-ahead could probably adapt to this signal and solve the problem, however this is not a common sensor in vehicles at the present time. The initialization phase can be seen in FIG. 49. The calibration process was tuned to work at an optimum using approximately five minutes of normal driving before producing valid values.

A similar problem arises when the driver is performing a task. The eyes do not seem to return to the center of the road-ahead area, but rather a few degrees in the direction of the secondary task (driving being the primary). Head bias could be the answer to this behavior meaning it is not perpendicular to the road-scene-ahead thus introducing a bias in the gaze estimate. The more the subject looks away from what is the road-scene-ahead the less accurate is the gaze estimate.

As soon as the initialization phase is finished, the DualVT-I, DT-I and rules are enabled. The DualVT-I first identifies saccade-fixation combinations. This, the shortest form of a glance, is then forwarded to the DT-I and rules along with its glance time. Mini glances, for instance a sequence of fixations within an area are joined if they belong to the same area; that is, glances according to the ISO/SAE standards are formed. Glance times are summed and forwarded to a counter synchronized with an on/off-road-ahead signal, which is the output from the clustering algorithm as depicted in FIG. 35. The counter registers all glances and glance-times belonging to the same task and is then reset for every new task. Before the reset is performed, however, the data is sent processed for logging purposes. In this case, time-gaps have been used to indicate the beginning and ending of tasks.

The algorithms have been validated to data from the VDM validation study utilizing video transcription. The video transcription was conducted according to the ISO 15007-2 and the SAEJ-2396 method. Using seven subjects, four measures where compared: 1) task length; 2) glance frequency; 3) average glance duration; and 4) Total glance time.

The validation was preformed task-by-task with every glance visually confirmed to ensure proper algorithm function. A few fixations were automatically restored using the restoration algorithm that proved to work very well and actually did no miscalculations.

Pearson product-movement revealed high correlations between analysis types on all important measures: task length $r=0.999$, glance frequency $r=0.998$, average glance duration $r=0.816$ and total glance duration $r=0.995$. This is to be compared with the results in "Automating Driver Visual Behavior Measurement" where the correlations where $r=0.991$, $r=0.997$, $r=0.732$ and $r=0.995$ respectively. FIGS. 50-53 plot the mean and standard deviations for each task.

The real-time algorithm has been validated against six video transcribed subjects from the VDM validation study. One of the subjects used in the offline validation had to be left out due to the absence of a baseline drive (no calibration data).

Three measures where compared: 1) Number of glances; 2) Total glance time; and 3) Average glance time.

Figure 54:
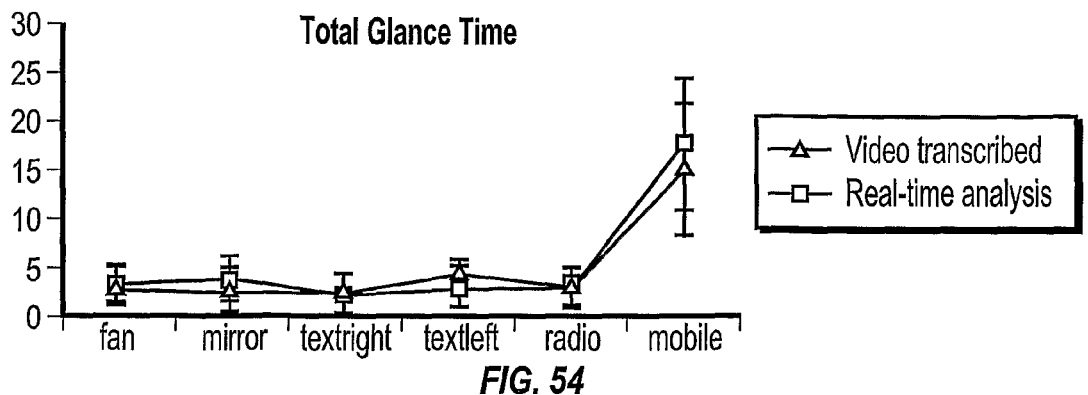
FIGS. 54-56 are graphical demonstrations of certain statistical analysis of glance data.
Figure 55:
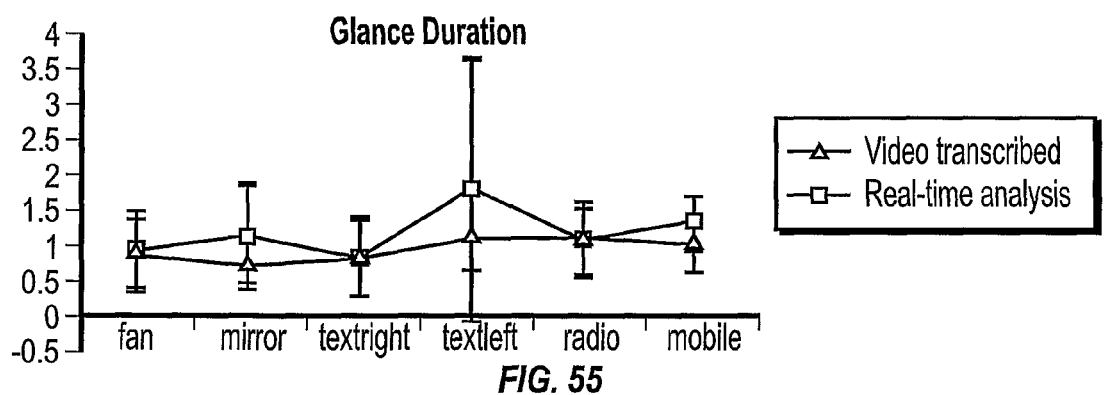
Figure 56:
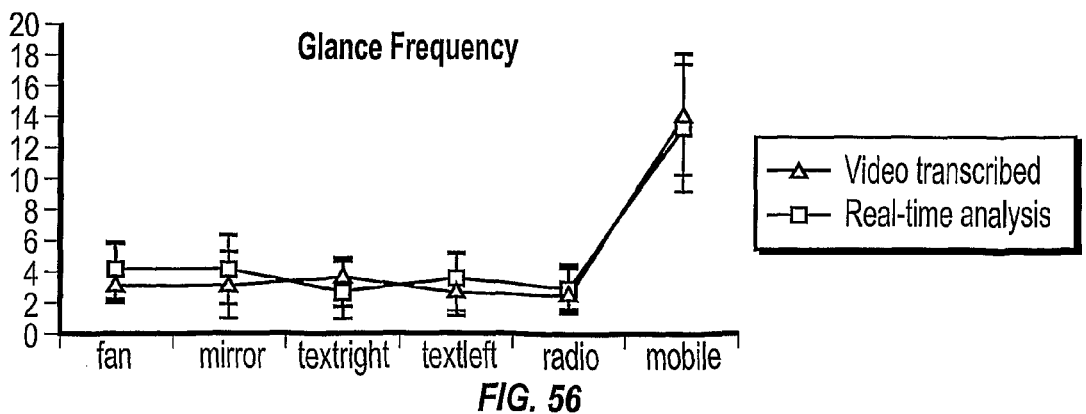

The entire drive of each subject was run in series through the algorithm. To be on the safe side every run started with 20 minutes of normal motorway (baseline) driving to calibrate the system although only five minutes are required. Pearson product-movement revealed high correlations between analysis type on two measures: Number of glances, r=0.925, and Total glance time, r=0.964. Average glance time, however, did not correlate very well, r=0.301. FIGS. 54-56 plot the means and standard deviations for each task.

The results from the validation prove that the algorithms are outstandingly reliable, even when data quality is not at its optimum level; for example, the algorithms are robust to varying noise level and signal accuracy. Also, using ocular motion rules, the algorithm can retrieve fixations that have almost vanished in the signal.

The correlation between analysis methods is very high, in the region of 0.99 (offline version) for all measures except average glance duration, which is still strong (r=0.82). A low correlation could however be expected from a measure based on two others.

The preprocessing also proved to worked well. The 15-sample median filter preserved saccade beginnings/terminations while subduing noise and blinks very efficiently.

The combination of the DualVT-I, the DT-I and the rules proved to work beyond expectations. The accuracy of the DualVT-I and the reliability of the DT-I in collaboration with the physical rules for eye movements formed an algorithm that is robust to temporary sensor confidence drops and high noise levels.

It has been shown that it is possible to have robust and reliable real-time glance detection. The simulation reveled high correlations on two measures (number of glances and total glance time). The correlation for average glance time was, however, low (r=0.301). Keeping in mind that the real time algorithm cannot differ a glance towards the mirror from one to the radio, all measures could be expected to be rather low. It is it is possible to make the real-time algorithm as accurate as the off-line version. This will be achieved by identifying the objects most commonly looked at inside the vehicle; for example, the interior mirror, side mirrors, instrument cluster and center stack. These objects are fairly spread out in the vehicle and therefore will not be confused with each other. Moreover, it should take only one or two glances in the area that is defined as the most probable area for one of those objects to start an initiation phase for this particular object. The objects most commonly looked at are the ones contributing the most to this error and these are also the ones that are the easiest to detect.

Since no other data set is video transcribed or in any other way analyzed, it has only been used for testing different algorithm parts e.g. the real-time initialization. However, this work has opened the door for the analysis of this data.

A robust hybrid algorithm that works according to the definitions and measures in the ISO 15007-2 and SAEJ-2396 standards has been developed. The method is substantially faster than video transcription, one hour of data takes about one day to video transcribe compared to a few minutes with the algorithms which also automatically adapts to the present noise level.

During the course of the development of the present invention(s), the following achievements have been observed: 1) The preprocessing median filtering length is optimized to 15 samples for data sampled at 60 Hz; 2) A median filter with 20 samples is used on noisy signal parts where, according to the ocular rules, there should be a fixation. This calms the signal enough to detect the fixation; 3) A robust hybrid of two fixation/saccade detection algorithms, which adapts to the present noise level, and the decision algorithm has been developed and tuned for 60 Hz data; 4) Physical rules for eye movements are implemented as a smart decision-making and controlling algorithm; 5) An automatic and robust clustering method that requires a minimum of interaction has been developed for task analysis; 6) A real-time version of the algorithm has been developed and validated; 7) The real-time version of the algorithm uses a novel framework which segments glances into the "road-straight-ahead" or "other" categories; and 8) All measures in the ISO/SAE have been implemented.

This thesis opens doors for several interesting in-vehicle product applications which could make use of eye movement data to be tested in a real on-road environment. For example: workload estimation, attention estimation, drowsiness detection, adaptive interfaces, adaptive warnings etc. Ergonomic evaluations, HMI studies, studies of cognitive workload, distraction, drowsiness and the like are all potentially interesting applications of the inventions defined therein.

Thus, a new path into the drivers mind has been opened. In today's environment, there still are a few manual steps to carry out such as load and save data, visually inspect the segmentation and occasionally adjust the world model. It is contemplated, however, and well within the understanding of those persons skilled in the relevant art to automate these manual tasks and execute the same according to the present invention. This is especially the case with direct sunlight into the cameras that scatters fixations over large areas that sometimes even "melts" clusters together. Thus, that analysis tools become more robust and accurate, some of these steps will no longer be necessary and perhaps batch processing will be possible.

The invention contemplates having a real-time algorithm that works robustly and intelligently to provide vehicles (and researchers) with as much usable information as possible from the driver's eyes. The real-time algorithm will be able to classify several objects robustly and intelligently. The real-time adaptation of world model objects to the real world will log events and data. One interesting approach is to implement target areas as HMM states. Introducing this statistical approach target classification may be enhanced, as it would make the target area boundaries more floating. One interesting idea is to have world model areas pop up when ever fixations are registered outside or at a distance away from the other objects, a dynamic world model. The world model could use this history of objects to calibrate the world model and make intelligent decisions; for example, an entirely task driven identification of objects.

Regarding the detection algorithms, other sensor information can be utilized. In modern cars the CAN bus is full of sensor signals that might be useful to estimate gaze direction when tracking fails such as steering angle, turn indicator actuation, vehicle speed, and whether or not certain buttons are pressed. This could also provide information about the traffic environment and thus optimize segmentation parameters for specific traffic environments such as country, suburban and city traffic. A rather successful approach to recognizing large scale driving patterns has also been completed.

Other WHM-filters can be tested for finding out if there is a better way to reduce noise in the beginning of fixations away from the road where the restoration algorithm is used. The flora of filters seems to be enormous.

One way to support the algorithm could be the fact that a subject's head often moves in the same direction as the eyes, at least for lateral gaze. A drawback with this approach results from individual differences in subjects. Some subjects virtually do not move their head at all while some always do. Still, this might be a suitable way to aid the segmentation when gaze is noisy.

In the real-time algorithm, a prediction of the next six samples would increase speed with 100 ms. It has been shown that saccadic signals can be predicted, at least a few points, with very small errors using a five point quadratic predictor. Speed is of the highest importance in a real-time algorithm.

In light of what is mentioned above, it is clear that the fine tuning of these algorithms will continue in the future. One development that is already underway is an algorithm GUI, called "Visual Demand Measurement Tool" or simply "VDM-Tool". The purpose of this program is to make the analysis tools easy to use for anyone who whishes to analyze eye-movements.

Many aspects of the inventive analysis techniques, including both the methods and the arrangements upon which those methods may be executed, are disclosed. Important characteristics of the analysis include at least a partial basis on driver eye movements, and assessments being made on a real-time basis.

We claim:

1. A method of analyzing a location of driver visual interest derived from observation of driver physiological orientation in a vehicle, the method comprising:
   obtaining data descriptive of a plurality of driver gaze direction instances, wherein each driver gaze direction instance is defined by a data set;
   processing the data using a computer-based processor;
   classifying a plurality of the driver gaze direction instances as either on-location or off-location in preparation for further analysis related to the location of driver visual interest;
   starting a data treatment process by determining off-location visual fixations based on a determination of on-location visual fixations by classifying data that is not classified as on-location visual fixation as off-location data and ignoring the off-location visual fixation;
   clustering data derived from the classified driver gaze direction instances;
   transforming each of the plurality of classified driver gaze direction instances into one of two binary values representative of whether the respective driver gaze direction instance is on-location or off-location thus forming a classification signal which determines in each sample or unit of time whether the location of driver visual interest is on-location or off-location;
   computing a glance frequency by counting the number of on- and off intervals in the classification signal;
   computing a glance duration by regarding a start and end of each continuous segment classified in the same way; and
   computing a compiled data stream generated by treating the classified driver gaze direction instances with a real time hybrid algorithm which runs two tandem treatments of the classified driver gaze direction instances utilizing a standard filter and, in parallel, a stringent filter.

2. The method as recited in claim 1, wherein only an area where measurement devices provide optimal performance is regarded for driver gaze direction instances.

3. The method as recited in claim 1, wherein an actual road-center cluster as measured by measurement devices is constrained by a pre-defined road center area for analysis.

4. The method as recited in claim 1, wherein multiple road-center areas are defined in an overlay fashion when different visual behaviour correlating to different road characteristics is desired to be measured.

5. The method as recited in claim 1, wherein the binary values are 1 and 0, the 1 and 0 values being more quickly processible in the further analysis than the obtained data from which the 1 and 0 values are derived.

6. The method as recited in claim 1, wherein the classification of at least some of the off-location driver gaze direction instances is inferred from failure to meet the determined criteria for being classified as an on-location driver gaze direction instance.

7. The method as recited in claim 1, wherein the further analysis relates to times of elevated driver workload and not driver drowsiness.

8. The method as recited in claim 1, wherein each data set defining a driver gaze direction instance is derived from a sensed orientation of an abovewaist portion of the driver's body.

9. The method as recited in claim 1, wherein each data set defining a driver gaze direction instance is derived from a sensed orientation of an upper torso portion of the driver's body.

10. The method as recited in claim 9, wherein the sensed orientation of an upper torso position is sensed using an ultrasonic device.

11. The method as recited in claim 9, wherein the sensed orientation of the head of the driver is sensed using a camera sensor.

12. The method as recited in claim 1, wherein each data set defining a driver gaze direction instance is derived from a sensed orientation of the head of the driver.

13. The method as recited in claim 12, wherein the sensed orientation of the head of the driver is sensed using a camera sensor.

14. The method as recited in claim 12, wherein the sensed orientation of the head of the driver is sensed using a capacitive sensor.

15. The method as recited in claim 1, wherein each data set defining a driver gaze direction instance is derived from a sensed orientation of at least one eye of the driver.

16. The method as recited in claim 1, wherein the location is a road-center location.

17. The method of claim 16, further comprising analyzing the classified gaze direction instances using a computer-based processor and determining therefrom whether an excessive amount of driver attention is being paid to the off-road-center location based on an assessment of driver workload.

18. The method of claim 17, further comprising initiating, stimulation of the driver's attention to driving control tasks after determining an excessive amount of driver attention is being paid to the off-location.

19. The method as recited in claim 1, wherein the location is a rear-view mirror location.

20. The method as recited in claim 1, wherein the location is a side-mirror location.

21. The method as recited in claim 1, wherein the location is a car accessory location.

22. The method as recited in claim 1, wherein the location is a personal accessory.

23. The method of claim 1, further comprising analyzing the classified gaze direction instances using, a computer-based processor and determining therefrom whether an excessive amount of driver attention is being, paid to the off-location based on an assessment of driver workload.

24. The method of claim 23, further comprising initiating stimulation of the driver's attention to driving control tasks after determining an excessive amount of driver attention is being paid to the off-location.

25. The method of claim 24, further comprising detecting a driving control task performance decrement prior to stimulating the driver's attention.

26. The method of claim 25, wherein the driving control task performance decrement is based on inconsistent steering.

27. The method of claim 25, wherein the driving control task performance decrement is based on inconsistent lane keeping.

28. The method of claim 25, wherein the driving control task performance decrement is based on inconsistent vehicle speed.

* * * * *